US012569497B2

(12) United States Patent
Khoo et al.

(10) Patent No.: US 12,569,497 B2
(45) Date of Patent: Mar. 10, 2026

(54) USE OF HCN INHIBITORS FOR TREATMENT OF CANCER

(71) Applicant: The University of Hong Kong, Hong Kong (HK)

(72) Inventors: Ui Soon Khoo, Hong Kong (HK); Ho Frankie Tsoi, Hong Kong (HK); Chun Jade Gong, Hong Kong (HK); Kin Wah Terence Lee, Hong Kong (HK)

(73) Assignee: The University Of Hong Kong, Hong Kong (CN)

( * ) Notice: Subject to any disclaimer, the term of this patent is extended or adjusted under 35 U.S.C. 154(b) by 681 days.

(21) Appl. No.: 16/607,035

(22) PCT Filed: Apr. 25, 2018

(86) PCT No.: PCT/CN2018/084417
§ 371 (c)(1),
(2) Date: Oct. 21, 2019

(87) PCT Pub. No.: WO2018/196782
PCT Pub. Date: Nov. 1, 2018

(65) Prior Publication Data

US 2023/0140818 A1 May 4, 2023

Related U.S. Application Data

(60) Provisional application No. 62/490,774, filed on Apr. 27, 2017.

(51) Int. Cl.

| | |
|---|---|
| ***A61K 31/55*** | (2006.01) |
| ***A61P 1/00*** | (2006.01) |
| ***A61P 1/16*** | (2006.01) |
| ***A61P 15/08*** | (2006.01) |
| ***A61P 35/00*** | (2006.01) |
| ***C07K 16/28*** | (2006.01) |
| ***C12N 15/113*** | (2010.01) |
| *A61K 39/00* | (2006.01) |

(52) U.S. Cl.
CPC ................ *A61K 31/55* (2013.01); *A61P 1/00* (2018.01); *A61P 1/16* (2018.01); *A61P 15/08* (2018.01); *A61P 35/00* (2018.01); *C07K 16/28* (2013.01); *C12N 15/1138* (2013.01); *A61K 39/00* (2013.01); *C07K 2317/24* (2013.01); *C12N 2310/531* (2013.01)

(58) Field of Classification Search
None
See application file for complete search history.

(56) References Cited

U.S. PATENT DOCUMENTS 7,176,197 B2 2/2007 Lerestif

OTHER PUBLICATIONS

Poolos, "Hyperpolarization-Activated Cyclic Nucleotide-Gated (HCN) Ion Channelopathy in Epilepsy", Jasper's Basic Mechanisms of the Epilepsies [Internet]. 4th Edition, 1-18 (2012).
Postea, "Exploring HCN Channels as Novel Drug Targets", Nature Reviews Drug Discovery, 10:903-914 (2011).
Santoro, et al., "Molecular and Functional Heterogeneity of Hyperpolarization-Activated Pacemaker Channels in the Mouse Cns", J. Neurosci., 20:5264-5275 (2000).
Thollon, et al., "Use-dependent Inhibition of hHCN4 by Ivabradine and Relationship With Reduction in Pacemaker Activity", British Journal of Pharmacology, 150:37-46 (2007).

*Primary Examiner* — Ruixiang Li
(74) *Attorney, Agent, or Firm* — Pabst Patent Group LLP

(57) ABSTRACT

Described are methods for treating cancers overexpressing hyperpolarization activated cyclic nucleotide-gated channel (HCN) isoforms HCN1, HCN2, HCN3, and/or HCN4. The cancers are treated by administering to a subject in need of treatment an effective amount of an HCN inhibitor. The HCN inhibitor can be an inhibitor of HCN1, HCN2, HCN3, or HCN4, or an inhibitor that inhibits any combination of HCN1, HCN2, HCN3, and HCN4. The described methods are useful for reducing tumor size, putting cancer in remission, and reducing or stopping proliferation of cancer stem cells.

12 Claims, 23 Drawing Sheets

Specification includes a Sequence Listing.

TCGA Colorectal cancer dataset showed the mRNA expression of HCN2 in tumor tissues compared to normal tissue (P=0.047, Fold change=1.225).

TCGA Colorectal cancer dataset showed the mRNA expression of HCN3 in tumor tissues compared to normal tissue (P=0.021, Fold change=1.186).

Lu ovarian cancer dataset showed the mRNA expression of HCN2 in tumor tissues compared to normal tissue (P=0.029, Fold change=1.277).

Yoshihara ovarian cancer dataset showed the mRNA expression of HCN3 in tumor tissues compared to normal tissue (P=0.006, Fold change=1.520).

Cancer Genome Atlas (TCGA) dataset of hepatocellular carcinoma showed the mRNA expression of HCN2 in tumor tissue compared with non-tumor tissue (p <0.001).

Cancer Genome Atlas (TCGA) dataset of hepatocellular carcinoma showed the mRNA expression of HCN3 in tumor tissue compared with non-tumor tissue (p <0.001).

From dataset GSE25097, overexpression of HCN2 was significantly correlated with poorer disease free survival (p=0.039).

Disease free survival

From dataset GSE25097, overexpression of HCN3 showed a trend of poorer overall survival (p=0.054)

Overall survival

Oncomine datasets for lung adenocarcinoma

HCN2 expression in Okayama lung, mRNA expression in tumor tissue compared with non-tumor tissue HCN3 expression in Selamat lung, mRNA expression in tumor tissue compared with non-tumor tissue ($p=3.55 \times 10^{-11}$)

Western blot analysis of HCN2 and HCN3 in colorectal and ovarian cancer cell lines Western blot analysis of HCN2 and HCN3 in a panel of Hepatocellular cancer cell lines Effect of Ivabradine (200μM) on Ishikawa ovarian cancer cells Effect of Ivabradine (200μM) on SW1116 colon cancer cells Effect of Ivabradine (200µM) on PLC/PRF/5 Hepatocellular cancer cells Effect of Ivabradine (200µM) on MHCC-97L Hepatocellular cancer cells Effect of Ivabradine (200μM) on Huh7 Hepatocellular cancer cells.

Colony formation results of 14 days treatment with Ivabradine (200μM) on ovarian and colorectal cancer cell lines Colony formation results of 14 days treatment with Ivabradine (200μM) on hepatocellular cancer cell lines

USE OF HCN INHIBITORS FOR TREATMENT OF CANCER

CROSS-REFERENCE TO RELATED APPLICATIONS

This application is a National Phase application under 35 U.S.C. 371 of International Application No. PCT/CN2018/084417, filed Apr. 25, 2018, which claims priority to and benefit of U.S. Provisional Application No. 62/490,774, filed Apr. 27, 2017, which are incorporated herein by reference in their entirety.

REFERENCE TO SEQUENCE LISTING

The Sequence Listing submitted Dec. 9, 2021, as a text file named "UHK_00700 substitute_ST25.txt," created on Nov. 23, 2021, and having a size of 1,189 bytes is hereby incorporated by reference pursuant to 37 C.F.R. § 1.52(e)(5).

FIELD OF THE INVENTION

The disclosed invention is generally in the field of cancer therapeutics and specifically in the area of treating cancers by targeting overexpressed nucleotide-gated channels.

BACKGROUND OF THE INVENTION

Breast cancer is the most common type of malignancy affecting women worldwide with 1.6 million new cases and 500,000 deaths were reported in 2012, making it also the leading cause of cancer death. In Hong Kong, its incidence has been steadily rising over the last few decades, with age-standardized incidence and mortality rates of 61.2 and 9.5 per 100,000 respectively in 2012 (Hong Kong Cancer Registry, 2013).

The majority of breast cancer patients express either estrogen receptor alpha (ERα), progesterone receptor (PR) or overexpress human epidermal growth factor receptor 2 (HER2) and can be treated with anti-hormone or anti-HER2 targeted therapy (Yeo et al., *Bmj-British Medical Journal,* 348 (2014)). However, 10-15% of breast cancer patients lack the expression of the above receptors; this type of breast cancer is regarded as triple negative breast cancer (TNBC) (Collignon et al., *Breast Cancer-Targets and Therapy,* 8:93-107 (2016)).

These negative results mean that the growth of the cancer is not supported by the hormones estrogen and progesterone or by the overexpression of HER2 receptors. Therefore, triple-negative breast cancer does not respond to hormonal therapy (such as tamoxifen or aromatase inhibitors) or therapies that target the HER2 receptors, such as Herceptin (chemical name: trastuzumab). Chemotherapy, albeit with severe side effects, appears to be the only option for this group of patients (Zeichner et al., *Breast Cancer-Basic and Clinical Research,* 10:25-36 (2016)).

There remains a need for effective therapies against cancer, particularly against triple negative breast cancer.

Therefore, it is an object of the invention to provide compositions for treating cancers, particularly triple negative breast cancer.

It is a further object of the invention to provide methods of treating cancers, particularly triple negative breast cancer.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF SUMMARY OF THE INVENTION

Disclosed are compounds, compositions, and methods for treating cancer. In particular, disclosed are compounds, compositions, and methods for treating tumors and cancers using an inhibitor of hyperpolarization-activated cyclic nucleotide-gated channel (HCN). The methods include administering to a subject in need of such treatment an effective amount of an HCN inhibitor. The disclosed compositions and methods are particularly useful for treating a tumor or cancer overexpressing an HCN.

The HCN inhibitor can be selected from a group consisting of a small molecule, an antibody, an inhibitory nucleic acid, and combinations thereof. Examples of HCN inhibitors include ivabradine, ivabradine prodrug, ivabradine derivatives, chimeric antibodies specific to HCN, antibody fragments specific to HCN, RNA interference molecules specific to HCN, and combinations thereof. The inhibitor can be a specific inhibitor of HCN isoform 1 (HCN1), HCN isoform 2 (HCN2), HCN isoform 3 (HCN3), or HCN isoform 4 (HCN4). In some embodiments, the inhibitor can be a specific inhibitor of HCN2 and HCN3. In other embodiments, the inhibitor can be a specific inhibitor of HCN2 and HCN3 but not of HCN1 or HCN4.

In some embodiments, the tumor or cancer to be treated can be breast cancer, including triple-negative breast cancer, ovarian cancer, uterine cancer, prostate cancer, testicular germ cell tumor, brain cancer, gastric cancer, esophagus cancer, lung cancer, liver cancer, and colon cancer.

Typically, the methods include administering the HCN inhibitors, or pharmaceutical compositions containing HCN inhibitors, orally, systemically, enterally, parenterally, locally, topically, or via buccal routes. The pharmaceutical compositions include compositions containing an HCN inhibitor and a pharmaceutically acceptable carrier.

Disclosed are methods for treating a tumor or cancer involving administering to a subject in need of such treatment an effective amount of a hyperpolarization-activated cyclic nucleotide-gated channel (HCN) inhibitor. In some forms, administering can be by oral, systemic, enteral, parenteral, local, topical, or buccal routes. In some forms, the subject can be a mammal. In some forms, the subject can be a human.

In some forms, the tumor or cancer can be breast cancer, ovarian cancer, uterine cancer, prostate cancer, testicular germ cell tumor, brain cancer, gastric cancer, esophagus cancer, lung cancer, liver cancer, and colon cancer. In some forms, the tumor or cancer can be triple-negative breast cancer.

In some forms, the effective amount can be effective to reduce tumor size. In some forms, the effective amount can be effective to put the cancer in remission. In some forms, the effective amount can be effective to reduce at least one symptom of cancer. In some forms, the effective amount can be effective to reduce or stop proliferation of cancer stem cells.

In some forms, the inhibitor can be a small molecule, an antibody, an inhibitory nucleic acid, or combinations thereof. In some forms, the inhibitor can be ivabradine, ivabradine prodrug, ivabradine derivatives, chimeric antibodies specific to HCN, antibody fragments specific to HCN, RNA interference molecules specific to HCN, or combinations thereof.

Also disclosed are pharmaceutical compositions including an HCN inhibitor and a pharmaceutically acceptable carrier. In some forms, the composition can comprise an isolated antibody or a binding fragment thereof specific to HCN and a pharmaceutically acceptable carrier. In some forms, the composition can comprise a nucleic acid molecule encoding an inhibitory nucleic acid molecule against HCN expression and a pharmaceutically acceptable carrier. In some forms, the nucleic acid molecule can encode a sequence according to SEQ ID NO: 1. In some forms, the HCN inhibitor of the composition can be ivabradine, an ivabradine prodrug, or an ivabradine derivative.

In some forms, the inhibitor can be a specific inhibitor of HCN isoform 1 (HCN1), HCN isoform 2 (HCN2), HCN isoform 3 (HCN3), or HCN isoform 4 (HCN4). In some form, the inhibitor can be a specific inhibitor of HCN2 and HCN3. In some forms, the inhibitor can be a specific inhibitor of HCN2 and HCN3 but not of HCN1 or HCN4.

The methods include administering an amount of an HCN inhibitor, or a pharmaceutical composition containing an amount of an HCN inhibitor, effective to reduce at least one symptom of cancer, reduce tumor size, to put the cancer in remission, and/or to reduce or stop proliferation of cancer stem cells.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 13 shows Oncomine datasets (mRNA expression) for lung adenocarcinoma, wherein.

FIG. 18 shows the results of 14 days of treatment with Ivabradine (200 μM) on various cancer cell lines, wherein

DETAILED DESCRIPTION OF THE INVENTION

Figure 1A:
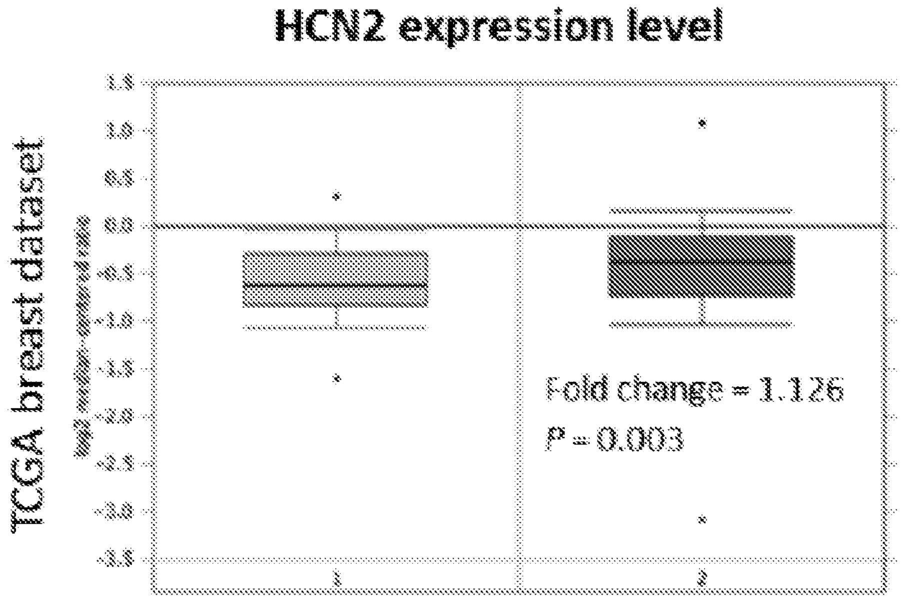
FIGS. 1A, 1B, 1C, and 1D are box and whiskers plots showing HCN2 (FIGS. 1A and 1B) and HCN3 (FIGS. 1C and 1D) mRNA expression in breast tissue from normal subjects and breast tissue from subjects with invasive ductal carcinoma. The data were obtained from available TCGA, Radvanyi and Curtis datasets. Student t-test was used to determine the statistical significance.
Figure 1B:
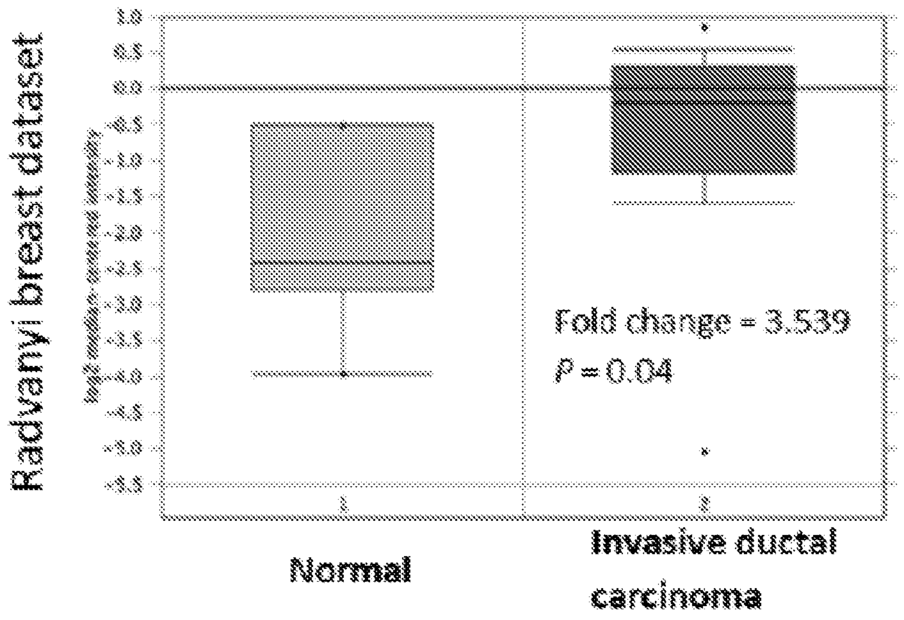
Figure 1C:
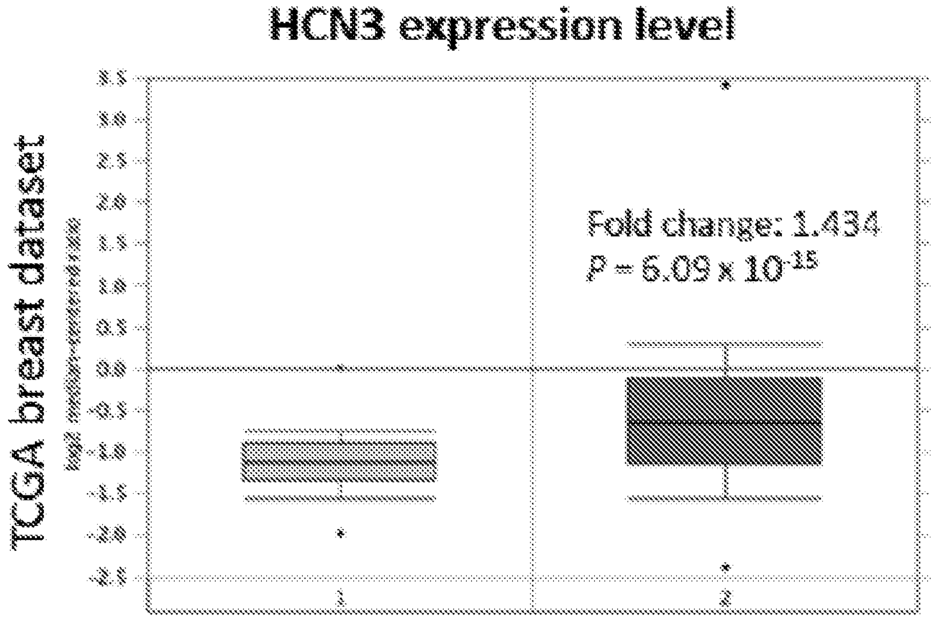
Figure 1D:
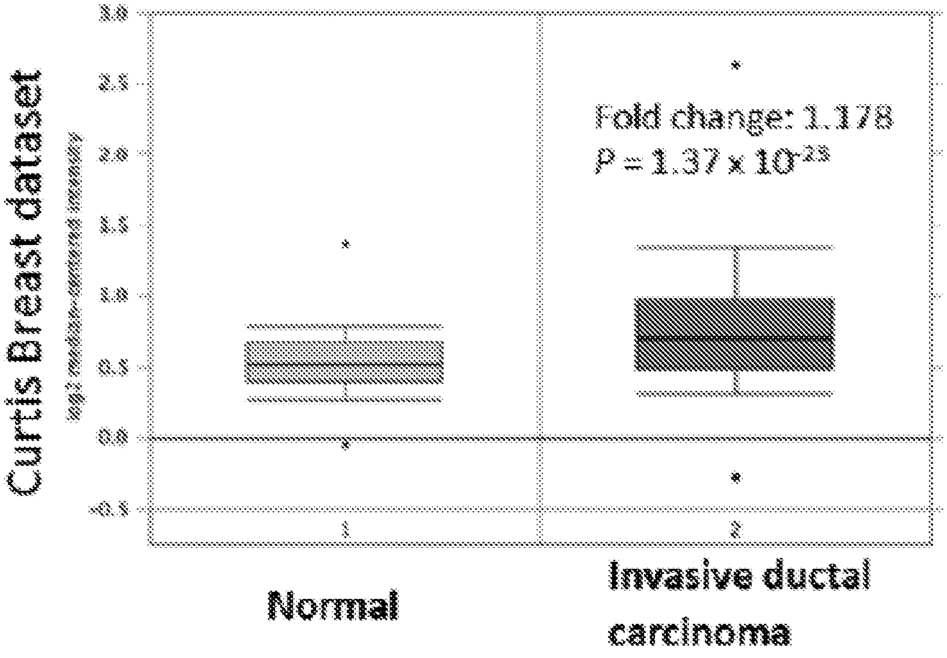

The disclosed compositions and method may be understood more readily by reference to the following detailed description of particular embodiments and the Examples included therein and to the Figures and their previous and following description.

Disclosed herein are compositions for treating cancer and methods of making and using the compositions. The compositions may be administered to a subject with cancer in an effective amount to effect a reduction in at least one symptom of cancer, to reduce tumor size, to keep the cancer in remission, and/or to reduce or stop the proliferation of cancer stem cells.

It is to be understood that the disclosed compositions and method are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

A. Definitions

As used herein, the term “inhibitor” refers to compounds effecting inhibition of the activity and/or expression of any of HCN1, HCN2, HCN3, and HCN4 in cells, tissues, organs, bodies, or subjects. The inhibitor may be a small molecule, a metal, an antibody, an inhibitory nucleic acid, and any combinations thereof. The inhibitor inhibits the activity and/or expression of any of HCN1, HCN2, HCN3, and HCN4.

As used herein, the terms “inhibit” or “reduce” in the context of inhibition, mean to reduce or decrease in activity or expression. This can be a complete inhibition or reduction of activity or expression, or a partial inhibition or reduction. Inhibition or reduction can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%. For example, an inhibitor may inhibit or reduce the activity and/or expression of any of HCN1, HCN2, HCN3, and HCN4 by about 10%, 15%, 20%, 25%, 30%, 35%, 40%, 45%, 50%, 55%, 60%, 65%, 70%, 75%, 80%, 85%, 90%, 95%, or 99% from the activity and/or expression of the same molecule(s) in cells, tissues, organs, bodies, or subjects that did not receive, or were not treated with, the inhibitor.

As used herein, the term “subject” refers to, for example, animals, plants, bacteria, viruses, parasites and any other organism or entity. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As used herein, the term "in need of treatment" refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that include the knowledge that the subject is ill, or will be ill, as the result of a condition that is treatable by the compounds of the invention.

As used herein, the terms "treatment" and "treating" refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

As used herein, the term "modulate" refers to the ability of a compound to change an activity in some measurable way as compared to an appropriate control. As a result of the presence of compounds in the assays, activities can increase or decrease as compared to controls in the absence of these compounds. Preferably, an increase in activity is at least 25%, more preferably at least 50%, most preferably at least 100% compared to the level of activity in the absence of the compound. Similarly, a decrease in activity is preferably at least 25%, more preferably at least 50%, most preferably at least 100% compared to the level of activity in the absence of the compound. A compound that increases a known activity is an "agonist". One that decreases, or prevents, a known activity is an "antagonist".

As used herein, the term "monitoring" refers to any method in the art by which an activity can be measured.

As used herein, the term "providing" refers to any means of adding a compound or molecule to something known in the art. Examples of providing can include the use of pipettes, pipettemen, syringes, needles, tubing, guns, etc. This can be manual or automated. It can include transfection by any mean or any other means of providing nucleic acids to dishes, cells, tissue, cell-free systems and can be in vitro or in vivo.

As used herein, the term "effective amount" refers to a nontoxic but sufficient amount of the compound to provide the desired result. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation.

As used herein, the term "pharmaceutically acceptable" refers to a material that is not biologically or otherwise undesirable, i.e., the material can be administered to a subject along with the selected compound without causing any undesirable biological effects or interacting in a deleterious manner with any of the other components of the pharmaceutical composition in which it is contained.

Any of the compounds described herein can be used therapeutically in combination with a pharmaceutically acceptable carrier. The compounds described herein can be conveniently formulated into pharmaceutical compositions composed of one or more of the compounds in association with a pharmaceutically acceptable carrier. See, e.g., *Remington's Pharmaceutical Sciences*, latest edition, by E. W. Martin Mack Pub. Co., Easton, PA, which discloses typical carriers and conventional methods of preparing pharmaceutical compositions that can be used in conjunction with the preparation of formulations of the compounds described herein and which is incorporated by reference herein. These most typically would be standard carriers for administration of compositions to humans. In one aspect, humans and non-humans, including solutions such as sterile water, saline, and buffered solutions at physiological pH. Other compounds will be administered according to standard procedures used by those skilled in the art.

As used herein, the term "overexpression" refers to expression of a gene or protein that is greater than the normal or average expression for normal or typical cells, or of cells of the same type. For example, if a breast cell exhibits higher expression of a gene or protein than the normal expression of normal breast cells, that breast cell can be said to overexpress that gene or protein. Similarly, if a cancer cell exhibits higher expression of a gene or protein than the typical expression of typical cancer cells of the same type, that cancer cell can be said to overexpress that gene or protein. As another example, if a breast cancer cell exhibits higher expression of a gene or protein than the typical expression of typical breast cancer cells, that breast cancer cell can be said to overexpress that gene or protein. As another example, if a breast cancer cell exhibits higher expression of a gene or protein than the normal expression of normal breast cells, that breast cancer cell can be said to overexpress that gene or protein. Thus, overexpression generally will be in reference to a normal or typical expression level and can differ depending on what is used for the comparison or reference expression level. Overexpression can be, for example, 5%, 10%, 15%, 20%, 25%, 30%, 35%, 40%, 50%, 60%, 70%, 75% 80%, 90%, 100%, 120%, 140%, 150%, 160%, 180%, 200%, 250%, 300%, 350%, 400%, 500%, 600%, 700%, 800%, 900%, 1,000%, or more greater than the reference, measuring, normal, or control expression.

As used herein, the term "under-expression" refers to expression of a gene or protein that is lower than the normal or average expression for normal or typical cells, or of cells of the same type. For example, if a breast cell exhibits lower expression of a gene or protein than the normal expression of normal breast cells, that breast cell can be said to under-express that gene or protein. Similarly, if a cancer cell exhibits lower expression of a gene or protein than the typical expression of typical cancer cells of the same type, that cancer cell can be said to under-express that gene or protein. As another example, if a breast cancer cell exhibits lower expression of a gene or protein than the typical expression of typical breast cancer cells, that breast cancer cell can be said to under-express that gene or protein. As another example, if a breast cancer cell exhibits lower expression of a gene or protein than the normal expression of normal breast cells, that breast cancer cell can be said to under-express that gene or protein. Thus, under-expression generally will be in reference to a normal or typical expression level and can differ depending on what is used for the comparison or reference expression level.

As used herein, the term "small molecule" refers to small organic compounds having a molecular weight of more than about 100 and less than about 2,500 Daltons, preferably between 100 and 2000, more preferably between about 100 and about 1250, more preferably between about 100 and about 1000, more preferably between about 100 and about 750, more preferably between about 200 and about 500 Daltons. The small molecules can include cyclical carbon or heterocyclic structures and/or aromatic or polyaromatic structures substituted with one or more functional groups.

As used herein, the term "antibody" refers to both polyclonal and monoclonal antibodies. In addition to intact immunoglobulin molecules, also included are fragments or polymers of those immunoglobulin molecules, and human or humanized versions of immunoglobulin molecules or fragments thereof, as long as the molecules maintain the ability to bind with an epitope of the HCN1, HCN2, HCN3, and/or HCN4. The antibodies can be tested for their desired activity using the in vitro assays, or by analogous methods, after which their in vivo therapeutic and/or diagnostic activities can be confirmed and quantified according to known clinical testing methods.

In some embodiments, the antibody is a monoclonal antibody or a binding fragment thereof. A monoclonal antibody refers to an antibody where individual antibodies within a population are identical.

As used herein, the term "isolated antibody" refers to an antibody which is substantially free of other antibodies having different antigenic specificities (e.g., an isolated antibody that specifically binds to HCN1, HCN2, HCN3, and/or HCN4, is substantially free of antibodies that specifically bind antigens other than HCN1, HCN2, HCN3, and/or HCN4). An isolated antibody that specifically binds to an epitope, isoform or variant of HCN1, HCN2, HCN3, and/or HCN4 may, however, have cross-reactivity to other HCN1, HCN2, HCN3, and/or HCN4 forms, analogs or related antigens, e.g., from other species. Moreover, an isolated antibody may be substantially free of other cellular material and/or chemicals.

As used herein, the terms "binding fragment", "antigen binding fragment", "antibody binding fragment", and the like, refer to one or more portions of an antibody that contain the antibody's CDRs and, optionally, the framework residues that comprise the antibody's "variable region" antigen recognition site, and exhibit an ability to immunospecifically bind antigen. Such fragments include Fab', F(ab')2, Fv, single chain (ScFv), etc., and mutants and variants thereof, naturally occurring variants. As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

The variable regions can also be substituted and altered in ways that do not eliminate the binding and binding specificity of the variable region or CDRs. For the disclosed antibodies and polypeptides with substitutions, alterations, eliminations, etc. of portions of antibodies other than the variable regions (or other than the CDRs), it is preferred that the variable region sequences and the CDR sequences are, or are modeled after, the variable regions or CDRs of HCN1, HCN2, HCN3, and HCN4 antibodies.

As used herein, the term "chimeric antibody" refers to a molecule in which different portions of the antibody are derived from different immunoglobulin molecules such as antibodies having a variable region derived from a non-human antibody and a human immunoglobulin constant region. Methods for producing chimeric antibodies are known in the art. See e.g., Morrison, 1985, *Science* 229:1202; Oi et al., 1986, *BioTechniques* 4:214; Gillies et al., 1989, *J. Immunol. Methods* 125:191-202; and U.S. Pat. Nos. 6,311,415, 5,807,715, 4,816,567, and 4,816,397. Chimeric antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519,596; Padlan, 1991, *Molecular Immunology* 28(4/5):489-498; Studnicka et al., 1994, *Protein Engineering* 7:805; and Roguska et al., 1994, *Proc. Natl. Acad. Sci. USA* 91:969), and chain shuffling (U.S. Pat. No. 5,565,332).

A chimeric antibody may be a "humanized antibody" (see, e.g., European Patent Nos. EP 239,400, EP 592,106, and EP 519,596; International Publication Nos. WO 91/09967 and WO 93/17105; U.S. Pat. Nos. 5,225,539, 5,530,101, 5,565,332, 5,585,089, 5,766,886, and 6,407,213; and Padlan, 1991, *Molecular Immunology* 28(4/5):489-498; Studnicka et al., 1994, *Protein Engineering* 7(6):805-814; Roguska et al., 1994, *PNAS* 91:969-973; Tan et al., 2002, *J. Immunol.* 169:1119-1125; Caldas et al., 2000, *Protein Eng.* 13:353-360; Morea et al., 2000, *Methods* 20:267-79; Baca et al., 1997, *J. Biol. Chem.* 272:10678-10684; Roguska et al., 1996, *Protein Eng.* 9:895-904; Couto et al., 1995, *Cancer Res.* 55 (23 Supp):5973s-5977s; Couto et al., 1995, *Cancer Res.* 55:1717-22; Sandhu, 1994, *Gene* 150:409-10; Pedersen et al., 1994, *J. Mol. Biol.* 235:959-973; Jones et al., 1986, *Nature* 321:522-525; Reichmann et al., 1988, *Nature* 332:323-329; and Presta, 1992, *Curr. Op. Struct. Biol.* 2:593-596).

As used herein, the term "humanized antibody" refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A humanized antibody is an antibody comprising a humanized light chain and a humanized heavy chain immunoglobulin. For example, a humanized antibody would not encompass a typical chimeric antibody, because, e.g., the entire variable region of a chimeric antibody is non-human. One says that the donor antibody has been "humanized" by the process of "humanization" because the resultant humanized antibody is expected to bind to the same antigen as the donor antibody that provides the CDR's. For the most part, humanized antibodies are human immunoglobulins (recipient antibody) in which hypervariable region residues of the recipient are replaced by hypervariable region residues from a non-human species (donor antibody) such as mouse, rat, rabbit or a non-human primate having the desired specificity, affinity, and capacity. In some instances, Framework Region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin that immunospecifically binds to an FcγRIIB polypeptide, that has been altered by the introduction of amino acid residue substitutions, deletions or additions (i.e., mutations).

DNA sequences coding for preferred human acceptor framework sequences include but are not limited to FR segments from the human germline VH segment VH1-18 and JH6 and the human germline VL segment VK-A26 and JK4. In a specific embodiment, one or more of the CDRs are inserted within framework regions using routine recombinant DNA techniques. The framework regions may be naturally occurring or consensus framework regions, and preferably human framework regions (see, e.g., Chothia et al., 1998, *"Structural Determinants In The Sequences Of Immunoglobulin Variable Domain,"* J. Mol. Biol. 278: 457-479 for a listing of human framework regions).

As used herein, the terms "binding specificity", "specificity", "specifically reacts", "specifically interacts", or "specific to" refers to the ability of an antibody or other agent to detectably bind an epitope presented on an antigen, such as epitopes of any one of HCN1, HCN2, HCN3, and HCN4, while having relatively little detectable reactivity with other proteins or structures. Specificity can be relatively determined by binding or competitive assays, using e.g., Biacore instruments. Specificity can be exhibited by, e.g., an about 10:1, about 20:1, about 50:1, about 100:1, about 10,000:1 or greater ratio of affinity/avidity in binding to the specific antigen versus nonspecific binding to other irrelevant molecules. In the context of the disclosed antibodies and polypeptides, "bi-specific" and similar terms refer to antibodies or polypeptides containing at least two different specific binding elements that each specifically binds to a different epitope or ligand.

As used herein, the term "inhibitory nucleic acid" refers to nucleic acid compositions that reduce or eliminate the expression of a target gene. Typically, the inhibitory nucleic acid will have some degree of complementarity with a region of a target gene. Exemplary inhibitory nucleic acids include antisense oligonucleotides, catalytic nucleic acids such as ribozymes and deoxyribozymes, aptamers, triplex forming nucleic acids, external guide sequences, and RNA interference molecules (RNAi).

As used herein, the term "RNA interference molecules" refers to molecules are between about 20 and 25 base pairs in length, that interfere with the expression of specific genes. The RNA interference molecules are designated as RNAi. To interfere with the expression of specific genes (target genes), RNAi usually have some nucleotide sequence complementarity with (specificity to) a region in the target gene. The complementarity between the RNAi and the region in the target gene may be for about 5 nucleotides of the target gene, 6 nucleotides of the target gene, 7 nucleotides of the target gene, 8 nucleotides of the target gene, 9 nucleotides of the target gene, 10 nucleotides of the target gene, 11 nucleotides of the target gene, 12 nucleotides of the target gene, 13 nucleotides of the target gene, 14 nucleotides of the target gene, or 15 nucleotides of the target gene. The complementarity between RNAi molecule and the target gene may be along consecutive nucleotides, or non-consecutive nucleotides.

As used herein, the term "prodrug" refers to a compound that has negligible, or lower, activity than one of its major metabolites. Activity may be a pharmacological activity specific to a target. An example is a pharmacological substance (drug) administered in an inactive (or significantly less active) form, which is then metabolized in the body (in vivo) into the active compound.

As used herein, the terms "analog" and "derivative" refer to in the context of chemical compounds, are used herein interchangeably, and refer to a compound having a structure similar to that of a parent compound, but varying from the parent compound by a difference in one or more certain components. (Designation as a parent compound does not mean that the parent compound is used as a starting material or intermediate but is rather a structural relationship.) Analogs or derivatives differ from the parent compound in one or more atoms, functional groups, or substructures, which are replaced with other atoms, groups, or substructures. An analog or derivative can be imagined to be formed, at least theoretically, from the parent compound via some chemical or physical process. The terms analog and derivative encompass compounds which retain the same basic chemical structure as the parent compound, but possess one or more different substituents. For example, an analog or derivative of ivabradine, or "ivabradine derivative" refers to a compound that retains the core of ivabradine, e.g., but differs in or more substituents on any of the rings or chains. In some embodiments, an analog or derivative retains at least, 20, 30, 40, 50, 60, 70, 80, 90, or 100% of a selected activity of a reference compound, e.g., a parent compound.

As used herein, the term "substantially" specifies an amount of 95% or more, 96% or more, 97% or more, 98% or more, or 99% or more.

As used herein, the term "substituted" refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, arylalkyl, substituted arylalkyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups. Such alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, arylalkyl, substituted arylalkyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups can be further substituted.

Heteroatoms such as nitrogen may have hydrogen substituents and/or any permissible substituents of organic compounds described herein which satisfy the valences of the heteroatoms. It is understood that “substitution” or “substituted” includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

Except where specifically and expressly provided to the contrary, the term “substituted” refers to a structure, e.g., a chemical compound or a moiety on a larger chemical compound, regardless of how the structure was formed. The structure is not limited to a structure made by any specific method.

As used herein, the term “aryl” refers to $C_5$-$C_{26}$-membered aromatic, fused aromatic, fused heterocyclic, or biaromatic ring systems. Broadly defined, “aryl”, as used herein, includes 5-, 6-, 7-, 8-, 9-, 10-, 14-, 18-, and 24-membered single-ring aromatic groups, for example, benzene, naphthalene, anthracene, phenanthrene, chrysene, pyrene, corannulene, coronene, etc.

The term “aryl” further encompasses polycyclic ring systems having two or more cyclic rings in which two or more carbons are common to two adjoining rings (i.e., “fused rings”) wherein at least one of the rings is aromatic, e.g., the other cyclic ring or rings can be cycloalkyls, cycloalkenyls, cycloalkynyls, aryls and/or heterocycles.

As used herein, the term “substituted aryl” refers to an aryl group, where one or more hydrogen atoms on one or more aromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfoxide, sulfonamido, sulfonyl, heterocyclyl, alkylaryl, haloalkyl (such as $CF_3$, $—CH_2—CF_3$, $—CCl_3$), —CN, aryl, heteroaryl, and combinations thereof.

As used herein, the terms “heterocycle”, “heterocyclic” and “heterocyclyl” are used interchangeably, and refer to a cyclic radical attached via a ring carbon or nitrogen atom of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Examples of heterocycles include, but are not limited to piperazinyl, piperidinyl, piperidonyl, 4-piperidonyl, dihydrofuro[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

As used herein, the term “heteroaryl” refers to $C_5$-$C_{26}$-membered aromatic, fused aromatic, biaromatic ring systems, or combinations thereof, in which one or more carbon atoms on one or more aromatic ring structures have been substituted with a heteroatom. Suitable heteroatoms include, but are not limited to, oxygen, sulfur, and nitrogen. Broadly defined, “heteroaryl”, as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as “aryl heterocycles” or “heteroaromatics”. “Heteroaryl” further encompasses polycyclic ring systems having two or more rings in which two or more carbons are common to two adjoining rings (i.e., “fused rings”) wherein at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined below for "substituted heteroaryl".

As used herein, the term "substituted heteroaryl" refers to a heteroaryl group in which one or more hydrogen atoms on one or more heteroaromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfoxide, sulfonamido, sulfonyl, heterocyclyl, alkylaryl, haloalkyl (such as $CF_3$, $—CH_2—CF_3$, $—CCl_3$), —CN, aryl, heteroaryl, and combinations thereof.

As used herein, the term "alkyl" refers to the radical of saturated aliphatic groups, including straight-chain alkyl, alkenyl, or alkynyl groups, branched-chain alkyl, cycloalkyl (alicyclic), alkyl substituted cycloalkyl groups, and cycloalkyl substituted alkyl. In preferred embodiments, a straight chain or branched chain alkyl has 30 or fewer carbon atoms in its backbone (e.g., $C_1$-$C_{30}$ for straight chains, $C_3$-$C_{30}$ for branched chains), preferably 20 or fewer, more preferably 15 or fewer, most preferably 10 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfoxide, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

An alkyl can include one or more substitutions at one or more carbon atoms of the hydrocarbon radical as well as heteroalkyls. Suitable substituents include, but are not limited to, halogens, such as fluorine, chlorine, bromine, or iodine; hydroxyl; —NRR', wherein R and R' are independently hydrogen, alkyl, or aryl, and wherein the nitrogen atom is optionally quaternized; —SR, wherein R is hydrogen, alkyl, or aryl; —CN; $—NO_2$; —COOH; carboxylate; —COR, —COOR, or $—CON(R)_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, haloalkyl (such as $—CF_3$, $—CH_2—CF_3$, $—CCl_3$); —CN; $—NCOCOCH_2CH_2$; —NCOCOCHCH; —NCS; and combinations thereof.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl, sulfoxide, and sulfonate), and silyl groups, as well as ethers, alkylthios, carbonyls (including ketones, aldehydes, carboxylates, and esters), haloalkyls, —CN and the like. Cycloalkyls can be substituted in the same manner.

As used herein, the terms "alkenyl" and "alkynyl" refer to unsaturated aliphatic groups analogous in length and possible substitution to the alkyls described above, but that contain at least one double or triple bond, respectively.

As used herein, the term "substituted alkenyl" refers to alkenyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

As used herein, the term "substituted alkynyl" refers to alkynyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

As used herein, the term "phenyl" is art-recognized and refers to the aromatic moiety $—C_6H_5$, i.e., a benzene ring without one hydrogen atom.

As used herein, the term "substituted phenyl" refers to a phenyl group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

As used herein, the terms "amino" and "amine" are art-recognized and refer to both substituted and unsubstituted amines, e.g., a moiety that can be represented by the general formula:

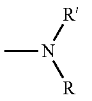 or 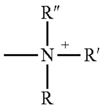

wherein, R, R', and R" each independently represent a hydrogen, substituted or unsubstituted alkyl, substituted or unsubstituted alkenyl, substituted or unsubstituted alkynyl, substituted or unsubstituted carbonyl, —$(CH_2)_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide. In preferred embodiments, R and R' (and optionally R") each independently represent a hydrogen atom, substituted or unsubstituted alkyl, a substituted or unsubstituted alkenyl, or —$(CH_2)_m$—R'''. Thus, the term 'alkylamine' as used herein refers to an amine group, as defined above, having a substituted or unsubstituted alkyl attached thereto (i.e. at least one of R, R', or R" is an alkyl group).

As used herein, the term "carbonyl" is art-recognized and includes such moieties as can be represented by the general formula:

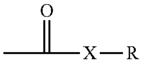 or 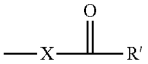

wherein X is a bond, or represents an oxygen or a sulfur, and R represents a hydrogen, a substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, —$(CH_2)_m$—R", or a pharmaceutical acceptable salt, R' represents a hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl or —$(CH_2)_m$—R"; R" represents a hydroxy group, substituted or unsubstituted carbonyl group, an aryl, a cycloalkyl ring, a cycloalkenyl ring, a heterocycle, or a polycycle; and in is zero or an integer ranging from 1 to 8. Where X is oxygen and R is defines as above, the moiety is also referred to as a carboxyl group. When X is oxygen and R is hydrogen, the formula represents a 'carboxylic acid'. Where X is oxygen and R' is hydrogen, the formula represents a 'formate'. Where X is oxygen and R or R' is not hydrogen, the formula represents an "ester". In general, where the oxygen atom of the above formula is replaced by a sulfur atom, the formula represents a 'thiocarbonyl' group. Where X is sulfur and R or R' is not hydrogen, the formula represents a 'thioester'. Where X is sulfur and R is hydrogen, the formula represents a 'thiocarboxylic acid'. Where X is sulfur and R' is hydrogen, the formula represents a 'thioformate'. Where X is a bond and R is not hydrogen, the above formula represents a 'ketone'. Where X is a bond and R is hydrogen, the above formula represents an 'aldehyde'.

As used herein, the term "substituted carbonyl" refers to a carbonyl, as defined above, wherein one or more hydrogen atoms in R, R' or a group to which the moiety

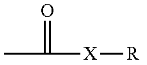 or 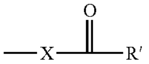

is attached, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

As used herein, the term "carboxyl" is as defined above for the formula

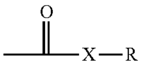 or 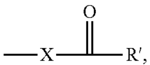, and is defined more specifically by the formula —$R^{iv}$COOH, wherein $R^{iv}$ is an alkyl, alkenyl, alkynyl, cycloalkyl, heterocyclyl, alkylaryl, arylalkyl, aryl, or heteroaryl. In preferred embodiments, a straight chain or branched chain alkyl, alkenyl, and alkynyl have 30 or fewer carbon atoms in its backbone (e.g., $C_1$-$C_{30}$ for straight chain alkyl, $C_3$-$C_{30}$ for branched chain alkyl, $C_2$-$C_{30}$ for straight chain alkenyl and alkynyl, $C_3$-$C_{30}$ for branched chain alkenyl and alkynyl), preferably 20 or fewer, more preferably 15 or fewer, most preferably 10 or fewer. Likewise, preferred cycloalkyls, heterocyclyls, aryls, and heteroaryls have from 3-10 carbon atoms in their ring structure, and more preferably have 5, 6 or 7 carbons in the ring structure.

As used herein, the term "substituted carboxyl" refers to a carboxyl, as defined above, wherein one or more hydrogen atoms in $R^{iv}$ are substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

As used herein, the term "heteroalkyl" refers to straight or branched chain, or cyclic carbon-containing radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized.

Examples of saturated hydrocarbon radicals include, but are not limited to, methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, and 3-butynyl.

As used herein, the terms "alkoxyl" or "alkoxy", "aroxy" or "aryloxy" generally describe compounds represented by the formula —OR$^v$, wherein R$^v$ includes, but is not limited to, substituted or unsubstituted alkyl, alkenyl, alkynyl, cycloalkyl, heterocyclyl, cycloalkenyl, heterocycloalkenyl, aryl, heteroaryl, arylalkyl, heteroalkyls, alkylaryl, alkylheteroaryl.

As used herein, the terms "alkoxyl" or "alkoxy" refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. The term alkoxy also includes cycloalkyl, heterocyclyl, cycloalkenyl, heterocycloalkenyl, and arylalkyl having an oxygen radical attached to at least one of the carbon atoms, as valency permits.

As used herein, the term "substituted alkoxy" refers to an alkoxy group having one or more substituents replacing one or more hydrogen atoms on one or more carbons of the alkoxy backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

As used herein, the term "phenoxy" is art recognized and refers to a compound of the formula —OR' wherein R$^v$ is (i.e., —O—$C_6H_5$). One of skill in the art recognizes that a phenoxy is a species of the aroxy genus.

As used herein, the term "substituted phenoxy" refers to a phenoxy group, as defined above, having one or more substituents replacing one or more hydrogen atoms on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

As used herein, the terms "aroxy" and "aryloxy" refer to —O-aryl or —O— heteroaryl, wherein aryl and heteroaryl are as defined herein.

As used herein, the terms "substituted aroxy" and "substituted aryloxy" refer to —O-aryl or —O-heteroaryl, having one or more substituents replacing one or more hydrogen atoms on one or more ring atoms of the aryl and heteroaryl, as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

As used herein, the term "alkylthio" refers to an alkyl group, as defined above, having a sulfur radical attached thereto. The "alkylthio" moiety is represented by —S—alkyl. Representative alkylthio groups include methylthio, ethylthio, and the like. The term "alkylthio" also encompasses cycloalkyl groups having a sulfur radical attached thereto.

As used herein, the term "substituted alkylthio" refers to an alkylthio group having one or more substituents replacing one or more hydrogen atoms on one or more carbon atoms of the alkylthio backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

As used herein, the term "phenylthio" is art recognized and refers to —S—$C_6H_5$, i.e., a phenyl group attached to a sulfur atom.

As used herein, the term "substituted phenylthio" refers to a phenylthio group, as defined above, having one or more substituents replacing a hydrogen on one or more carbons of the phenyl ring. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

As used herein, the term "arylthio" refers to —S-aryl or —S-heteroaryl groups, wherein aryl and heteroaryl as defined herein.

As used herein, the term "substituted arylthio" refers to —S-aryl or —S-heteroaryl, having one or more substituents replacing a hydrogen atom on one or more ring atoms of the aryl and heteroaryl rings as defined herein. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

As used herein, the term "arylalkyl" refers to an alkyl group that is substituted with a substituted or unsubstituted aryl or heteroaryl group.

As used herein, the term "alkylaryl" refers to an aryl group (e.g., an aromatic or hetero aromatic group), substituted with a substituted or unsubstituted alkyl group.

As used herein, the terms "amide" or "amido" refer to both "unsubstituted amido" and "substituted amido" and are represented by the general formula:

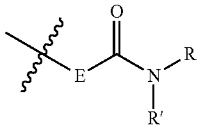

wherein, E is absent, or E is substituted or unsubstituted alkyl, substituted or unsubstituted alkenyl, substituted or unsubstituted alkynyl, substituted or unsubstituted aralkyl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R'''$, or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide. In preferred embodiments, R and R' each independently represent a hydrogen atom, substituted or unsubstituted alkyl, a substituted or unsubstituted alkenyl, or $-(CH_2)_m-R'''$. When E is oxygen, a carbamate is formed. The carbamate cannot be attached to another chemical species, such as to form an oxygen-oxygen bond, or other unstable bonds, as understood by one of ordinary skill in the art.

As used herein, the term "sulfonyl" refers to structures of the formula

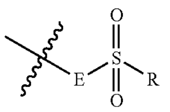

where E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R'''$, or E and R taken together with the S atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of E and R can be substituted or unsubstituted amine, to form a "sulfonamide" or "sulfonamido". The substituted or unsubstituted amine is as defined above.

As used herein, the term "substituted sulfonyl" refers to a sulfonyl in which E, R, or both, are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

As used herein, the term "sulfonic acid" refers to a sulfonyl, as defined above, wherein R is hydroxyl, and E is absent, or E is substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl.

As used herein, the term "sulfate" refers to a sulfonyl, as defined above, wherein E is absent, oxygen, alkoxy, aroxy, substituted alkoxy or substituted aroxy, as defined above, and R is independently hydroxyl, alkoxy, aroxy, substituted alkoxy or substituted aroxy, as defined above. When E is oxygen, the sulfate cannot be attached to another chemical species, such as to form an oxygen-oxygen bond, or other unstable bonds, as understood by one of ordinary skill in the art.

As used herein, the term "sulfonate" refers to a sulfonyl, as defined above, where E is oxygen, alkoxy, aroxy, substituted alkoxy or substituted aroxy, as defined above, and R is independently hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R'$, R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. When E is oxygen, sulfonate cannot be attached to another chemical species, such as to form an oxygen-oxygen bond, or other unstable bonds, as understood by one of ordinary skill in the art.

As used herein, the term "sulfamoyl" refers to a sulfonamide or sulfonamide represented by the formula

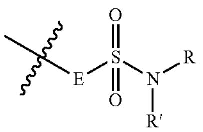

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein independently of E, R and R' each independently represent a hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R'''$, or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide.

As used herein, the term "sulfoxide" refers to structures of the formula

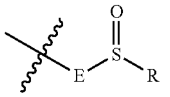

wherein E is absent, or E is alkyl, alkenyl, alkynyl, aralkyl, alkylaryl, cycloalkyl, aryl, heteroaryl, heterocyclyl, wherein independently of E, R represents a hydrogen, substituted or unsubstituted alkyl, substituted or unsubstituted alkenyl, substituted or unsubstituted alkynyl, substituted or unsubstituted amine, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R'''$, or E and R taken together with the S atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

As used herein, the term "phosphonyl" refers to structures of the formula

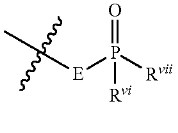

wherein E is absent, or E is substituted or unsubstituted alkyl, substituted or unsubstituted alkenyl, substituted or unsubstituted alkynyl, substituted or unsubstituted aralkyl, substituted or unsubstituted alkylaryl, substituted or unsubstituted cycloalkyl, substituted or unsubstituted aryl, substituted or unsubstituted heteroaryl, substituted or unsubstituted heterocyclyl, wherein, independently of E, $R^{vi}$ and $R^{vii}$ are independently hydrogen, substituted or unsubstituted alkyl, substituted or unsubstituted alkenyl, substituted or unsubstituted alkynyl, substituted or unsubstituted carbonyl, substituted or unsubstituted cycloalkyl, substituted or unsubstituted heterocyclyl, substituted or unsubstituted alkylaryl, substituted or unsubstituted arylalkyl, substituted or unsubstituted aryl, or substituted or unsubstituted heteroaryl, $-(CH_2)_m-R'''$, or R and R' taken together with the P atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8.

As used herein, the term "substituted phosphonyl" refers to a phosphonyl in which E, $R^{vi}$ and $R^{vii}$ are independently substituted. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

As used herein, the term "phosphoryl" refers to a phosphonyl in which E is absent, oxygen, alkoxy, aroxy, substituted alkoxy or substituted aroxy, as defined above, and independently of E, $R^{vi}$ and $R^{vii}$ are independently hydroxyl, alkoxy, aroxy, substituted alkoxy or substituted aroxy, as defined above. When E is oxygen, the phosphoryl cannot be attached to another chemical species, such as to form an oxygen-oxygen bond, or other unstable bonds, as understood by one of ordinary skill in the art. When E, $R^{vi}$ and $R^{vii}$ are substituted, the substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

As used herein, the term "polyaryl" refers to a chemical moiety that includes two or more aryls, heteroaryls, and combinations thereof. The aryls, heteroaryls, and combinations thereof, are fused, or linked via a single bond, ether, ester, carbonyl, amide, sulfonyl, sulfonamide, alkyl, azo, and combinations thereof.

As used herein, the term "substituted polyaryl" refers to a polyaryl in which one or more of the aryls, heteroaryls are substituted, with one or more substituents including, but not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfoxide, sulfonamido, sulfonyl, heterocyclyl, alkylaryl, haloalkyl, —CN, aryl, heteroaryl, and combinations thereof.

As used herein, the term "$C_3$-$C_{20}$ cyclic" refers to a substituted or unsubstituted cycloalkyl, substituted or unsubstituted cycloalkenyl, substituted or unsubstituted cycloalkynyl, substituted or unsubstituted heterocyclyl that have from three to 20 carbon atoms, as geometric constraints permit. The cyclic structures are formed from single or fused ring systems. The substituted cycloalkyls, cycloalkenyls, cycloalkynyls and heterocyclyls are substituted as defined above for the alkyls, alkenyls, alkynyls and heterocyclyls, respectively.

As used herein, the terms "hydroxyl" and "hydroxy" are used interchangeably and are represented by —OH.

As used herein, the terms "thiol" and "sulfhydryl" are used interchangeably and are represented by —SH.

As used herein, the term "oxo" refers to =O bonded to a carbon atom.

As used herein, the terms "cyano" and "nitrile" are used interchangeably to refer to —CN.

As used herein, the term "nitro" refers to —$NO_2$.

As used herein, the term "phosphate" refers to —O—$PO_3$.

As used herein, the term "azide" or "azido" are used interchangeably to refer to —$N_3$.

As used herein, the term "substituted $C_1$-$C_x$ alkyl" refers to alkyl groups having from one to x carbon atoms, wherein at least one carbon atom is substituted, wherein "x" is an integer from one to ten. The term "unsubstituted $C_1$-$C_x$ alkyl" refers to alkyl groups having from one to x carbon atoms that are not substituted, wherein "x" is an integer from one to ten.

As used herein, the term "substituted $C_1$-$C_x$ alkylene" refers to alkylene groups having from one to x carbon atoms, wherein at least one carbon atom is substituted, wherein "x" is an integer from one to ten. The term "unsubstituted $C_1$-$C_x$ alkylene" refers to alkylene groups having from one to x carbon atoms that are not substituted, wherein "x" is an integer from one to ten. The term "alkylene" as used herein, refers to a moiety with the formula —$(CH_2)_a$—, wherein "a" is an integer from one to ten.

As used herein, the term "substituted $C_2$-$C_x$ alkenyl" refers to alkenyl groups having from two to x carbon atoms, wherein at least one carbon atom is substituted, wherein "x" is an integer from two to ten. The term "unsubstituted $C_2$-$C_x$ alkenyl" refers to alkenyl groups having from two to x carbon atoms that are not substituted, wherein "x" is an integer from two to ten.

As used herein, the term "substituted $C_2$-$C_x$ alkynyl" refers to alkynyl groups having from two to x carbon atoms, wherein at least one carbon atom is substituted, wherein "x" is an integer from two to ten. The term "unsubstituted $C_2$-$C_x$ alkynyl" refers to alkynyl groups having from two to x carbon atoms that are not substituted, wherein "x" is an integer from two to ten.

As used herein, the term "substituted $C_1$-$C_x$ alkoxy" refers to alkoxy groups having from one to x carbon atoms, wherein at least one carbon atom is substituted, wherein "x" is an integer from one to ten. The term "unsubstituted $C_1$-$C_x$ alkoxy" refers to alkoxy groups having from one to x carbon atoms that are not substituted, wherein "x" is an integer from one to ten.

As used herein, the term "substituted $C_1$-$C_x$ alkylamino" refers to alkylamino groups having from one to x carbon atoms, wherein at least one carbon atom is substituted, wherein "x" is an integer from one to ten. The term "unsubstituted $C_1$-$C_x$ alkylamino" refers to alkyl groups having from one to x carbon atoms that are not substituted, wherein "x" is an integer from one to ten. The terms "alkylamine" and "alkylamino" are used interchangeably. In any alkylamino, where the nitrogen atom is substituted with one, two, or three substituents, the nitrogen atom can be referred to as a secondary, tertiary, or quaternary nitrogen atom, respectively.

As used herein, the term "substituted $C_1$-$C_x$ alkylthio" refers to alkylthio groups having from one to x carbon atoms, wherein at least one carbon atom is substituted, wherein "x" is an integer from one to ten. The term "unsubstituted $C_1$-$C_x$ alkylthio" refers to alkylthio groups having from one to x carbon atoms that are not substituted, wherein "x" is an integer from one to ten.

As used herein, the term "substituted $C_1$-$C_x$ carbonyl" refers to carbonyl groups having from one to x carbon atoms, wherein at least one carbon atom is substituted, wherein "x" is an integer from one to ten. The term "unsubstituted $C_1$-$C_x$ carbonyl" refers to carbonyl groups having from one to x carbon atoms that are not substituted, wherein "x" is an integer from one to ten.

As used herein, the term "substituted $C_1$-$C_x$ carboxyl" refers to carboxyl groups having from one to x carbon atoms, wherein at least one carbon atom is substituted, wherein "x" is an integer from one to ten. The term "unsubstituted $C_1$-$C_x$ carboxyl" refers to carboxyl groups having from one to x carbon atoms that are not substituted, wherein "x" is an integer from one to ten.

As used herein, the term "substituted $C_1$-$C_x$ amido" refers to amido groups having from one to x carbon atoms, wherein at least one carbon atom is substituted, wherein "x" is an integer from one to ten. The term "unsubstituted $C_1$-$C_x$ amido" refers to amido groups having from one to x carbon atoms that are not substituted, wherein "x" is an integer from one to ten.

As used herein, the term "substituted $C_1$—C, sulfonyl" refers to sulfonyl groups having from one to x carbon atoms, wherein at least one carbon atom is substituted, wherein "x" is an integer from one to ten. The term "unsubstituted $C_1$-$C_x$ sulfonyl" refers to sulfonyl groups having from one to x, carbon atoms that are not substituted, wherein "x" is an integer from one to ten.

As used herein, the term "substituted $C_1$—C, sulfonic acid" refers to sulfonic acid groups having from one to x carbon atoms, wherein at least one carbon atom is substituted, wherein "x" is an integer from one to ten. The term "unsubstituted $C_1$-$C_x$ sulfonic acid" refers to sulfonic acid groups having from one to x carbon atoms that are not substituted, wherein "x" is an integer from one to ten.

As used herein, the term "substituted $C_1$-$C_x$ sulfamoyl" refers to sulfamoyl groups having from one to x carbon atoms, wherein at least one carbon atom is substituted, wherein "x" is an integer from one to ten. The term "unsubstituted $C_1$-$C_x$ sulfamoyl" refers to sulfamoyl groups having from one to x carbon atoms that are not substituted, wherein "x" is an integer from one to ten.

As used herein, the term "substituted $C_1$—C, sulfoxide" refers to sulfoxide groups having from one to x carbon atoms, wherein at least one carbon atom is substituted, wherein "x" is an integer from one to ten. The term "unsubstituted $C_1$-$C_x$ sulfoxide" refers to sulfoxide groups having from one to x carbon atoms that are not substituted, wherein "x" is an integer from one to ten.

As used herein, the term "substituted $C_1$-$C_x$ phosphoryl" refers to phosphoryl groups having from one to x carbon atoms, wherein at least one carbon atom is substituted, wherein "x" is an integer from one to ten. The term "unsubstituted $C_1$-$C_x$ phosphoryl" refers to phosphoryl groups having from one to x carbon atoms that are not substituted, wherein "x" is an integer from one to ten.

As used herein, the term "substituted $C_1$-$C_x$ phosphonyl" refers to phosphonyl groups having from one to x carbon atoms, wherein at least one carbon atom is substituted, wherein "x" is an integer from one to ten. The term "unsubstituted $C_1$-$C_x$ phosphonyl" refers to phosphonyl groups having from one to x carbon atoms that are not substituted, wherein "x" is an integer from one to ten.

As used herein, the term "substituted $C_0$-$C_x$ sulfonyl" refers to sulfonyl groups having from zero to x carbon atoms, wherein, if present, at least one carbon atom is substituted, wherein "x" is an integer from zero to ten. The term "unsubstituted $C_0$-$C_x$ sulfonyl" refers to sulfonyl groups having from zero to x carbon atoms that are not substituted, wherein "x" is an integer from zero to ten.

As used herein, the term "substituted $C_0$-$C_x$ sulfonic acid" refers to sulfonic acid groups having from zero to x carbon atoms, wherein, if present, at least one carbon atom is substituted, wherein "x" is an integer from zero to ten. The term "unsubstituted $C_0$-$C_x$ sulfonic acid" refers to sulfonic acid groups having from zero to x carbon atoms that are not substituted, wherein "x" is an integer from zero to ten.

As used herein, the term "substituted $C_0$-$C_x$ sulfamoyl" refers to sulfamoyl groups having from zero to x carbon atoms, wherein, if present, at least one carbon atom is substituted, wherein "x" is an integer from zero to ten. The term "unsubstituted $C_0$-$C_x$ sulfamoyl" refers to sulfamoyl groups having from zero to x carbon atoms that are not substituted, wherein "x" is an integer from zero to ten.

As used herein, the term "substituted $C_0$-$C_x$ sulfoxide" refers to sulfoxide groups having from zero to x carbon atoms, wherein at least one carbon atom is substituted, wherein "x" is an integer from zero to ten. The term "unsubstituted $C_0$-$C_x$ sulfoxide" refers to sulfoxide groups having from zero to x carbon atoms that are not substituted, wherein "x" is an integer from zero to ten.

As used herein, the term "substituted $C_0$-$C_x$ phosphoryl" refers to phosphoryl groups having from zero to x carbon atoms, wherein, if present, at least one carbon atom is substituted, wherein "x" is an integer from zero to ten. The term "unsubstituted $C_0$—C, phosphoryl" refers to phosphoryl groups having from zero to x carbon atoms that are not substituted, wherein "x" is an integer from zero to ten.

As used herein, the term "substituted $C_0$-$C_x$ phosphonyl" refers to phosphonyl groups having from zero to x carbon atoms, wherein, if present, at least one carbon atom is substituted, wherein "x" is an integer from zero to ten. The term "unsubstituted $C_0$-$C_x$ phosphonyl" refers to phosphonyl groups having from zero to x carbon atoms that are not substituted, wherein "x" is an integer from zero to ten.

As used herein, the terms substituted "$C_x$ alkyl", "$C_x$ alkylene", "$C_x$ alkenyl", "$C_x$ alkynyl", "$C_x$ alkoxy", "$C_x$ alkylamino", "$C_x$ alkylthio", "$C_x$ carbonyl", "$C_x$ carboxyl", "$C_x$ amido", "$C_x$ sulfonyl", "$C_x$ sulfonic acid", "$C_x$ sulfamoyl", "$C_x$ phosphoryl", and "$C_x$ phosphonyl" refer to alkyl, alkylene, alkenyl, alkynyl, alkoxy, alkylamino, alkylthio, carbonyl, carboxyl, amido, sulfonyl, sulfonic acid, sulfamoyl, sulfoxide, phosphoryl, and phosphonyl groups, respectively, having x carbon atoms, wherein at least one carbon atom is substituted, wherein "x" is an integer from one to ten. The terms unsubstituted "$C_x$ alkyl", "$C_x$ alkylene", "$C_x$ alkenyl", "$C_x$ alkynyl", "$C_x$ alkoxy", "$C_x$ alkylamino", "$C_x$ alkylthio", "$C_x$ carbonyl", "$C_x$ carboxyl", "$C_x$ amido", "$C_x$ sulfonyl", "$C_x$ sulfonic acid", "$C_x$ sulfamoyl", "$C_x$ phosphoryl", and "$C_x$ phosphonyl" refer to alkyl, alkylene, alkenyl, alkynyl, alkoxy, alkylamino, alkylthio, carbonyl, carboxyl, amido, sulfonyl, sulfonic acid, sulfamoyl, sulfoxide, phosphoryl, and phosphonyl groups, respectively, having x carbon atoms that are not substituted, wherein "x" is an integer from one to ten.

As used herein, the terms unsubstituted "$C_0$ sulfonyl", "$C_0$ sulfonic acid", "Co sulfamoyl", "$C_0$ phosphoryl", and "$C_0$ phosphonyl" refer to alkyl, alkylene, alkenyl, alkynyl, alkoxy, alkylamino, alkylthio, carbonyl, carboxyl, amido, sulfonyl, sulfonic acid, sulfamoyl, sulfoxide, phosphoryl, and phosphonyl groups, respectively, having zero carbon atoms that are not substituted.

As used herein, the term "halogen" refers to fluorine, chlorine, bromine, or iodine.

As used herein, the term "activity" refers to a biological activity.

As used herein, the term "pharmacological activity" refers to the inherent physical properties of a peptide or polypeptide. These properties include but are not limited to half-life, solubility, and stability and other pharmacokinetic properties.

As used herein, the term "remission" refers to a decrease or a reduction of the seriousness or intensity of disease or pain; a temporary recovery. Reduction of the seriousness or intensity of disease or pain, in the context of remission, is a reduction in any one or all detectable markers or signs of a disease. For example, remission in a subject previously diagnosed with cancer may include a decrease in or disappearance of signs and symptoms of cancer. In partial remission, some, but not all, signs and symptoms of cancer have disappeared. In complete remission, all signs and symptoms of cancer have disappeared, although cancer still may be in the body.

As used herein, the term "reduce" refers to a decrease. This may be a decrease in activity or expression of a molecule, such as HCN1, HCN2 HCN3, or HCN4, or a decrease in a number of symptoms of a disease, or a decrease in a number of cells following a treatment, relative to a control.

As used herein, the term "cancer stem cells" refers to a subpopulation of cancer cells with stem cell characteristics. Cancer stem cells are capable of self-renewal and can give rise to tumors.

As used herein, the term "triple-negative breast cancer" refers to breast cancer characterized by the absence of three types of receptors—estrogen receptor, progesterone receptor, and human epidermal growth factor receptor 2 (HER2).

B. Hyperpolarization-Activated Cyclic Nucleotide-Gated Channels (HCN)

Hyperpolarization-activated Cyclic Nucleotide-gated channels (HCN) are expressed in four isoforms, HCN1, HCN2, HCN3, and HCN4. They are highly tissue specific, found mainly expressed in the heart and nervous system. HCN4 is the major isoform that controls heart rate and is one of the major determinants of cardiac pacemaker activity.

HCN represent a unique class of voltage-gated ion channels. Initially characterized in the heart as "pacemaker" channels, they are now understood to be an essential modulator of neuronal excitability in cortex, hippocampus, and thalamus. They are both voltage- and ligand-gated; they open with hyperpolarization of membrane potential rather than with depolarization.

HCN are voltage-gated ion channels that structurally resemble K+ channels, with a six-transmembrane domain topology, including a pore region that conducts ion flow. HCN possess biophysical properties that make them virtually unique in comparison to other voltage-gated channels. First, despite structural similarity to K+ channels, HCN are relatively less selective for K+ ions, allowing inward passage of Na+ ions. Because at typical neuronal resting potential the driving force for Na+ is so much greater than for K+, HCN primarily conduct Na+ current under physiological conditions, thus depolarizing neuronal membrane potential. Second, the voltage-dependent activation of HCN is also anomalous compared to most other channels: HCN are fractionally open at resting potential, and their activation increases with hyperpolarization from rest rather than with depolarization as is common with other channels. Thus neuronal depolarization tends to turn off HCN while hyperpolarization tends to activate them. Third, HCN do not display inactivation, thus are constitutively active around resting potential. Fourth, HCN open remarkably slowly, with activation time constants that range from tens to hundreds of milliseconds, i.e., several orders of magnitude slower than those of most ion channels. Finally, HCN are partly gated by intracellular levels of cyclic nucleotides such as cyclic adenosine 3',5'-monophosphate (cAMP). This allows channel activity to be modulated by both voltage and intracellular second messengers (Poolos NP. Hyperpolarization-Activated Cyclic Nucleotide-Gated (HCN) Ion Channelopathy in Epilepsy. In: Noebels J L, Avoli M, Rogawski M A, et al., editors. *Jasper's Basic Mechanisms of the Epilepsies* [*Internet*]. 4th edition. Bethesda (MD): National Center for Biotechnology Information (US); 2012).

HCN are encoded by four separate genes, HCN1, HCN2, HCN3, and HCN4 (Santoro et al., *J Neurosci.,* 20:5264-5275 (2000)). Ion channels encoded by each of the isoforms have differing biophysical properties (such as speed of gating and sensitivity to cAMP), and are also differentially distributed throughout the brain. HCN1 and HCN2 are the main brain isoforms, with HCN1 predominant in the neocortex and hippocampus, and HCN2 predominant in the thalamus. HCN3 has diffuse but low-level distribution in the brain, while HCN4 is a subtype present mostly in thalamic relay neurons. HCN1 has relatively fast activation times (tens of milliseconds), but virtual insensitivity to cAMP. HCN2 is the main subcortical (e.g., thalamic) isoform, with intermediate (several hundreds of milliseconds) activation time constants, and a depolarizing shift in its voltage-dependence on exposure to cAMP (Poolos (2012), supra).

HCN1 (also known as BCNG-1, BCNG1, HAC-2) is a membrane protein for a hyperpolarization-activated cation channel that contributes to the native pacemaker currents in heart and neurons. The protein can homodimerize or heterodimerize with other pore-forming subunits to form a potassium channel. This channel may act as a receptor for sour tastes. The mRNA for HCN1 has been detected at high levels in brain, heart muscle, and at lower levels in skeletal muscle and placenta. A few cancers including cases of malignant melanomas, colorectal and breast cancers displayed weak cytoplasmic positivity. Malignant cells in general are negative for the HCN1 protein (The Human Protein Atlas).

The HCN2 mRNA has been detected in brain, and at lower levels, in heart muscle. The protein for HCN2 is enriched in the heart and brain. The mRNA for HCN2 has been detected in various cell lines. The mRNA for HCN2 was found in brain cancer cell line U-87 MG (glioblastoma cell line), in lung cancer cell line A549 (lung carcinoma), and in breast cancer cell line MCF7 (adenocarcinoma) (The Human Protein Atlas).

The HCN3 protein is found in all major organs, except in parathyroid gland, lymph nodes, spleen, smooth muscle, bronchus, lung, epididymis, seminal vesicle, placenta, vagina, cervix, endometrium, adipose tissue, soft tissue, and skin. The HCN3 protein is found in breast cancer, carcinoid, cervical cancer, colorectal cancer, endometrial cancer, glioma, head and neck cancer, liver cancer, lung cancer, lymphoma, melanoma, ovarian cancer, pancreatic cancer, prostate cancer, skin cancer, stomach cancer, testis cancer, thyroid cancer, and urothelial cancer tissues (The Human Protein Atlas).

The HCN4 protein shows slow kinetics of activation and inactivation, and is necessary for the cardiac pacemaking process. This channel may also mediate responses to sour stimuli. Mutations in this gene have been linked to sick sinus syndrome 2, also known as atrial fibrillation with bradyarrhythmia or familial sinus bradycardia. Two pseudogenes have been identified on human chromosome 15. The HCN4 mRNA has been found enriched in brain, heart muscle and testis. Brain cancer cell line AF22, testicular embryonic carcinoma cell line NTERA-2 cell line, and bone osteosarcoma cell line U-2 OS show expression of the HCN4 mRNA.

Isoforms HCN2 and HCN3 are overexpressed in breast cancer cells compared with normal breast tissue.

C. Compositions

The compositions described herein are HCN1, HCN2, HCN3, and/or HCN4 inhibitors. The inhibitors may be small molecules; antibodies, such as chimeric antibodies, humanized antibodies, and antibody fragments; inhibitory nucleic acids; or any combination thereof.

1. Small Molecule Inhibitors

In some forms, the compositions are small molecules. Typically, the small molecule is a small organic compound having a molecular weight of more than about 100 and less than about 2,500 Daltons, preferably between 100 and 2000, more preferably between about 100 and about 1250, more preferably between about 100 and about 1000, more preferably between about 100 and about 750, more preferably between about 200 and about 500 Daltons. The small molecules can include cyclical carbon or heterocyclic structures and/or aromatic or polyaromatic structures substituted with one or more functional groups.

Small molecule inhibitors include, but are not limited to, ivabradine, prodrugs of ivabradine, and derivatives of ivabradine.

i. Ivabradine

Ivabradine, also known as 1.7,8-dimethoxy-3-(3-(((4,5-dimethoxybenzocyclobutan-1-yl)methyl)methylamino)propyl)-1,3,4,5-tetrahydro-2H-benzazepin-2-one, S 16257, S 16257-2, S 16260-2, S-16257, S-16257-2, or S-16260-2, has a chemical structure according to Formula I:

Formula I

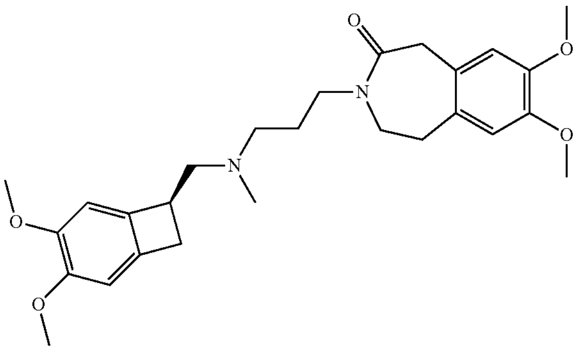

Ivabradine, ($C_{27}H_{36}N_2O_5$), has a molecular weight of 468.594 g/mol, and limited solubility in water, about 0.02 mg/ml. Ivabradine hydrochloride salt has improved water solubility of over 5 mg/ml.

Ivabradine is an HCN inhibitor. It is an FDA approved drug marketed under the trade name CORLANOR® (Biofarma, France). It is a medication used for the symptomatic management of stable heart related chest pain (angina) and heart failure not fully managed by beta blockers. Ivabradine is a cardiotonic agent and acts by reducing the heart rate via specific inhibition of the HCN, a mechanism different from that of beta blockers and calcium channel blockers, two commonly prescribed antianginal drugs. The maximum daily dose of CORLANOR®, as approved by the FDA is about 7 mg twice daily.

Ivabradine inhibits the homomeric HCN4 current in cells in vitro with at half maximal inhibitory concentration ($IC_{50}$) value of between 0.54 μM and 2.8 μM (Thollon et al., *British Journal of Pharmacology,* 150:37-46 (2007)). In addition to HCN4, Ivabradine can inhibit HCN1, HCN2 and HCN3 with $IC_{50}$ value of between 1.5 μM and 4.5 μM. (Postea, *Nature Reviews Drug Discovery,* 10:903-914 (2011)).

ii. Prodrugs and Derivatives of Ivabradine

Prodrugs and derivatives of ivabradine are molecules with a general chemical structure according to Formula I, but incorporating one or more substitutions. The substitutions may be one or more substitutions described herein.

The biological activity of the derivatives may be greater by at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 250%, about 300%, or about 350%, or more, relative to ivabradine hydrochloride activity when measured by the same assay under the same environmental conditions.

The derivatives generally have a biological activity that is about the same as, or is greater than, the biological activity of ivabradine. For example, the biological activity of an ivabradine inhibitor, such as a HCN1, HCN2, HCN3, and/or HCN4 inhibitor, the biological activity is any activity in the biological systems, such as channel current inhibition, channel activity inhibition, cell depolarization inhibition, cell proliferation inhibition, cell cycle arrest induction, cell apoptosis induction, and so on.

2. Antibodies

Native antibodies are usually heterotetrameric glycoproteins, composed of two identical light chains (LC) and two identical heavy chains (HC). LC Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H) or $V_H$) followed by a number of constant domains. Each light chain has a variable domain at one end (V(L) or $V_L$) and a constant domain at its other end; the constant domain of the light chain is aligned with the first constant domain of the heavy chain, and the light chain variable domain is aligned with the variable domain of the heavy chain. Particular amino acid residues are understood to form an interface between the light and heavy chain variable domains. The light chains of antibodies from any vertebrate species can be assigned to one of two clearly distinct types, called kappa (κ) and lambda (λ), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

In the context of antibodies and fragments thereof, the terms "variable region", "variable sequence", and the like, are used to describe certain portions of the variable domains that differ in sequence among antibodies and are used in the binding and specificity of each particular antibody for its particular antigen. However, the variability is not evenly distributed through the variable domains of antibodies. It is typically concentrated in three segments called complementarity determining regions (CDRs) or hypervariable (HV) regions both in the light chain and the heavy chain variable domains. The more highly conserved portions of the variable domains are called the framework (FR). The variable domains of native heavy and light chains each comprise four FR regions (FR1, FR2, FR3, and FR4), largely adopting a β-sheet configuration, connected by three CDRs (HV1, HV2, HV3), which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). CRDs are typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain (Kabat et al., *Sequences of Proteins of Immunological Interest,* 5th Ed. Public Health Service, National Institutes of Health, Bethesda, MD. (1991)). Residues that form core "hypervariable loops" are typically at approximately residues 26-32 (L1), 50-52 (L2) and 91-96 (L3) in the light chain variable domain and 26-32 (H1), 53-55 (H2) and 96-101 (H3) in the heavy chain variable domain (Chothia and Lesk, 1987, J. Mol. Biol. 196:901-917). The constant domains are not involved directly in binding an antibody to an antigen, but exhibit various effector functions, such as participation of the antibody in antibody-dependent cellular toxicity.

It is well-known that the variable regions of antibodies—and, in particular, the complementarity determining regions (CDRs) of the variable regions—are primarily responsible for the binding and binding specificity of antibodies. It is also well-known that portions of antibodies other than the variable regions (or other than the CDRs) can be substituted, altered, eliminated, etc. without abolishing the binding and binding specificity of the antibodies (or antibody fragments in the case of elimination of portions of the antibody). The well-known modular nature of antibody structure allows extensive substitution, alteration, elimination, etc. of portions of antibodies other than the variable regions (or other than the CDRs) while retaining the binding and binding specificity of the variable regions and CDRs. For example, the disclosed antibodies and antibody fragments can be in any form of antibody binding fragments that contains the CDR sequences of HCN2 and any form of antibody binding fragments that contains the CDR sequences of HCN3. Such principals have been amply demonstrated by production and use of chimeric antibodies, recombinant antibodies, humanized antibodies, and the numerous types of antibody fragments and antibody-derived polypeptides, such as $F(ab')_2$, fragment antigen-binding (Fab), half antibodies, single-chain variable fragments (scFv), VhH domain, V-NAR domain, VH domain, VL domain, $F(ab)_3$, bis-scFv, diabody, triabody, tetrabody, and minibody (Hollinger and Hudson, Nature Biotech. 23(9):1126-1136 (2005)(and references cited therein), Holliger & Winter, Proc. Natl. Acad. Sci. USA 90, 6444-6448 (1993); Pei et al., Proc. Natl. Acad. Sci. USA 94, 9637-9642 (1997); Iliades et al., FEBS Lett. 409, 437-441 (1997); De Genst et al., J. Biol. Chem. 280, 14114-14121 (2005); De Genst et al., J. Biol. Chem. 279, 53593-53601 (2004); Dooley & Flajnik, Eur. J. Immunol. 35, 936-945 (2005); Streltsov & Nuttall, Immunol. Lett. 97, 159-160 (2005); Streltsov et al., Proc. Natl. Acad. Sci. USA 101, 12444-12449 (2004); Cortez-Retamozo et al., Cancer Res. 64, 2853-2857 (2004); Dottorini et al., Biochemistry 43, 622-628 (2004); Colby et al., J. Mol. Biol. 342, 901-912 (2004); Jespers et al., J. Mol. Biol. 337, 893-903 (2004); Linsley, Nat. Immunol. 6, 231-232 (2005); 37. Casey et al., Br. J. Cancer 86, 1401-1410 (2002); Weir et al., Biochem. Soc. Trans. 30, 512-516 (2002); Dolezal et al., Protein Eng. 16, 47-56 (2003); Power et al., Methods Mol. Biol. 207, 335-350 (2003); Arndt et al., FEBS Lett. 578, 257-261 (2004); Griffiths et al., J. Nucl. Med. 45, 30-39 (2004); Olafsen et al., Protein Eng. Des. Sel. 17, 21-27 (2004); Wittel et al., Nucl. Med. Biol. 32, 157-164 (2005); Le Gall et al., Protein Eng. Des. Sel. 17, 357-366 (2004); Kenanova et al., Cancer Res. 65, 622-631 (2005); Adams et al., Cancer Res. 64, 6200-6206 (2004); Grosse-Hovest et al., Int. J. Cancer; published online 7 Jul. 2005 (interscience.wiley-.com/cgi-bin/abstract/110559371/ABSTRACT 120); Holliger et al., Cancer Res. 59, 2909-2916 (1999); Pattersen et al., J. Comput. Chem. 25, 1605-1612 (2004); Olafsen et al., Cancer Res. 65, 5907-5916 (2005); Shen et al., J. Nucl. Med. 46, 642-651 (2005); Nellis et al., Biotechnol. Prog. 21, 221-232 (2005); Ebbinghaus et al., Int. J. Cancer 116, 304-313 (2005); Wong et al., Clin. Cancer Res. 10, 5014-5021 (2004); Hulstein et al., Blood; published online 12 Jul. 2005 (bloodjournal.org/cgi/reprint/2005-03-1153v1)).

i. Chimeric Antibodies

The disclosure encompasses chimeric antibodies and hybrid antibodies, with dual or multiple antigen or epitope specificities, and fragments, such as F(ab')2 and the like, including hybrid fragments. Such antibodies and fragments can be made by techniques known in the art and can be screened for specificity and activity according to general methods for producing antibodies and screening antibodies for specificity and activity (see, e.g., Harlow and Lane. Antibodies, A Laboratory Manual. Cold Spring Harbor Publications, New York, (1988), which is hereby incorporated by reference).

The disclosure also encompasses human antibodies and/or humanized antibodies. Many non-human antibodies (e.g., those derived from mice, rats, or rabbits) are naturally antigenic in humans and, thus, can give rise to undesirable immune responses when administered to humans. Therefore, the use of human or humanized antibodies in the methods described herein serves to lessen the chance that an antibody administered to a human will evoke an undesirable immune response.

ii. Human Antibodies

Human, chimeric, or humanized derivatives of anti-human HCN1, HCN2, HCN3, and/or HCN4 antibodies are particularly preferred for in vivo use in humans, however, murine antibodies or antibodies of other species may be advantageously employed for many uses (for example, in vitro or in situ detection assays, acute in vivo use, etc.). A humanized antibody can comprise amino acid residue substitutions, deletions or additions in one or more non-human CDRs. The humanized antibody derivative may have substantially the same binding, stronger binding or weaker binding when compared to a non-derivative humanized antibody. In specific embodiments, one, two, three, four, or five amino acid residues of the CDR have been substituted, deleted or added (i.e., mutated). Completely human antibodies are particularly desirable for therapeutic treatment of human subjects.

Human antibodies can be made by a variety of methods known in the art including phage display methods described above using antibody libraries derived from human immunoglobulin sequences (see U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741). Human antibodies can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of an HCN1, HCN2, HCN3, and/or HCN4 polypeptide. Monoclonal antibodies directed against the antigen can be obtained from the immunized, transgenic mice using conventional hybridoma technology (see, e.g., U.S. Pat. No. 5,916,771). The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, CA) and Medarex (Princeton, NJ) can be engaged to provide human antibodies directed against a selected antigen using technology similar to that described above.

iii. Humanized Antibodies

A humanized or chimeric HCN1, HCN2, HCN3, and/or HCN4 antibody can include substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Preferably, an HCN1, HCN2, HCN3, and/or HCN4 antibody also includes at least a portion of an immunoglobulin constant region (Fc), typically that of a human immunoglobulin. The constant domains of the HCN1, HCN2, HCN3, and/or HCN4 antibodies may be selected with respect to the proposed function of the antibody, in particular the effector function which may be required. In some embodiments, the constant domains of the HCN1, HCN2, HCN3, and/or HCN4 antibodies are (or comprise) human IgA, IgD, IgE, IgG or IgM domains. In a specific embodiment, human IgG constant domains, especially of the IgG1 and IgG3 isotypes are used, when the humanized HCN1, HCN2, HCN3, and/or HCN4 antibodies is intended for therapeutic uses and antibody effector functions such as antibody-dependent cell-mediated cytotoxicity (ADCC) and complement-dependent cytotoxicity (CDC) activity are needed. In alternative embodiments, IgG2 and IgG4 isotypes are used when the HCN1, HCN2, HCN3, and/or HCN4 antibody is intended for therapeutic purposes and antibody effector function is not required. The invention encompasses Fe constant domains comprising one or more amino acid modifications which alter antibody effector functions such as those disclosed in U.S. Patent Application Publication Nos. 2005/0037000 and 2005/0064514.

In some embodiments, the HCN1, HCN2, HCN3, and/or HCN4 antibody contains both the light chain as well as at least the variable domain of a heavy chain. In other embodiments, the HCN1, HCN2, HCN3, and/or HCN4 antibody may further include one or more of the CH1, hinge, CH2, CH3, and CH4 regions of the heavy chain. The antibody can be selected from any class of immunoglobulins, including IgM, IgG, IgD, IgA and IgE, and any isotype, including IgG1, IgG2, IgG3 and IgG4. In some embodiments, the constant domain is a complement fixing constant domain where it is desired that the antibody exhibit cytotoxic activity, and the class is typically IgG1. In other embodiments, where such cytotoxic activity is not desirable, the constant domain may be of the IgG2 class. The HCN1, HCN2, HCN3, and/or HCN4 antibody may comprise sequences from more than one class or isotype, and selecting particular constant domains to optimize desired effector functions is within the ordinary skill in the art.

The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the donor antibody. Such mutations, however, are preferably not extensive. Usually, at least 75% of the humanized antibody residues will correspond to those of the parental framework region (FR) and CDR sequences, more often 90%, and most preferably greater than 95%. Humanized antibodies can be produced using variety of techniques known in the art, including, but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, *Molecular Immunology* 28(4/5):489-498; Studnicka et al., 1994, *Protein Engineering* 7(6):805-814; and Roguska et al., 1994, *Proc. Natl. Acad. Sci.* 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al., 2002, *J. Immunol.* 169:1119-25, Caldas et al., 2000, *Protein Eng.* 13:353-60, Morea et al., 2000, *Methods* 20:267-79, Baca et al., 1997, *J. Biol. Chem.* 272:10678-84, Roguska et al., 1996, *Protein Eng.* 9:895-904, Couto et al., 1995, *Cancer Res.* 55 (23 Supp):5973s-5977s, Couto et al., 1995, *Cancer Res.* 55:1717-22, Sandhu, 1994, *Gene* 150:409-10, Pedersen et al., 1994, *J. Mol. Biol.* 235:959-73, Jones et al., 1986, *Nature* 321:522-525, Riechmann et al., 1988, *Nature* 332:323, and Presta, 1992, *Curr. Op. Struct. Biol.* 2:593-596. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; U.S. Publication Nos. 2004/0049014 and 2003/0229208; U.S. Pat. Nos. 6,350,861; 6,180,370; 5,693,762; 5,693,761; 5,585,089; and 5,530,101 and Riechmann et al., 1988, Nature 332:323).

iv. Antibody Fragments

Embodiments of the disclosed antibodies that use the binding and binding specificity of the antibody (and do not require a particular biological function of the antibody constant regions) can comprise a binding fragment specific to HCN1, HCN2, HCN3, and/or HCN4. For antibody forms of the disclosed antibodies and polypeptides, the other antibody regions can be substituted, altered, or both, with or from any heavy and light chains or portions thereof, with the expectation that the bi-specific binding and binding specificity for HCN1, HCN2, HCN3, and/or HCN4 will be retained. For antibody fragment and peptide forms, the binding fragment specific to HCN1, HCN2, HCN3, and/or HCN4 can be embodied by any of numerous binding fragment forms and can be linked in any suitable way, including in any of the multivalent and multi-specific ways used for antibody binding fragments. In the case of the disclosed antibodies, antibody fragments, and polypeptides, such forms will be bi-specific instead of (or in addition to) multivalent. Examples of binding fragment forms include $F(ab')_2$, fragment antigen-binding (Fab), half antibodies, single-chain variable fragments (scFv), VhH domain, V-NAR domain, $V_H$ domain, $V_L$ domain, $F(ab)_3$, bis-scFv, diabody, triabody, tetrabody, and minibody. Any of these forms can be independently used to embody the binding fragment specific to HCN1, HCN2, HCN3, and/or HCN4 and then can be combined or joined using any suitable linker or coupling. The binding fragment specific to HCN1, HCN2, HCN3, and/or HCN4 can also each be used as a binding fragment portion of a multivalent and/or multi-specific form of antibody fragments. Examples include $F(ab')_2$, $F(ab)_3$, bis-scFv, diabody, triabody, tetrabody, and minibody.

3. Inhibitory Nucleic Acids

In some forms, the composition may include gene silencing compounds to reduce the expression or transcription of HCN1, HCN2, HCN3, and/or HCN4. Inhibitory nucleic acids can be used to target genomic HCN1, HCN2, HCN3, and/or HCN4, or target the expressed HCN1, HCN2, HCN3, and/or HCN4 nucleic acids (e.g., by targeting HCN1, HCN2, HCN3, and/or HCN4 mRNA). Inhibitory nucleic acids can be delivered to the cells via a vector. The vector may be a targeting moiety, a nucleic acid construct, a particle, a virus, a defective virus, an artificial chromosome, an artificial plasmid, or any combination thereof.

In some forms, the inhibitory nucleic acid specific to HCN1, HCN2, HCN3, and/or HCN4 is an inhibitory nucleic acid that silences gene expression.

In other forms, the inhibitory nucleic acid specific to HCN1, HCN2, HCN3, and/or HCN4 is an inhibitory nucleic acid that reduces the expression of HCN1, HCN2, HCN3, and/or HCN4.

In some forms, the inhibitory nucleic acid specific to HCN1, HCN2, HCN3, and/or HCN4 is a "pan" inhibitory nucleic acid silencing or reducing the expression of HCN1, HCN2, HCN3, and HCN4. In preferred embodiments, the inhibitory nucleic acid has a higher specificity to, or higher complementarity to, HCN2 compared to the specificity to, or complementarity to, HCN1 or HCN4. In other preferred embodiments, the inhibitory nucleic acid has a higher specificity to, or higher complementarity to, HCN3 compared to the specificity to, or complementarity to, HCN1 or HCN4. In other embodiments, the inhibitory nucleic acid has a higher specificity to, or higher complementarity to, HCN2 compared to the specificity to, or complementarity to, HCN3. In other embodiments, the inhibitory nucleic acid has a higher specificity to, or higher complementarity to, HCN3 compared to the specificity to, or complementarity to, HCN2.

The higher specificity, or complementarity, to an HCN isoform, such as to (i) HCN1, (ii) HCN2, (iii) HCN3, or (iv) HCN4, may be higher by at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 250%, about 300%, or about 350%, or more, when compared to specificity, or complementarity, to another HCN isoform, such as (i) HCN2, HCN3, or HCN4, (ii) HCN1, HCN3, or HCN4, (iii) HCN1, HCN2, or HCN4, and (iv) HCN1, HCN2, or HCN4, when measured by the same assay under the same environmental conditions.

Inhibitory nucleic acid technologies are known in the art and include, but are not limited to, antisense oligonucleotides, catalytic nucleic acids such as ribozymes and deoxyribozymes, aptamers, triplex forming nucleic acids, external guide sequences, and RNA interference molecules (RNAi), particularly small nucleic acid molecules, such as short interfering nucleic acid (siRNA), short interfering RNA (siRNA), double-stranded RNA (dsRNA), micro-RNA (mRNA), and short hairpin RNA (shRNA) molecules capable of mediating RNA interference (RNAi).

i. RNA Interference

Gene silencing by RNAi was originally observed with the addition of double stranded RNA (dsRNA) (Fire, A., et al. (1998) Nature, 391:806-11; Napoli, C., et al. (1990) Plant Cell 2:279-89; Hannon, G. J. (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, S. M., et al. (2001) Genes Dev., 15:188-200; Bernstein, E., et al. (2001) Nature, 409:363-6; Hammond, S. M., et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, A., et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, J., et al. (2002) Cell, 110:563-74). However, the effect of iRNA or siRNA or their use is not limited to any type of mechanism.

In some embodiments the inhibitory nucleic acid is an siRNA. SiRNA is typically a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. Sequence specific gene or isoform specific silencing can be achieved in mammalian cells using synthetic, short double-stranded RNAs that mimic the siRNAs produced by the enzyme dicer (Elbashir, S. M., et al. (2001) Nature, 411:494-498) (Ui-Tei, K., et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Texas), ChemGenes (Ashland, Massachusetts), Dharmacon (Lafayette, Colorado), Glen Research (Sterling, Virginia), MWB Biotech (Esbersberg, Germany), Proligo (Boulder, Colorado), and Qiagen (Vento, The Netherlands). siRNA can also be synthesized in vitro using kits such as Ambion's SILENCER® siRNA Construction Kit.

Small RNAs include microRNAs (miRNA) and small interfering RNAs (siRNAs). MiRNAs are produced by the cleavage of short stem-loop precursors by Dicer-like enzymes; whereas, siRNAs are produced by the cleavage of long double-stranded RNA molecules. MiRNAs are single-stranded, whereas siRNAs are double-stranded. Therefore, the double-stranded structure may be formed by a single self-complementary RNA strand or two separate complementary RNA strands. RNA duplex formation may be initiated either inside or outside the plant cell.

Suitable inhibitory nucleic acids can contain one or more modified bases, or have a modified backbone to increase stability or for other reasons. For example, the phosphodiester linkages of natural RNA may be modified to include at least one of a nitrogen or sulfur heteroatom. Moreover, nucleic acids comprising unusual bases, such as inosine, or modified bases, such as tritylated bases, to name just two examples, can be used. It will be appreciated that a great variety of modifications have been made to nucleic acids that serve many useful purposes. The term nucleic acids as it is employed herein embraces such chemically, enzymatically or metabolically modified forms of nucleic acids, provided that it is derived from an endogenous template.

The sequence of at least one strand of the RNAi molecule contains a region complementary to at least a part of the target mRNA sufficient for the RNAi molecule to specifically hybridize to the target mRNA. In one embodiment, one strand of the RNAi molecule is substantially identical to at least a portion of the target mRNA.

In one embodiment, the inhibitory nucleic acid has 100% sequence identity with at least a part of the target mRNA transcribed from HCN1, HCN2, HCN3, or HCN4 genes. However, inhibitory nucleic acids having 70%, 80% or greater than 90% or 95% sequence identity may be used. Thus sequence variations that might be expected due to genetic mutation, strain polymorphism, or evolutionary divergence can be tolerated.

RNAi molecules includes small RNA molecules which are single stranded or double stranded RNA molecules generally less than 200 nucleotides in length. Such molecules are generally less than 100 nucleotides and usually vary from 10 to 100 nucleotides in length. The duplex region of a double stranded RNA may have a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing). While the optimum length of the double stranded RNA may vary according to the target sequence and experimental conditions, the duplex region of the RNA may be at least 19, 20, 21, 22, 23, 25, 50, 100, 200, 300, 400 or more nucleotides long. In a preferred format, small RNA molecules, such as siRNA and shRNA have 11, 12, 13, 14, 15, 16, 17, 18, 19, 20, 21, 22, 23, 24, 25, 26, 27, 28, 29 or 30 nucleotides. Preferably, the nucleotides are contiguous, consecutive nucleotides of complementary to a target mRNA sequence, for example HCN2 mRNA.

The mature antisense sequences for targeting HCN2 mRNA may be: 5'-TCATGCTGAGCATGGTCAG-3' (SEQ ID NO: 1); 5'-TCTTCTTGATCTTCTCGGG-3' (SEQ ID NO: 2); and 5'-AGTCGTGGATCTTCTGGCG-3' (SEQ ID NO: 3).

In vivo, the RNAi molecule may be synthesized using recombinant techniques well known in the art (see e.g., Sambrook, et al., Molecular Cloning; A Laboratory Manual, Third Edition (2001)). For example, bacterial cells can be transformed with an expression vector which comprises the DNA template from which double stranded RNA is to be derived. Alternatively, the cells in which inhibition of gene or isoform expression is desired may be transformed with an expression vector or by other means. Bidirectional transcription of one or more copies of the template may be by endogenous RNA polymerase of the transformed cell or by a cloned RNA polymerase (e.g., T3, T7, SP6) coded for by the expression vector or a different expression vector. Inhibition of gene or isoform expression may be targeted by specific transcription in an organ, tissue, or cell type; an environmental condition (e.g. temperature, chemical); and/or engineering transcription at a developmental stage or age, especially when the RNAi molecule is synthesized in vivo. RNAi molecules may also be delivered to specific tissues or cell types using known gene delivery systems. The production of siRNA from a vector is commonly done through the transcription of a short hairpin RNAs (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors.

ii. Aptamers

In some forms, a compound that reduces the expression of HCN1, HCN2, HCN3, and/or HCN4 is an aptamer. Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules as well as large molecules, such as reverse transcriptase. Aptamers can bind very tightly with $K_d$s from the target molecule of less than 10–12 M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a $K_d$ with the target molecule at least 10, 100, 1000, 10,000, or 100,000 fold lower than the $K_d$ with a background binding molecule. It is preferred when doing the comparison for a polypeptide for example, that the background molecule be a different polypeptide. Representative examples of how to make and use aptamers to bind a variety of different target molecules are known in the art.

iii. Ribozymes

In some forms, a compound that reduces the expression of HCN1, HCN2, HCN3, and/or HCN4 is a ribozyme. Ribozymes are nucleic acid molecules that are capable of catalyzing a chemical reaction, either intramolecularly or intermolecularly. Ribozymes are thus catalytic nucleic acids. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Examples of how to make and use ribozymes to catalyze a variety of different reactions are known in the art.

iv. Triplex Forming Nucleic Acids

In some forms a compound that reduces the expression of HCN1, HCN2, HCN3, and/or HCN4 is triplex forming nucleic acids. Triplex forming nucleic acid molecules are molecules that can interact with either double-stranded or single-stranded nucleic acid. When triplex molecules interact with a target region, a structure called a triplex is formed, in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$, $10^{-8}$, $10^{-10}$, or $10^{-12}$. Examples of how to make and use triplex forming molecules to bind a variety of different target molecules are known in the art.

v. External Guide Sequences

In some forms a compound that reduces the expression of HCN1, HCN2, HCN3, and/or HCN4 is external guide sequences (EGSs). EGSs are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukaryotic cells. Examples of how to make and use EGS molecules to facilitate cleavage of a variety of different target molecules are known in the art.

D. Pharmaceutical Compositions

The compositions described herein may form pharmaceutical compositions when combined with a pharmaceutically acceptable excipient and/or carrier.

Pharmaceutically acceptable excipients include compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration. Pharmaceutically acceptable excipients include, but are not limited to, diluents, preservatives, binders, lubricants, disintegrators, swelling agents, fillers, stabilizers, and combinations thereof.

1. Excipients

Excipients may be chosen based on the application of the composition, as would be understood by those of skill in the art. Suitable excipients include surfactants, emulsifiers, emulsion stabilizers, anti-oxidants, emollients, humectants, chelating agents, suspending agents, thickening agents, occlusive agents, preservatives, stabilizing agents, pH modifying agents, solubilizing agents, solvents, flavoring agents, and other excipients.

Suitable emulsifiers include, but are not limited to, straight chain or branched fatty acids, polyoxyethylene sorbitan fatty acid esters, sorbitan fatty acid esters, propylene glycol stearate, glyceryl stearate, polyethylene glycol, fatty alcohols, polymeric ethylene oxide-propylene oxide block copolymers, and combinations thereof.

Suitable surfactants include, but are not limited to, anionic surfactants, non-ionic surfactants, cationic surfactants, and amphoteric surfactants.

Suitable suspending agents include, but are not limited to, alginic acid, bentonite, carbomer, carboxymethylcellulose and salts thereof, colloidal oatmeal, hydroxyethylcellulose, hydroxypropylcellulose, microcrystalline cellulose, colloidal silicon dioxide, dextrin, gelatin, guar gum, xanthan gum, kaolin, magnesium aluminum silicate, maltitol, triglycerides, methylcellulose, polyoxyethylene fatty acid esters, polyvinylpyrrolidone, propylene glycol alginate, sodium alginate, sorbitan fatty acid esters, tragacanth, and combinations thereof.

Suitable antioxidants include, but are not limited to, butylated hydroxytoluene, alpha tocopherol, ascorbic acid, fumaric acid, malic acid, butylated hydroxyanisole, propyl gallate, sodium ascorbate, sodium metabisulfite, ascorbyl palmitate, ascorbyl acetate, ascorbyl phosphate, Vitamin A, folic acid, flavons or flavonoids, histidine, glycine, tyrosine, tryptophan, carotenoids, carotenes, alpha-Carotene, beta-Carotene, uric acid, pharmaceutically acceptable salts thereof, derivatives thereof, and combinations thereof.

Suitable chelating agents include, but are not limited to, ammonium citrate, ammonium oxalate monohydrate, citric acid, tartaric acid, potassium oxalate, ethylenediaminetetraacetic acid (EDTA), and combinations thereof.

Suitable humectants include, but are not limited to, glycerin, butylene glycol, propylene glycol, sorbitol, triacetin, and combinations thereof.

Preservatives can be used to prevent the growth of fungi and other microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetypyridinium chloride, chlorobutanol, phenol, phenylethyl alcohol, thimerosal, and combinations thereof.

Excipients may include suspending agents such as sterile water, phosphate buffered saline, saline, or a non-aqueous solution such as glycerol.

2. Carriers

Any of the compositions can be used therapeutically in combination with a pharmaceutically acceptable carrier. The compounds described herein can be conveniently formulated into pharmaceutical compositions composed of one or more of the compounds in association with a pharmaceutically acceptable carrier. See, e.g., *Remington's Pharmaceutical Sciences*, latest edition, by E. W. Martin Mack Pub. Co., Easton, PA, which discloses typical carriers and conventional methods of preparing pharmaceutical compositions that can be used in conjunction with the preparation of formulations of the compounds described herein and which is incorporated by reference herein. These most typically would be standard carriers for administration of compositions to humans. In one aspect, humans and non-humans, including solutions such as sterile water, saline, and buffered solutions at physiological pH. Other compounds will be administered according to standard procedures used by those skilled in the art.

The pharmaceutical compositions described herein can include, but are not limited to, carriers, thickeners, diluents, buffers, preservatives, surface active agents and the like in addition to the molecule of choice.

The skilled person can select the appropriate carrier based on the desired use. For example, in some embodiments the carrier can be polyethylene glycol, polypropylene glycol, a mixture or polymer of sugars (lactose, sucrose, dextrose, etc.), salts, poloxamers, hydroxypropylcellulose, polyvinyl alcohol, other water-soluble food grade excipients, or even other excipients.

3. Pharmaceutical Composition Forms

The composition may be in any suitable form, such as a liquid, cream, gel, foam, solid (e.g. tablet or capsule), pellets, strips, concentrated powders, concentrated liquids, and the like.

Preparations for parenteral administration include sterile aqueous or non-aqueous solutions, suspensions, and emulsions which can also contain buffers, diluents and other suitable additives. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Compositions for oral administration can include powders or granules, suspensions or solutions in water or non-aqueous media, capsules, sachets, or tablets. Thickeners, flavorings, diluents, emulsifiers, dispersing aids or binders can be desirable.

For example, the compositions may be compressed into tablets, optionally with a suitable binder and/or other excipients. Optionally, the tablet is coated with a material such as an enteric coating, e.g. EUDRAGIT®, to prevent release of the compositions until after passage through the stomach.

In some embodiments, the composition is in the form of a capsule. Optionally, the composition is encapsulated in hard or soft gels, such as gelatin and alginate capsules or enteric formulated soft gels.

In some embodiments, the pharmaceutical composition is in a form suitable for administration to mucosal surfaces, such as the mouth, nasal cavity, oral cavity, pulmonary system, rectal or vaginal surfaces.

The pharmaceutical compositions may be provided for oral administration, systemic administration, such as intravenous administration, intramuscular administration, subcutaneous administration, or parenteral administration. The pharmaceutical compositions may be provided for local administration, such as for topical administration, buccal administration, intratumor administration, intraocular administration, or intracerebroventricular administration.

The administration may be by injection, ingestion, spraying, coating, smearing, brushing, and other suitable means.

The pharmaceutical compositions can be administered to the subject in a number of ways depending on whether local or systemic treatment is desired, and on the area to be treated. Thus, for example, a compound or pharmaceutical composition described herein can be administered as an ophthalmic solution and/or ointment to the surface of the eye. Moreover, a pharmaceutical composition can be administered to a subject vaginally, rectally, intranasally, orally, by inhalation, or parenterally, for example, by intradermal, subcutaneous, intramuscular, intraperitoneal, intrarectal, intraarterial, intralymphatic, intravenous, intrathecal and intratracheal routes. Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

4. Pharmaceutical Compositions for Targeted Delivery

The pharmaceutical compositions may be delivered to the tumor site by passive delivery or targeted delivery. Passive delivery typically includes delivery via blood circulation. Targeted delivery typically uses targeting means, such as targeting moieties.

Any of the compositions disclose herein may be linked with a targeting moiety to form a tumor targeting composition.

i. Targeting Moieties

The compositions can be modified to facilitate targeting through the attachment of targeting molecules. Exemplary target molecules include proteins, peptides, nucleic acids, lipids, saccharides, or polysaccharides, or small molecules that bind to one or more targets associated with an organ, tissue, cell, or extracellular matrix, or specific type of tumor or infected cell. The degree of specificity with which the compositions are targeted can be modulated through the selection of a targeting molecule with the appropriate affinity and specificity. For example, a targeting moiety can be a polypeptide, such as an antibody that specifically recognizes a tumor marker that is present exclusively or in higher amounts on a malignant cell (e.g., a tumor antigen). Suitable targeting molecules that can be used to direct the compositions to cells and tissues of interest, as well as methods of conjugating target molecules to compositions, are known in the art. Targeting molecules can also include neuropilins and endothelial targeting molecules, integrins, selectins, and adhesion molecules.

Targeting molecules can be covalently bound to compositions using a variety of methods known in the art. In some embodiments, the targeting moieties are covalently associated with the compositions, preferably via a linker cleaved at the site of delivery.

Examples of targeting moieties include peptides such as iRGD, LyP1; small molecule such as folate, aptamers and antibodies or their combinations at various molar ratios.

The targeting moiety should have an affinity for a cell-surface receptor or cell-surface antigen on the target cells and result in internalization of the composition within the target cell.

The targeting element can specifically recognize and bind to a target molecule specific for a cell type, a tissue type, or an organ. The target molecule can be a cell surface polypeptide, lipid, or glycolipid. The target molecule can be a receptor that is selectively expressed on a specific cell surface, a tissue or an organ. Cell specific markers can be for specific types of cells including, but not limited to stem cells, blood cells, immune cells, muscle cells, nerve cells, cancer cells, virally infected cells, and organ specific cells. The cell markers can be specific for endothelial, ectodermal, or mesenchymal cells. Representative cell specific markers include, but are not limited to cancer specific markers.

Additional targets that can be recognized by the targeting element include VEGF/KDR, Tie2, vascular cell adhesion molecule (VCAM), endoglin and $\alpha_5\beta_3$ integrin/vitronectin.

a. Tumor-Specific and Tumor-Associated Antigens

In one embodiment the targeting moiety specifically binds to an antigen that is expressed by tumor cells. The antigen expressed by the tumor may be specific to the tumor, or may be expressed at a higher level on the tumor cells as compared to non-tumor cells. Antigenic markers such as serologically defined markers known as tumor associated antigens, which are either uniquely expressed by cancer cells or are present at markedly higher levels (e.g., elevated in a statistically significant manner) in subjects having a malignant condition relative to appropriate controls, are contemplated for use in certain embodiments.

Tumor-associated antigens may include, for example, cellular oncogene-encoded products or aberrantly expressed proto-oncogene-encoded products (e.g., products encoded by the neu, ras, trk, and kit genes), or mutated forms of growth factor receptor or receptor-like cell surface molecules (e.g., surface receptor encoded by the c-erb B gene). Other tumor-associated antigens include molecules that may be directly involved in transformation events, or molecules that may not be directly involved in oncogenic transformation events but are expressed by tumor cells (e.g., carcinoembryonic antigen, CA-125, melanoma associated antigens, etc.) (see, e.g., U.S. Pat. No. 6,699,475; Jager, et al., *Int. J. Cancer,* 106:817-20 (2003); Kennedy, et al., *Int. Rev. Immunol.,* 22:141-72 (2003); Scanlan, et al. *Cancer Immun.,* 4:1 (2004)).

Genes that encode cellular tumor associated antigens include cellular oncogenes and proto-oncogenes that are aberrantly expressed. In general, cellular oncogenes encode products that are directly relevant to the transformation of the cell, and because of this, these antigens are particularly preferred targets for immunotherapy. An example is the tumorigenic neu gene that encodes a cell surface molecule involved in oncogenic transformation. Other examples include the ras, kit, and trk genes. The products of proto-oncogenes (the normal genes which are mutated to form oncogenes) may be aberrantly expressed (e.g., overexpressed), and this aberrant expression can be related to cellular transformation. Thus, the product encoded by proto-oncogenes can be targeted. Some oncogenes encode growth factor receptor molecules or growth factor receptor-like molecules that are expressed on the tumor cell surface. An example is the cell surface receptor encoded by the c-erbB gene. Other tumor-associated antigens may or may not be directly involved in malignant transformation. These antigens, however, are expressed by certain tumor cells and may therefore provide effective targets. Some examples are carcinoembryonic antigen (CEA), CA 125 (associated with ovarian carcinoma), and melanoma specific antigens.

In ovarian and other carcinomas, for example, tumor associated antigens are detectable in samples of readily obtained biological fluids such as serum or mucosal secretions. One such marker is CA125, a carcinoma associated antigen that is also shed into the bloodstream, where it is detectable in serum (e.g., Bast, et al., *N. Eng. J. Med.,* 309:883 (1983); Lloyd, et al., *Int. J. Canc.,* 71:842 (1997). CA125 levels in serum and other biological fluids have been measured along with levels of other markers, for example, carcinoembryonic antigen (CEA), squamous cell carcinoma antigen (SCC), tissue polypeptide specific antigen (TPS), sialyl TN mucin (STN), and placental alkaline phosphatase (PLAP), in efforts to provide diagnostic and/or prognostic profiles of ovarian and other carcinomas (e.g., Sarandakou, et al., *Acta Oncol.,* 36:755 (1997); Sarandakou, et al., *Eur. J. Gynaecol. Oncol.,* 19:73 (1998); Meier, et al., *Anticancer Res.,* 17(4B):2945 (1997); Kudoh, et al., *Gynecol. Obstet. Invest.,* 47:52 (1999)). Elevated serum CA125 may also accompany neuroblastoma (e.g., Hirokawa, et al., *Surg. Today,* 28:349 (1998), while elevated CEA and SCC, among others, may accompany colorectal cancer (Gebauer, et al., *Anticancer Res.,* 17(4B):2939 (1997)).

The tumor associated antigen, mesothelin, defined by reactivity with monoclonal antibody K-1, is present on a majority of squamous cell carcinomas including epithelial ovarian, cervical, and esophageal tumors, and on mesotheliomas (Chang, et al., *Cancer Res.,* 52:181 (1992); Chang, et al., *Int. J. Cancer,* 50:373 (1992); Chang, et al., *Int. J. Cancer,* 51:548 (1992); Chang, et al., *Proc. Natl. Acad. Sci. USA,* 93:136 (1996); Chowdhury, et al., *Proc. Natl. Acad. Sci. USA,* 95:669 (1998)). Using MAb K-1, mesothelin is detectable only as a cell-associated tumor marker and has not been found in soluble form in serum from ovarian cancer patients, or in medium conditioned by OVCAR-3 cells (Chang, et al., *Int. J. Cancer,* 50:373 (1992)). Structurally related human mesothelin polypeptides, however, also include tumor-associated antigen polypeptides such as the distinct mesothelin related antigen (MRA) polypeptide, which is detectable as a naturally occurring soluble antigen in biological fluids from patients having malignancies (see WO 00/50900).

A tumor antigen may include a cell surface molecule. Tumor antigens of known structure and having a known or described function, include the following cell surface receptors: HER1 (GenBank Accession No. U48722), HER2 (Yoshino, et al., *J. Immunol.,* 152:2393 (1994); Disis, et al., Canc. Res., 54:16 (1994); GenBank Acc. Nos. X03363 and M17730), HER3 (GenBank Acc. Nos. U29339 and M34309), HER4 (Plowman, et al., *Nature,* 366:473 (1993); GenBank Acc. Nos. L07868 and T64105), epidermal growth factor receptor (EGFR) (GenBank Acc. Nos. U48722, and K03193), vascular endothelial cell growth factor (GenBank No. M32977), vascular endothelial cell growth factor receptor (GenBank Acc. Nos. AF022375, 1680143, U48801 and X62568), insulin-like growth factor-I (GenBank Acc. Nos. X00173, X56774, X56773, X06043, European Patent No. GB 2241703), insulin-like growth factor-II (GenBank Acc. Nos. X03562, X00910, M17863 and M17862), transferrin receptor (Trowbridge and Omary, *Proc. Nat. Acad. USA,* 78:3039 (1981); GenBank Acc. Nos. X01060 and M11507), estrogen receptor (GenBank Acc. Nos. M38651, X03635, X99101, U47678 and M12674), progesterone receptor (GenBank Acc. Nos. X51730, X69068 and M15716), follicle stimulating hormone receptor (FSH-R) (GenBank Acc. Nos. Z34260 and M65085), retinoic acid receptor (GenBank Acc. Nos. L12060, M60909, X77664, X57280, X07282 and X06538), MUC-1 (Barnes, et al., *Proc. Nat. Acad. Sci. USA,* 86:7159 (1989); GenBank Acc. Nos. M65132 and M64928), NY-ESO-1 (GenBank Acc. Nos. AJ003149 and U87459), NA 17-A (PCT Publication No. WO 96/40039), Melan-A/MART-1 (Kawakami, et al., *Proc. Nat. Acad. Sci. USA,* 91:3515 (1994); GenBank Ace. Nos. U06654 and U06452), tyrosinase (Topalian, et al., *Proc. Nat. Acad. Sci. USA,* 91:9461 (1994); GenBank Acc. No. M26729; Weber, et al., *J. Clin. Invest,* 102:1258 (1998)), Gp-100 (Kawakami, et al., *Proc. Nat. Acad. Sci. USA,* 91:3515 (1994); GenBank Acc. No. S73003, Adema, et al., *J. Biol. Chem.,* 269:20126 (1994)), MAGE (van den Bruggen, et al., *Science,* 254:1643 (1991)); GenBank Ace. Nos. U93163, AF064589, U66083, D32077, D32076, D32075, U10694, U10693, U10691, U10690, U10689, U10688, U10687, U10686, U10685, L18877, U10340, U10339, L18920, U03735 and M77481), BAGE (GenBank Acc. No. U19180; U.S. Pat. Nos. 5,683,886 and 5,571,711), GAGE (GenBank Acc. Nos. AF055475, AF055474, AF055473, U19147, U19146, U19145, U19144, U19143 and U19142), any of the CTA class of receptors including in particular HOM-MEL-40 antigen encoded by the SSX2 gene (GenBank Acc. Nos. X86175, U90842, U90841 and X86174), carcinoembryonic antigen (CEA, Gold and Freedman, *J. Exp. Med.,* 121:439 (1985); GenBank Acc. Nos. M59710, M59255 and M29540), and PyLT (GenBank Acc. Nos. J02289 and J02038); p97 (melanotransferrin) (Brown, et al., *J. Immunol.,* 127:539-46 (1981); Rose, et al., *Proc. Natl. Acad. Sci. USA,* 83:1261-61 (1986)).

Additional tumor associated antigens include prostate surface antigen (PSA) (U.S. Pat. Nos. 6,677,157; 6,673,545); β-human chorionic gonadotropin (β-HCG) (McManus, et al., *Cancer Res.,* 36:3476-81 (1976); Yoshimura, et al., *Cancer,* 73:2745-52 (1994); Yamaguchi, et al., *Br. J. Cancer,* 60:382-84 (1989): Alfthan, et al., *Cancer Res.,* 52:4628-33 (1992)); glycosyltransferase β-1,4-N-acetylgalactosaminyltransferases (GalNAc) (Hoon, et al., *Int. J. Cancer,* 43:857-62 (1989); Ando, et al., *Int. J. Cancer,* 40:12-17 (1987); Tsuchida, et al., *J. Natl. Cancer,* 78:45-54 (1987); Tsuchida, et al., *J. Natl. Cancer,* 78:55-60 (1987)); NUC18 (Lehmann, et al., *Proc. Natl. Acad. Sci. USA,* 86:9891-95 (1989); Lehmann, et al., *Cancer Res.,* 47:841-45 (1987)); melanoma antigen gp75 (Vijayasardahi, et al., *J. Exp. Med.,* 171:1375-80 (1990); GenBank Accession No. X51455); human cytokeratin 8; high molecular weight melanoma antigen (Natali, et al., *Cancer,* 59:55-63 (1987); keratin 19 (Datta, et al., *J. Clin. Oncol.,* 12:475-82 (1994)).

Tumor antigens also include antigens regarded in the art as "cancer/testis" (CT) antigens that are immunogenic in subjects having a malignant condition (Scanlan, et al., *Cancer Immun.,* 4:1 (2004)). CT antigens include at least 19 different families of antigens that contain one or more members and that are capable of inducing an immune response, including but not limited to MAGEA (CT1); BAGE (CT2); MAGEB (CT3); GAGE (CT4); SSX (CT5); NY-ESO-1 (CT6); MAGEC (CT7); SYCP1 (C8); SPANXB1 (CT11.2); NA88 (CT18); CTAGE (CT21); SPA17 (CT22); OY-TES-1 (CT23); CAGE (CT26); HOM- TES-85 (CT28); HCA661 (CT30); NY-SAR-35 (CT38); FATE (CT43); and TPTE (CT44).

Additional tumor antigens that can be targeted, including a tumor-associated or tumor-specific antigen, include, but not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triosephosphate isomeras, Bage-1, Gage 3,4, 5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Hom/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS. Other tumor-associated and tumor-specific antigens are known to those of skill in the art and are suitable for targeting by the fusion proteins.

b. Peptide Targeting Elements

The targeting element can be a peptide. Specifically, the targeting peptide can be, but is not limited to, one or more of the following: RGD, iRGD (CRGD[K/R]GP[D/E]C), LyP-1, P3 (CKGGRAKDC), or their combinations at various molar ratios. The targeting peptides can be covalently associated with the composition and the covalent association can be mediated by a linker.

c. Antibody Targeting Elements

The targeting element can be an antibody or an antigen-binding fragment thereof. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. The antigen binding portion of the antibody can be any portion that has at least one antigen binding site, such as Fab, $F(ab')_2$, dsFv, sFv, diabodies, and triabodies. In certain embodiments, the antibody is a single chain antibody.

d. Aptamer Targeting Elements

Aptamers are oligonucleotide or peptide sequences with the capacity to recognize virtually any class of target molecules with high affinity and specificity. Aptamers bind to targets such as small organics, peptides, proteins, cells, and tissues. Unlike antibodies, some aptamers exhibit stereoselectivity. The aptamers can be designed to bind to specific targets expressed on cells, tissues or organs.

E. Methods of Making the Compositions

Methods of making the compositions described herein are generally known in the art. Typically, the methods described herein include chemical synthesis and purification methods, molecular biology methods, biochemical methods, or combinations thereof, to produce and verify the compositions.

1. Synthesis of Ivabradine and its Derivatives

Methods of synthesis of ivabradine are known in the art and include catalytic hydrogenation. An exemplary method for synthesizing ivabradine is described in U.S. Pat. No. 7,176,197 B2.

2. Methods of Making Antibodies

The disclosed antibodies, fragments, and polypeptides can be produced by any method known in the art useful for the production of polypeptides, e.g., in vitro synthesis, recombinant DNA production, and the like. The antibodies may be produced by recombinant DNA technology. The HCN1, HCN2, HCN3, and/or HCN4 antibodies can be produced using recombinant immunoglobulin expression technology. The recombinant production of immunoglobulin molecules, including humanized antibodies are described in U.S. Pat. No. 4,816,397 (Boss et al.), U.S. Pat. Nos. 6,331,415 and 4,816,567 (both to Cabilly et al.), U.K. patent GB 2,188,638 (Winter et al.), and U.K. patent GB 2,209,757. Techniques for the recombinant expression of immunoglobulins, including humanized immunoglobulins, can also be found, in Goeddel et al., Gene Expression Technology Methods in Enzymology Vol. 185 Academic Press (1991), and Borreback, Antibody Engineering, W. H. Freeman (1992). Additional information concerning the generation, design and expression of recombinant antibodies can be found in Mayforth, Designing Antibodies, Academic Press, San Diego (1993).

The antibodies may also be produced by immunizing animals with synthetic or purified monomeric, homomeric, or heteromeric HCN1, HCN2, HCN3, and/or HCN4. The immune sera are applied to a peptide affinity column to generate a highly specific immunoreagent.

The human antibodies and humanized antibodies described herein can be prepared by any known technique. Examples of techniques for human monoclonal antibody production include those described by Boerner et al., J. Immunol., 147(1), 86-95 (1991), which is hereby incorporated by reference. Human antibodies described herein (and fragments thereof) can also be produced using phage display libraries (see, e.g., Marks et al., J. Mol. Biol., 222, 581-597 (1991)), which is hereby incorporated by reference. The human antibodies described herein can also be obtained from transgenic animals. For example, transgenic mutant mice that are capable of producing a full repertoire of human antibodies in response to immunization have been described (see, e.g., Jakobovits et al., PNAS, 90, 2551-255 (1993); and Jakobovits et al., Nature, 362, 255-258 (1993)), all of which are hereby incorporated by reference.

Methods for humanizing non-human antibodies are known in the art. For example, humanized antibodies can be generated by substituting rodent complementarity-determining regions (CDRs) or CDR sequences for the corresponding sequences of a human antibody. Detailed procedures are disclosed in Jones et al., Nature, 321, 522-525 (1986); Riechmann et al., Nature, 332, 323-327 (1988); Verhoeyen et al., Science, 239, 1534-1536 (1988), all of which are hereby incorporated by reference.

Methods that can be used to produce humanized antibodies are also described in U.S. Pat. Nos. 4,816,567; 5,565,332; 5,721,367; 5,837,243; 5,939,598; 6,130,364; and 6,180,377; all of which are hereby incorporated by reference.

3. Methods of Making Inhibitory Nucleic Acids

Isolated nucleic acid molecules can be produced by standard techniques, including, without limitation, common molecular cloning and chemical nucleic acid synthesis techniques. For example, polymerase chain reaction (PCR) techniques can be used to obtain an isolated nucleic acid encoding a polypeptide. PCR is a technique in which target nucleic acids are enzymatically amplified.

When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292-1293.

Isolated nucleic acids can be chemically synthesized, either as a single nucleic acid molecule or as a series of oligonucleotides (e.g., using phosphoramidite technology for automated DNA synthesis in the 3' to 5' direction). For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase can be used to extend the oligonucleotides, resulting in a single, double-stranded nucleic acid molecule per oligonucleotide pair, which then can be ligated into a vector. Isolated nucleic acids can also obtained by mutagenesis. Nucleic acids can be mutated using standard techniques, including oligonucleotide-directed mutagenesis and/or site-directed mutagenesis through PCR. See, Short Protocols in Molecular Biology. Chapter 8, Green Publishing Associates and John Wiley & Sons, edited by Ausubel et al, 1992.

4. Methods Testing Binding Specificity to and Inhibition of HCN

The binding of the compositions to HCN1, HCN2, HCN3, and/or HCN4 can be detected using routine methods, such as immunodetection methods, that do not disturb protein binding. The methods can be cell-based or cell-free assays. Immunoassays, in their most simple and direct sense, are binding assays involving binding between antibodies and antigen. Many types and formats of immunoassays are known and all are suitable for detecting binding to, or inhibition of, any of HCH1, HCN2, HCN3, and/or HCN4. Examples include electrophysiological assays, immunoassays, such as enzyme linked immunosorbent assays (ELISAs), radioimmunoassays (RIA), radioimmune precipitation assays (RIPA), immunobead capture assays, Western blotting, dot blotting, gel-shift assays, flow cytometry, protein arrays, multiplexed bead arrays, magnetic capture, in vivo imaging, fluorescence resonance energy transfer (FRET), and fluorescence recovery/localization after photobleaching (FRAP/FLAP).

F. Pharmaceutical Compositions for Controlled Release

The pharmaceutical composition described herein can be formulated for controlled release including immediate release, delayed release, extended release, pulsatile release, and combinations thereof.

1. Nano- and Microparticles

The one or more compositions, and optional one or more additional active agents, can be incorporated into microparticles, nanoparticles, or combinations thereof that provide controlled release of the compounds and/or one or more additional active agents. In forms wherein the formulations contains two or more compositions, the compositions can be formulated for the same type of controlled release (e.g., delayed, extended, immediate, or pulsatile) or the compositions can be independently formulated for different types of release (e.g., immediate and delayed, immediate and extended, delayed and extended, delayed and pulsatile, etc.).

For example, the compositions and/or one or more additional active agents can be incorporated into polymeric microparticles, which provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers, which are slowly soluble and form a gel in an aqueous environment, such as hydroxypropyl methylcellulose or polyethylene oxide, can also be suitable as materials for drug containing microparticles. Other polymers include, but are not limited to; polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl, stearyl, cetyl, or cetostearyl alcohol), fatty acids and derivatives, including but not limited to fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material, which is normally solid at room temperature and has a melting point of from about 30 to 300° C.

In some cases, it may be desirable to alter the rate of water penetration into the microparticles. To this end, rate-controlling (wicking) agents can be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropylcellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins, which are water insoluble, such as zein, can also be used as materials for the formation of drug containing microparticles. Additionally, proteins, polysaccharides and combinations thereof, which are water-soluble, can be formulated with drug into microparticles and subsequently cross-linked to form an insoluble network. For example, cyclodextrins can be complexed with individual drug molecules and subsequently cross-linked.

Every compound within the above definition is intended to be and should be considered to be specifically disclosed herein. Further, every subgroup that can be identified within the above definition is intended to be and should be considered to be specifically disclosed herein. As a result, it is specifically contemplated that any compound, or subgroup of compounds can be either specifically included for or excluded from use or included in or excluded from a list of compounds.

G. Methods of Using the Compositions

The compositions described herein are useful in treating proliferative diseases, such as benign or malignant tumors. Typically, the compositions are used to treat cancer.

1. Cancers to be Treated

Typically, the cancers to be treated have cancer cells, tumor cells, and/or cancer stem cells that overexpress any one or all of the genes for HCN1, HCN2, HCN3, and HCN4. In some embodiments the cancers to be treated are breast cancer, including triple-negative breast cancer, lung cancer, including non-small cell lung cancer and small cell lung cancer, cervical cancer, and brain cancer, including glioma and glioblastoma.

Examples of cancers to be treated include, but are not limited to Leukemia, AIDS-Related Cancers Kaposi Sarcoma, AIDS-Related Lymphoma, Lymphoma, Astrocytomas, Basal Cell Carcinoma, Bile Duct Cancer, Bladder Cancer, Bone, Brain Tumors, Breast Cancer, Bronchial Tumors, Burkitt Lymphoma, Cardiac (Heart) Tumors, Cervical Cancer, Chronic Myeloproliferative Neoplasms, Colorectal Cancer, Embryonal Tumors, Endometrial Cancer, Ependymoma, Esophageal Cancer, Neuroblastoma, Neuroblastoma, Retinoblastoma, Fallopian Tube Cancer, Gallbladder Cancer, Gastric (Stomach) Cancer, Gastrointestinal Carcinoid Tumor, Head and Neck Cancer, Hepatocellular (Liver) Cancer, Hodgkin Lymphoma, Intraocular Melanoma, Kaposi Sarcoma, Langerhans Cell Histiocytosis, Lip and Oral Cavity Cancer, Liver Cancer (Primary), Lung Cancer, Lymphoma, Melanoma, Mesothelioma, Non-Hodgkin Lymphoma, Non-Small Cell Lung Cancer, Osteosarcoma and Malignant Fibrous Histiocytoma of Bone, Ovarian Cancer, Pancreatic Cancer and Pancreatic Neuroendocrine Tumors (Islet Cell Tumors), Osteosarcoma, Rhabdomyosarcoma, Uterine Sarcoma, Vascular Tumors, Skin Cancer, Small Cell Lung Cancer, Small Intestine Cancer, Soft Tissue Sarcoma, Squamous Cell Carcinoma, Squamous Neck Cancer with Occult Primary, T-Cell Lymphoma, Testicular Cancer, Throat Cancer, Thymoma and Thymic Carcinoma, Thyroid Cancer, Uterine Cancer, Endometrial and Uterine Sarcoma, and Vaginal Cancer.

2. Subjects to be Treated

Typically, the subjects to be treated have a proliferative disease, such as a benign or malignant tumor. In some embodiments, the subjects to be treated have been diagnosed with stage I, stage II, stage III, or stage IV cancer.

In some embodiments, the subjects have been diagnosed with cancer in the absence of heart disease. In some embodiments, the subjects have been diagnosed with cancer in the presence of heart disease. In some embodiments, the subjects have been diagnosed with cancer in the absence of chronic conditions, such as diabetes. In some embodiments, the subjects have been diagnosed with cancer in the presence of chronic conditions, such as diabetes.

Exemplary heart disease includes coronary artery disease, stroke, atrial fibrillation, cardiomyopathy, heart failure, high cholesterol, aortic aneurism, high blood pressure, pulmonary hypertension, acute coronary syndrome, angina, stable angina, unstable angina, arrhythmia, atherosclerosis, congenital heart defects, peripheral arterial disease, ischemic heart disease, and rheumatic heart disease.

Exemplary chronic conditions include complications from smoking, asthma, Alzheimer's disease and related dementia, arthritis (osteoarthritis and rheumatoid), hepatitis (chronic viral B & C), HIV/AIDS, hyperlipidemia (high cholesterol), autism spectrum disorders, chronic kidney disease, osteoporosis, chronic obstructive pulmonary disease, schizophrenia and other psychotic disorders, depression, and diabetes 3. Effective Amounts to Reduce Tumor Size The amount effective to reduce tumor size in a subject may vary with each treatment need. The effective amount is typically an amount that reduces tumor size with acceptable, minimal, or substantially low levels of side effects. Potential side effects from the treatment may include cardiac related side effects, such as slow heart rate, palpitations, heart block, abnormal heart rhythm, difficulty in breathing and fainting.

The effective amount to reduce tumor size includes one or more doses of between about 0.0001 mg/kg and 10 mg/kg, such as between about 0.0001 mg/kg, 0.0003 mg/kg, about 0.0005 mg/kg, about 0.0008 mg/kg, about 0.001 mg/kg, about 0.003 mg/kg, about 0.005 mg/kg, about 0.008 mg/kg, about 0.1 mg/kg, or about 0.2 mg/kg. Specific ranges for the effective amount to reduce tumor size include between about 0.0001 mg/kg and about 0.2 mg/kg, about 0.001 mg/kg and about 0.2 mg/kg, about 0.01 mg/kg and about 0.2 mg/kg, and about 0.1 mg/kg and about 0.2 mg/kg.

The effective amount to reduce tumor size may be between about 0.0001 mg and 10 mg, such as about 0.0001 mg, 0.0003 mg, about 0.0005 mg, about 0.0008 mg, about 0.001 mg, about 0.003 mg, about 0.005 mg, about 0.008 mg, about 0.1 mg, about 0.3 mg, about 0.5 mg, about 0.8 mg, about 1 mg, about 2 mg, about 3 mg, about 4 mg, about 5 mg, about 6 mg, about 7 mg, about 8 mg, about 9 mg, about 10 mg, or about 15 mg.

The effective amount may be delivered twice daily, once daily, twice weekly, weekly, or in any dosing regimen suitable for treating a subject with cancer.

The effective amount of a composition may be combined with a standard of care treatment as a combination treatment. The combination therapy may be a combination of an effective amount of the HCN1, HCN2, HCN3, and/or HCN4 inhibitor with another active agent, such as any active agent used in standard of care treatments. The effective amount of the inhibitor may be administered with an existing chemotherapeutic regimen, before an existing chemotherapeutic regimen, or after the chemotherapeutic regimen has been completed.

For combination therapy, the dosages of the HCN1, HCN2, HCN3, and/or HCN4 inhibitor may vary. For example, the dosages may be between 0.0001 mg/kg and 0.001 mg/kg when the inhibitor is combined with a second active agent. In some forms, the dosages may be between 0.001 mg/kg and 0.2 mg/kg when the inhibitor is combined with a second active agent.

The dosages or amounts of the compounds described herein are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied.

The efficacy of administration of a particular dose of the compounds or compositions according to the methods described herein can be determined by evaluating the particular aspects of the medical history, signs, symptoms, and objective laboratory tests that are known to be useful in evaluating the status of a subject in need of HCN1, HCN2, HCN3, and/or HCN4 inhibitors for the treatment of cancer or other diseases and/or conditions. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: (1) a subject's physical condition is shown to be improved (e.g., a tumor has partially or fully regressed), (2) the progression of the disease or condition is shown to be stabilized, or slowed, or reversed, or (3) the need for other medications for treating the disease or condition is lessened or obviated, then a particular treatment regimen will be considered efficacious.

4. Effective Amounts to Put and Keep Cancer in Remission

In some embodiments, an effective amount of the composition is used to put cancer in remission and/or keep the cancer in remission.

An effective amount of the composition to put the cancer in remission, and/or keep cancer in remission includes one or more doses of between about 0.0001 mg/kg and 0.2 mg/kg, such as about 0.0001 mg/kg, 0.0003 mg/kg, about 0.0005 mg/kg, about 0.0008 mg/kg, about 0.001 mg/kg, about 0.003 mg/kg, about 0.005 mg/kg, about 0.008 mg/kg, about 0.1 mg/kg, or about 0.2 mg/kg. Specific ranges for the effective amount to put the cancer in remission, and/or keep cancer in remission include between about 0.0001 mg/kg and about 0.2 mg/kg, about 0.001 mg/kg and about 0.2 mg/kg, about 0.01 mg/kg and about 0.2 mg/kg, and about 0.1 mg/kg and about 0.2 mg/kg of the composition.

The effective amount of the composition to put the cancer in remission, and/or keep cancer in remission may be between about 0.0001 mg and 10 mg, such as about 0.0001 mg, 0.0003 mg, about 0.0005 mg, about 0.0008 mg, about 0.001 mg, about 0.003 mg, about 0.005 mg, about 0.008 mg, about 0.1 mg, about 0.3 mg, about 0.5 mg, about 0.8 mg, about 1 mg, about 2 mg, about 3 mg, about 4 mg, about 5 mg, about 6 mg, about 7 mg, about 8 mg, about 9 mg, about 10 mg, or about 15 mg of the composition.

The effective amount may be delivered twice daily, once daily, twice weekly, weekly, or in any dosing regimen suitable for treating a subject with cancer.

5. Effective Amounts to Stop or Reduce Cancer Stem Cell Proliferation

Also provided are effective amounts of the compositions to reduce or stop cancer stem cell proliferation.

The effective amount to reduce or stop cancer stem cell proliferation includes one or more doses of about 0.0001 mg/kg and about 0.2 mg/kg, such as about 0.0001 mg/kg, 0.0003 mg/kg, about 0.0005 mg/kg, about 0.0008 mg/kg, about 0.001 mg/kg, about 0.003 mg/kg, about 0.005 mg/kg, about 0.008 mg/kg, about 0.1 mg/kg, or about 0.2 mg/kg of the composition.

In other embodiments, the effective amounts to reduce or stop cancer stem cell proliferation include between about 0.0001 mg and about 10 mg, such as about 0.0001 mg, 0.0003 mg, about 0.0005 mg, about 0.0008 mg, about 0.001 mg, about 0.003 mg, about 0.005 mg, about 0.008 mg, about 0.1 mg, about 0.3 mg, about 0.5 mg, about 0.8 mg, and about 1 mg of the composition.

The effective amount may be delivered twice daily, once daily, twice weekly, weekly, or in any dosing regimen suitable for treating a subject with cancer.

6. Methods of Testing Effects of Compounds

The methods used to detect reduction in tumor size, reduction in proliferation of cancer stem cells, or cancers in remission include biopsies, non-invasive imaging methods, recording methods, laboratory tests detecting blood biomarkers, and/or visual evaluation.

Examples of non-invasive methods include contrast-enhanced and non-enhanced magnetic resonance imaging (MRI), computerized tomography (CT), positron-emission tomography (PET), single-photon emission computed tomography (SPECT), X-ray, mammography, ultrasonography or ultrasound, endoscopy, elastography, tactile imaging, thermography, and medical photography.

Other methods include measurement and recording techniques, such as electroencephalography (EEG), magnetoencephalography (MEG), and electrocardiography (ECG).

Examples of laboratory tests include complete blood count (CBC), blood protein testing (electrophoresis), tumor marker tests, and detecting circulating tumor cells.

H. Kits

The compositions described above as well as other materials can be packaged together in any suitable combination as a kit useful for performing, or aiding in the performance of, the disclosed method. It is useful if the kit components in a given kit are designed and adapted for use together in the disclosed method. For example, disclosed are kits with one or more dosages packed for injection into a subject, and may include a pre-measured dosage of a pharmaceutical composition in a sterile needle, ampule, tube, container, or other suitable vessel. The kits may include instructions for dosages and dosing regimens. The kits also contain combinations of pharmaceutical compositions described herein for co-administration.

EXAMPLES

Example 1. HCN2 and HCN3 Proteins are Overexpressed in Breast Cancer Cells, Colon Cancer Cells, Ovarian Cancer Cells and Liver Cancer Cells when Compared to their Expression in Non-Tumorigenic Breast Cells

Materials and Methods

Cell lines: MCF10A (normal breast cancer cell line), MCF7 (ER+, PR+, HER2−), ZR75-1(ER+, PR+), BT474 (ER+, PR+, HER2+), MDA-MB-231 (triple negative breast cancer cell line) and MDA-MB-453(triple negative breast cancer cell line). SW1116 (colon cancer cell line), HT-29 (colon cancer cell line), Ishikawa (ovarian cancer cell line), Huh7 (liver cancer cell line), MHCC97L (liver cancer cell line), PLC/PRF/5 (liver cancer cell line), BEL-7402 (liver cancer cell line) and Hep3B (liver cancer cell line).

Cell culture: MCF10A was cultured in MEGM supplemented with 100 ng/ml cholera toxin; MCF7, BT474, MDA-MB-231, SW1116, HT-29, Huh7, MHCC97L, PLC/PRF/5, BEL-7402 and Hep3B were cultured in DMEM supplemented with 10% Fetal Bovine Serum (FBS) and 1% Penicillin/Streptomycin; ZR75-1 and MDA-MB-453 were culture in IMEM supplemented with 10% Fetal Bovine Serum (FBS) and 1% Penicillin/Streptomycin; Ishikawa was cultured in MEM supplemented with 5% Fetal Bovine Serum (FBS) and 1% Penicillin/Streptomycin. All cells were incubated in incubator at 37° C. with 5% $CO_2$.

Seed cell: Cells were seeded at density of $1\times10^6$ cells/well in 6 well plates.

Cell harvest: Cells were washed with 1 mL of 1×phosphate-buffered saline (PBS). Cells were detached from the well by treating the cells with 1 mL of Trypsin. Cell suspension was collected and transferred to a new 1.5 mL tube. The cell suspension was centrifuged at 13000×g for 1 mins. The supernatant was discarded. The cell pellet was resuspended in 1 mL of 1×PBS. The cell suspension was centrifuged at 13000×g for 1 min. The supernatant was discarded. The cell pellet was resuspended in 200 μL of cell lysis buffer (Cell signalling) and incubated on ice for 30 minutes. Protein assay was performed to measure the protein concentration of the cell lysate with the use of DC protein assay kit (Bio-rad).

Western blot: Cells were lysed in lysis buffer (Cell signaling technology) on ice for 30 minutes. 20 μg of protein samples was loaded onto 10% polyarcyamide gel. The proteins were separated by electrophoresis. The proteins were then transferred to PVDF membrane. The membrane was blocked in 5% skim milk for 1 hour at room temperature. The membrane was incubated with primary antibody anti-HCN2 (1:1000; Alomone Lab, APC-030), anti-HCN3 (1:1000; Alomone Lab, APC-057) and anti-actin (1:4000; Santa Cruz Biotechnology, sc-47778).

Storage of cells and Freezing: Approximately $3\times10^6$ cells in 750 μl fresh cell culture medium were pipetted into a cryotube. 750 μl of freezing medium (80% FCS and 20% DMSO (PAN)) were added. Using a Nalgene Cryo Freezing Container the cryotubes were placed in a −80° C. freezer immediately and transferred to liquid N2 within 24 hours for long-term storage.

Storage of cells and Thawing: The cryotubes were quickly thawed as possible in a 37° C. water bath. The cells were diluted with 10 ml cold medium and centrifuged at 1000 rpm for 10 min. Then the pellets were resuspended in cell culture medium and transferred into 25 ml cell culture flasks.

Results

Figure 2:
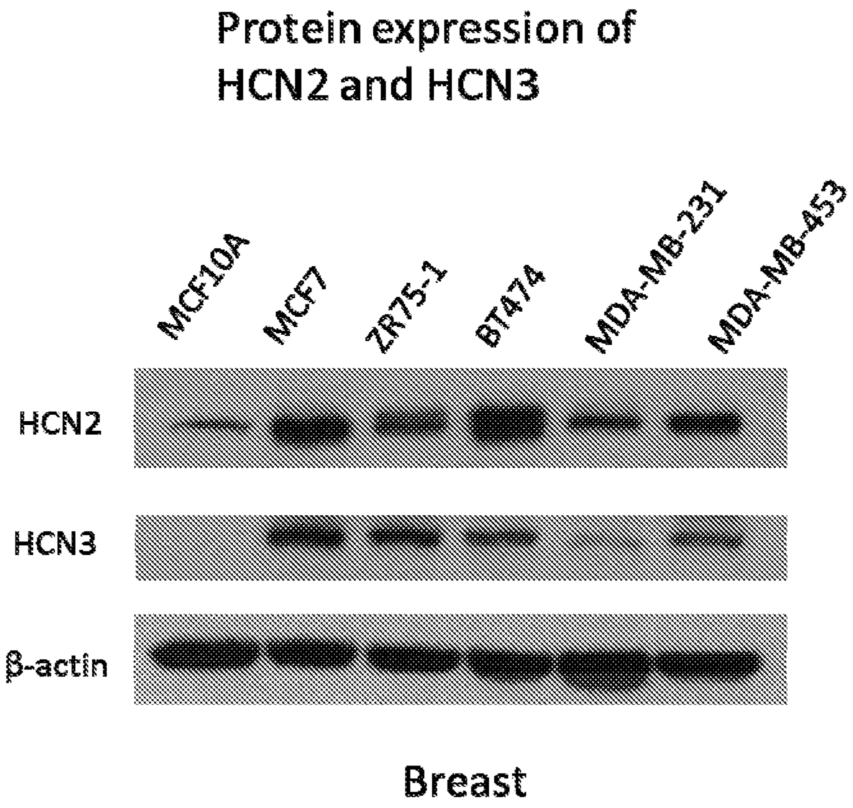
FIG. 2 shows Western blot analysis of HCN2 and HCN3 in breast cancer cells MCF7, ZR75-1, BT-474, MDA-MB-231 and MDA-MB-453 compared with non-tumorigenic breast cell MCF10A. β-actin was a loading control.

Western blot demonstrated that the protein expression for HCN2 and HCN3 was overexpressed in breast cancer cells (MCF7, ZR75-1, BT474, MDA-MB-231 and MDA-MB-453) but not in non-tumorigenic breast cell line MCF10A. Beta-actin was used as loading control (FIG. 2).

Figure 14A:
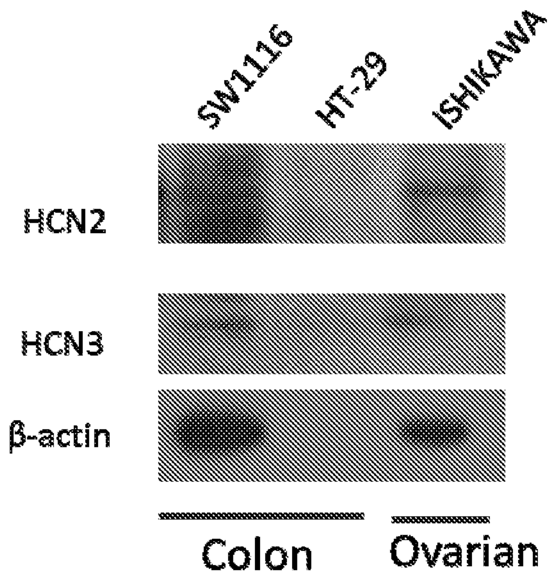
FIG. 14A shows Western blot analysis of HCN2 and HCN3 in colorectal (SW1116 and HT-29) and ovarian (ISHIKAWA) cancer cell lines. β-actin was a loading control.

Western blot demonstrated that the protein expression for HCN2 and HCN3 in colon cancer cells SW1116 and HT-29. Beta-actin was used as loading control (FIG. 14A).

Western blot demonstrated that the protein expression for HCN2 and HCN3 in ovarian cancer cells Ishikawa. Beta-actin was used as loading control (FIG. 14A).

Figure 14B:
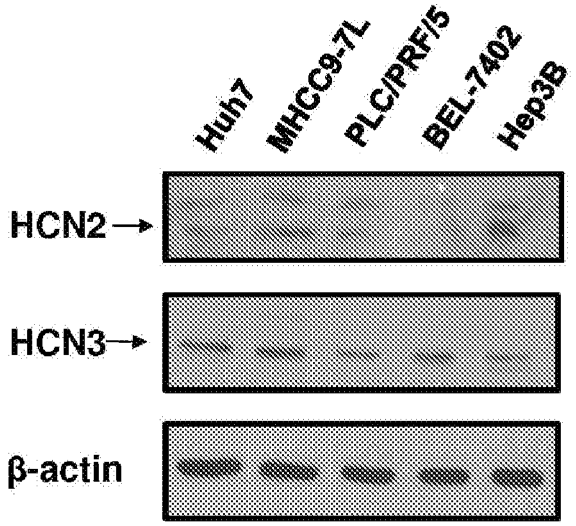
FIG. 14B shows Western blot analysis of HCN2 and HCN3 expression in a panel of HCC cell lines. β-actin was a loading control.

Western blot demonstrated that the protein expression for HCN2 and HCN3 in a panel of liver cancer cells. Beta-actin was-used as loading control (FIG. 14B).

Example 2. Significant Increase in Expression of HCN2 and HCN3 mRNA in Breast Cancer Tissues, Colon Cancer Tissues, Ovarian Cancer Tissues and Liver Cancer Tissues

Materials and Methods

The primary breast cancer tissue mRNA expression data were obtained from publically available TCGA, Radvanyi and Curtis datasets.

The primary colon cancer tissue mRNA expression data were obtained from publically available TCGA datasets.

The primary ovarian cancer tissue mRNA expression data were obtained from publically available Lu ovarian and Yoshihara datasets.

The primary liver cancer tissue mRNA expression data were obtained from publically available TCGA datasets.

The primary lung adenocarcinoma tissue mRNA expression data were obtained from publically available TCGA datasets.

Results

The data showed statistically significant increase in expression of HCN2 and HCN3 in breast cancer tissue compared with normal breast tissue. Student t-test was used to determine the statistical significance. The results are shown in FIGS. 1A-1D.

Figure 10A:
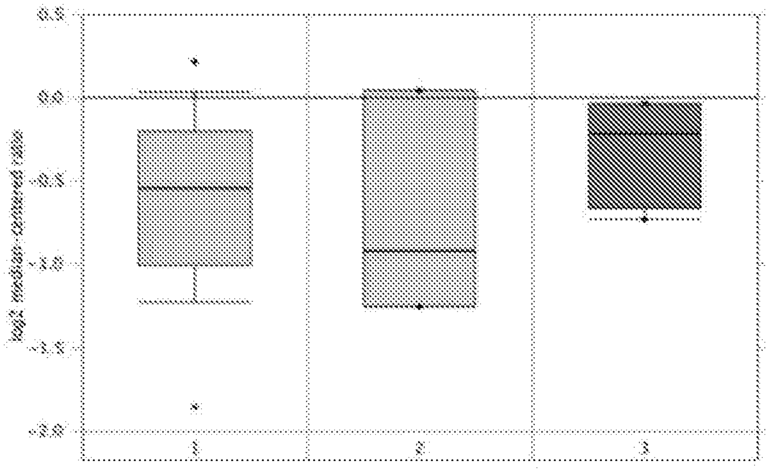
FIG. 10A shows mRNA expression of HCN2 in the tumor tissues obtained from TCGA Colorectal dataset (Rectal Mucinous Adenocarcinoma; Normal colon(1), Normal Rectum(2) vs. Carcinoma(3); p=0.047, Fold change=1.225)
Figure 10B:
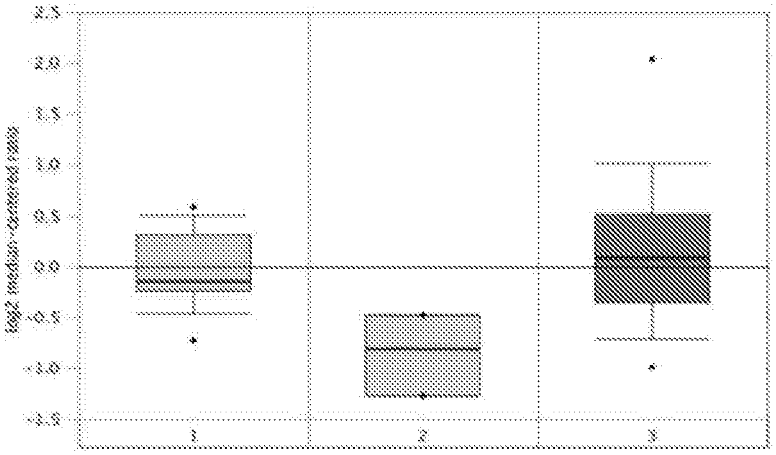
FIG. 10B shows mRNA expression of HCN3 in the tumor tissues obtained from TCGA Colorectal dataset (Colon Adenocarcinoma; Normal colon(1), Normal Rectum(2) vs. Carcinoma(3); p=0.021, Fold change=1.186). Student t-test was used to determine the statistical significance.

The data showed statistically significant increase in expression of HCN2 and HCN3 in colon cancer tissue compared with normal colon tissue. Student t-test was used to determine the statistical significance. The results are shown in FIGS. 10A-10B.

Figure 11A:
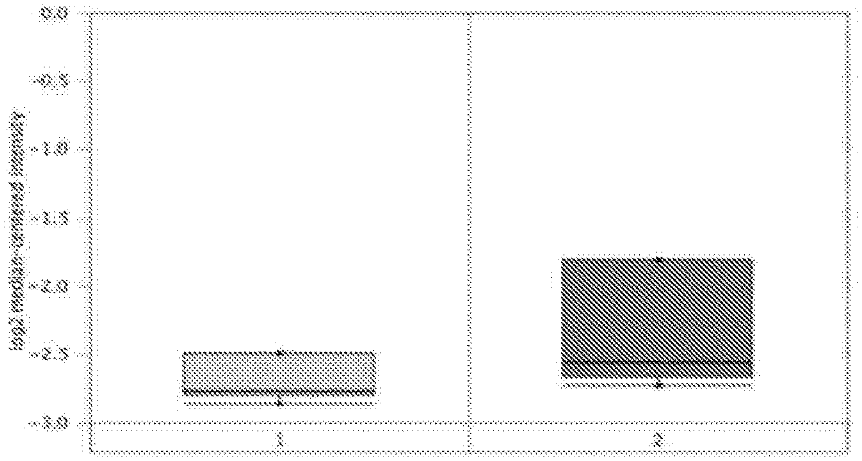
FIG. 11A shows mRNA expression of HCN2 in the tumor tissues obtained from Lu ovarian dataset (Ovarian cell adenocarcinoma; Ovarian surface epithelium vs. Ovarian clear cell adenocarcinoma; p=0.029, Fold change=1.277)
Figure 11B:
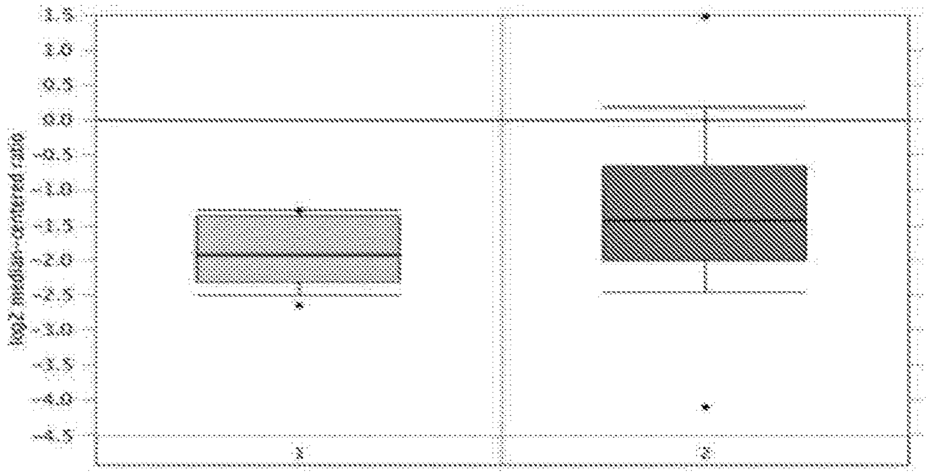
FIG. 11B shows mRNA expression of HCN3 in the tumor tissues obtained from Yoshihara ovarian dataset (Ovarian Serous Adenocarcinoma; Peritoneum vs. Ovarian Serous Adenocarcinoma; p=0.006, Fold change=1.520). Student t-test was used to determine the statistical significance.

The data showed statistically significant increase in expression of HCN2 and HCN3 in ovarian cancer tissue compared with normal tissue. Student t-test was used to determine the statistical significance. The results are shown in FIGS. 11A-11B.

Figure 12A:
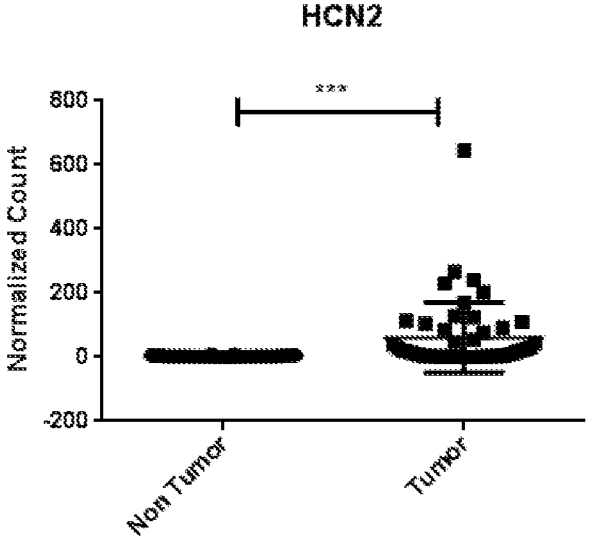
FIG. 12 shows the Cancer Genome Atlas (TCGA) data set of hepatocellular carcinoma. Overexpression of HCN2 (FIG. 12A) and HCN3 (FIG. 12B) was observed (*p<0.001). From dataset GSE25097, overexpression of HCN2 was significantly correlated with poorer disease free survival (p=0.039) (FIG. 12C), and overexpression of HCN3 showed a trend of poorer overall survival (p=0.054) (FIG. 12**D).
Figure 12B:
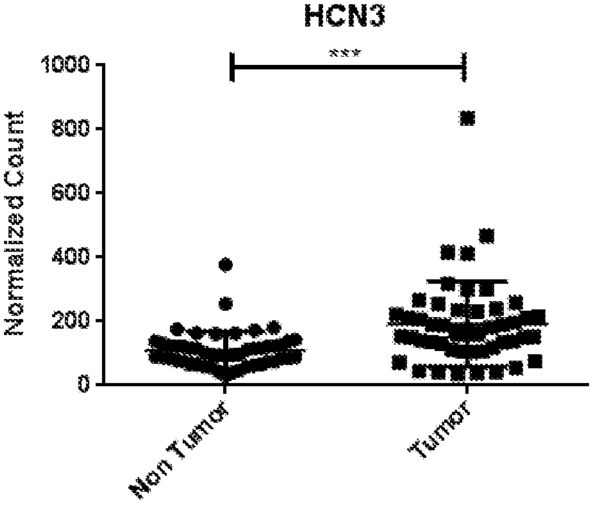

The data showed statistically significant increase in expression of HCN2 and HCN3 in liver cancer tissue compared with adjacent non-tumor tissue. Student t-test was used to determine the statistical significance. The results are shown in FIGS. 12A-12B.

Figure 13A:
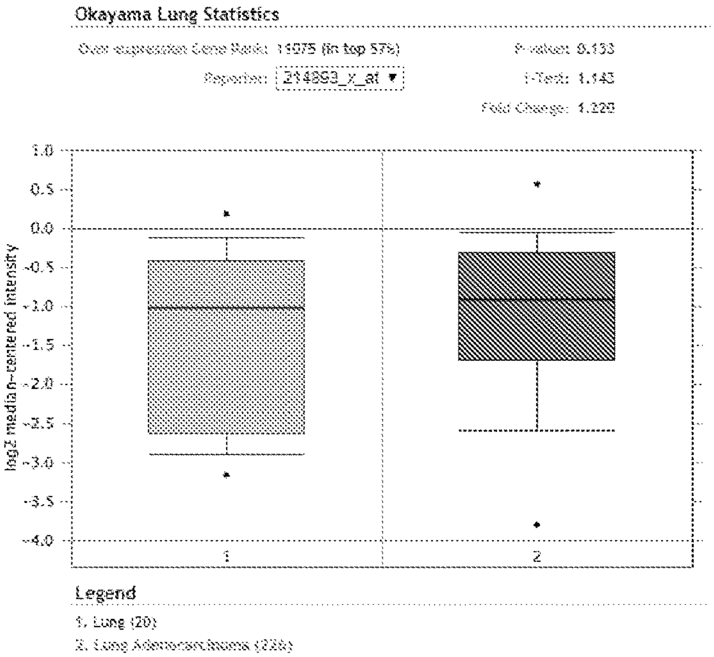
FIG. 13A shows HCN2 expression in Okayama lung (Lung Adenocarcinoma vs. Normal, fold change=1.22, p=0.133)
Figure 13B:
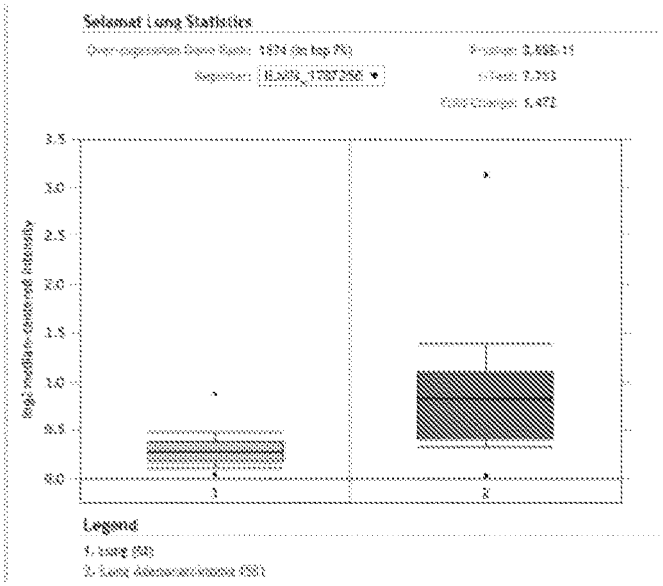
FIG. 13B shows HCN3 expression in Selamat lung (Lung Adenocarcinoma vs. Normal, fold change=1.472, $p=3.55\times10^{-11}$). Student t-test was used to determine the statistical significance.

The data showed statistically significant increase in expression only of HCN3 but not HCN2 in lung adenocarcinoma tissue compared with normal lung tissue. Student t-test was used to determine the statistical significance. The results are shown in FIGS. 13A-13B.

Survival Analysis of HCN2 Expression in Liver Cancer Patients

Materials and Methods

Kaplan-Meier survival analysis was used to analyze disease-free survival and overall survival of TCGA dataset (GSE25097), and the statistical significance was calculated by log-rank test; these analyses were carried out using SPSS 20.

Results

Figure 12C:
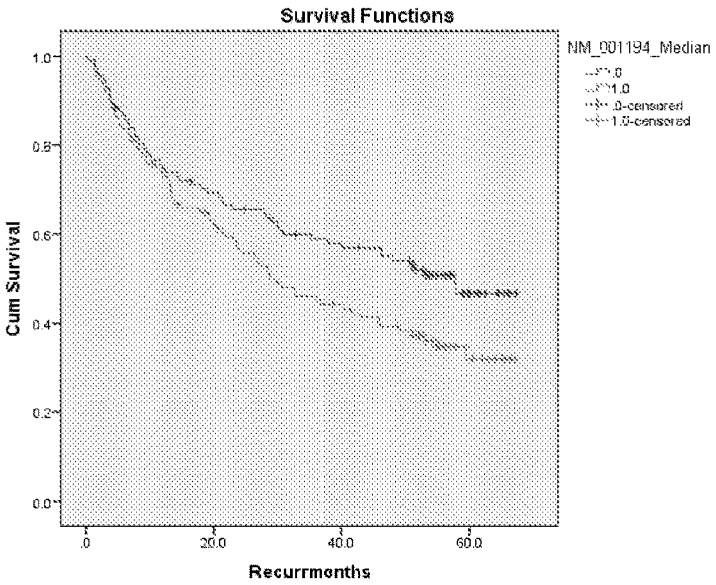
Figure 12D:
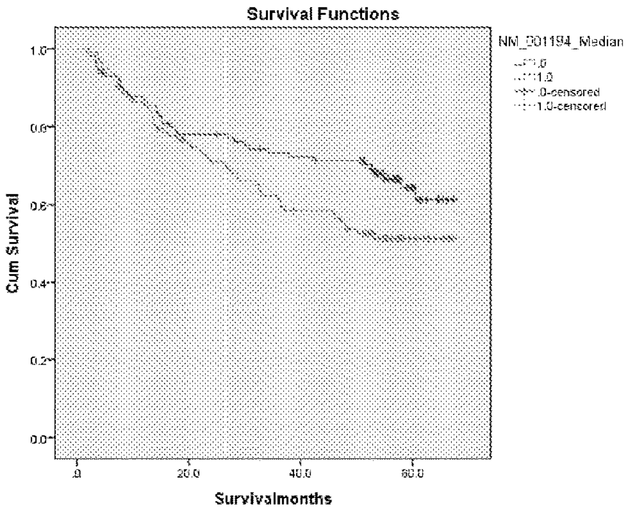

The data showed that overexpression of HCN2 was significantly correlated with poorer disease free survival ($p=0.039$) and a trend of poorer overall survival ($p=0.054$). The results are shown in FIGS. 12C and 12D.

Example 3. Ivabradine Inhibits Proliferation of Breast Cancer, Ovarian Cancer, Colon Cancer, and Liver Cancer Cell Lines

Materials and Methods

Ivabradine was purchased (Sigma). The powder was dissolved into double-distilled water.

MCF10A, MCF7, ZR75-1, BT474, MDA-MB-231, MDA-MB-453, Ishikawa, SW1116, PLC/PRF/5, MHCC- 97L and Huh7 cells were seeded in 96-well plate with cell density 5000 cells per well. 200 μM of Ivabradine was used for cell treatment while double distilled water was used as control. 3-(4,5-dimethyl-2-thiazolyl)-2,5-diphenyl-2H-tetrazolium bromide (MTT) assay was performed 24, 48, 72 and 96 hours after Ivabradine treatment. MTT solution was prepared at 5 mg/mL in PBS and was filtered through a 0.2 μm filter. Then, 50 μl of MTT plus 200 μl of culture medium were added into each well. Cells were incubated for 4 hours at 37° C. with 5% $CO_2$, 95% air and complete humidity. After 4 hours, the medium with MTT solution was removed and replaced with 200 μl of isopropanol with 4 mmol/L HCl and 0.1% NP-40. The 96-well plate was further incubated for 5 min at room temperature. The optical density of the wells was determined using a plate reader at a test wavelength of 570 nm and a reference wavelength of 630 nm.

Results

Figure 3A:
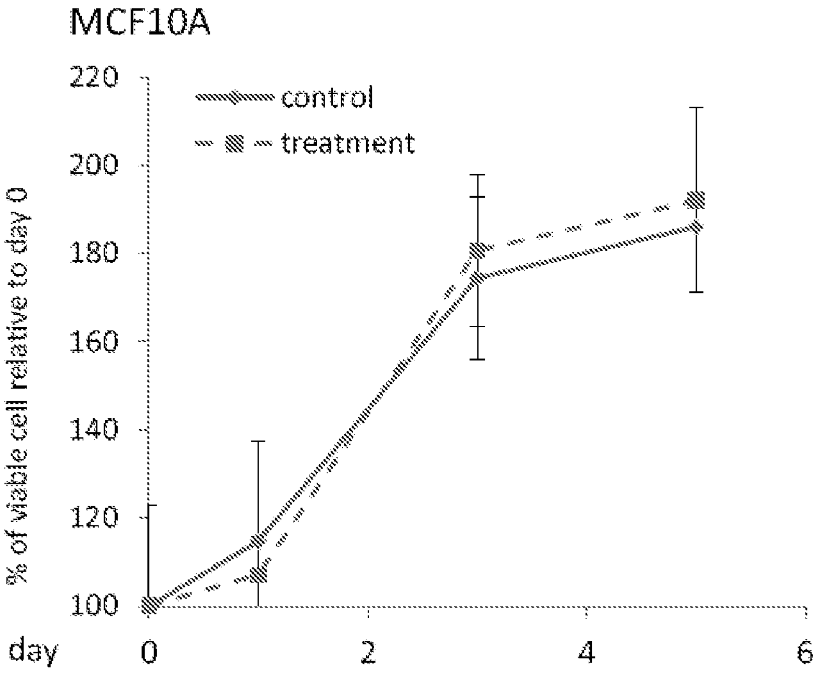
FIGS. 3A, 3B, 3C, 3D, and 3E are line graphs showing survival of cells (% of viable cells relative to day 0) at indicated days of treatment. Cells were treated with 200 μM of Ivabradine for 5 days. All MTT assays were repeated in triplicate. The results were shown as mean±s.d. Statistical significance was determined by two-way ANOVA with $P<0.05$ regarded as statistically significant.
Figure 3B:
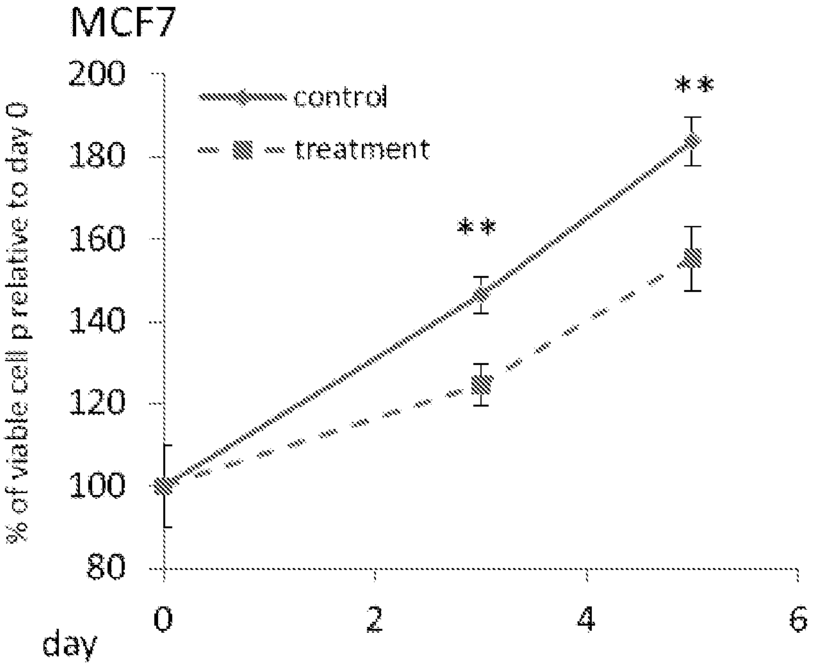
Figure 3C:
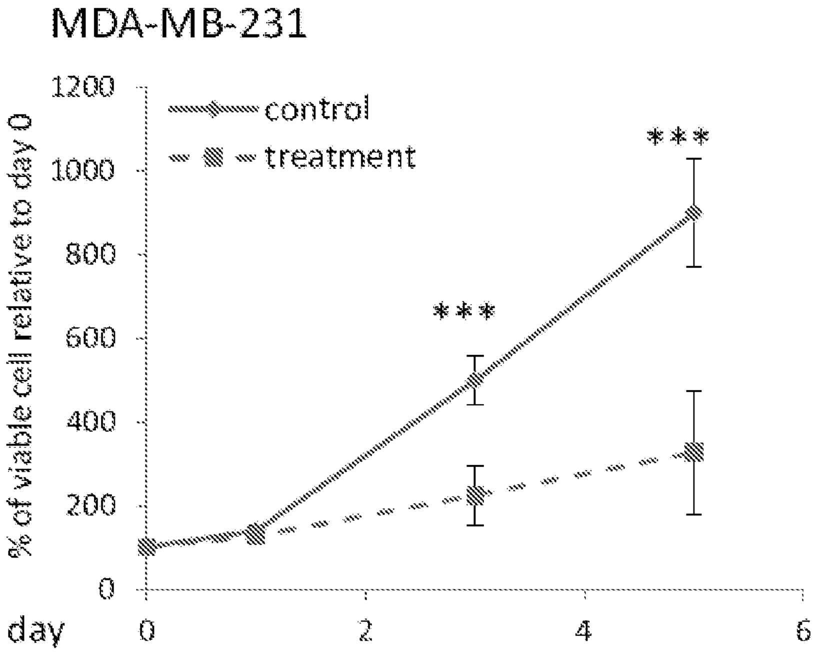
Figure 3D:
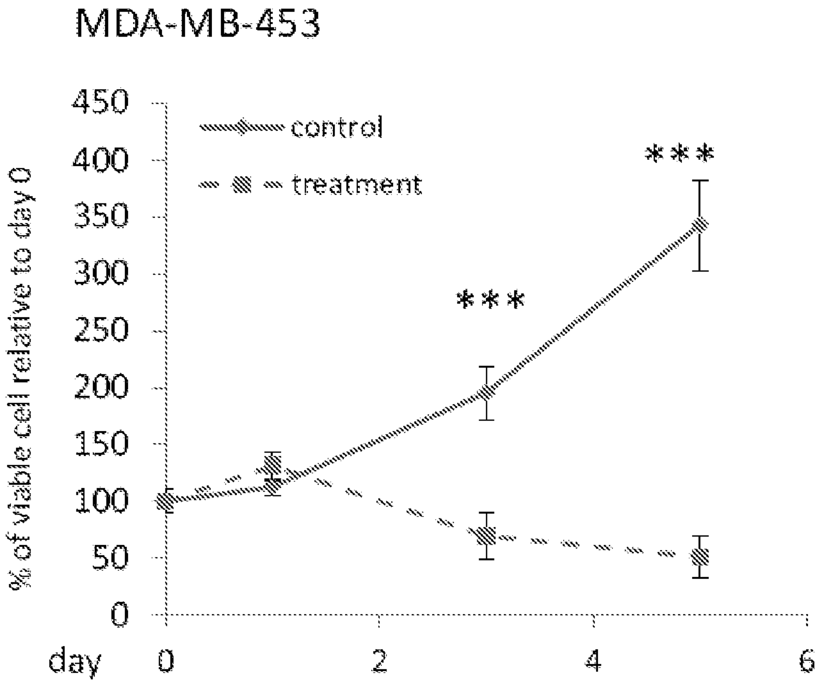
Figure 3E:
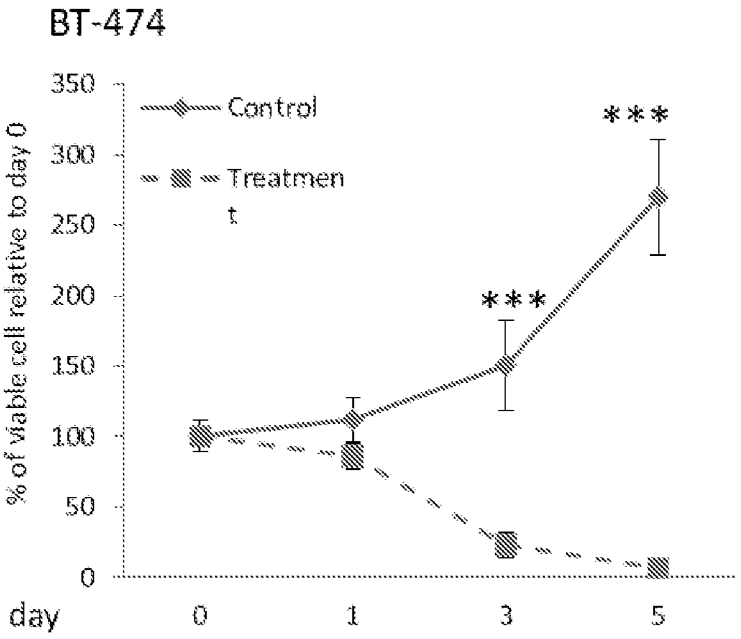

The treatment with 200 μM of Ivabradine for 5 days significantly reduced the proliferation of breast cancer cell lines MCF7 (ER, PR+, HER2−ve, FIG. 3B), BT474 (triple positive, FIG. 3E) and two TNBC cell lines MDA-MB-231 (FIG. 3C) and MDA-MB-453 (FIG. 3D), but not non-tumorigenic breast cell line MCF-10A (FIG. 3A) by MTT assay. Double distilled water served as control. MTT assays were repeated in triplicate. The results were shown as mean±s.d. Statistical significance was determined by two-way ANOVA with P<0.05 regarded as statistically significant.

Figure 15:
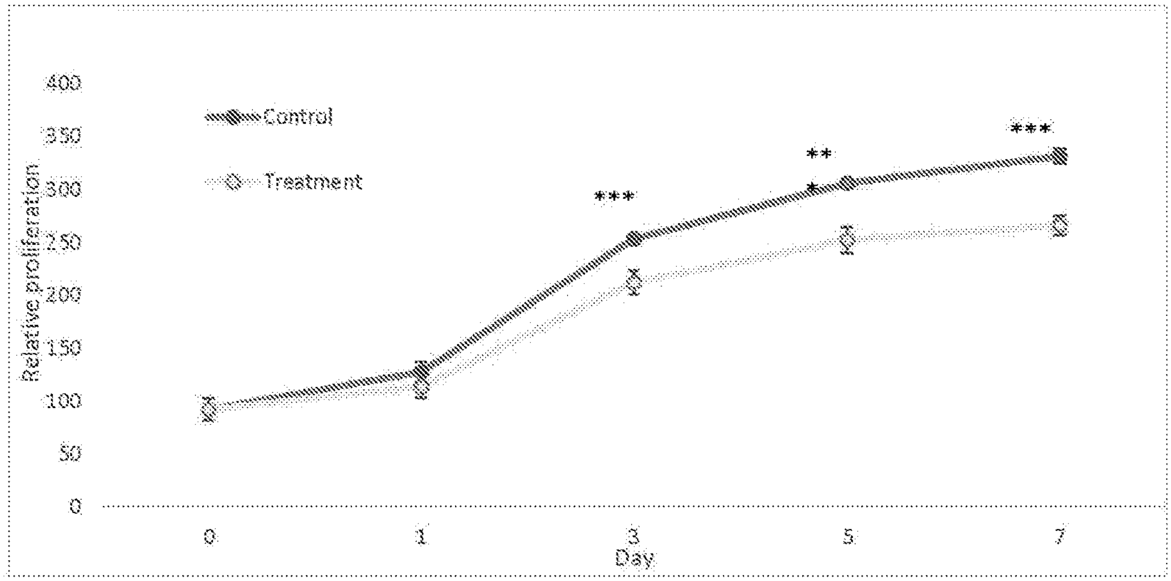
FIG. 15 shows the suppressive effect of Ivabradine (200 μM) on the cell proliferation of Ishikawa ovarian cancer cells.  p<0.01, *p<0.001. Student t-test was used to determine the statistical significance

The treatment with 200 μM of Ivabradine for 7 days significantly reduced the proliferation of ovarian cancer cell line Ishikawa (FIG. 15). Double distilled water served as control. MTT assays were repeated in triplicate. The results were shown as mean±s.d. Statistical significance was determined by two-way ANOVA with P<0.05 regarded as statistically significant.

Figure 16:
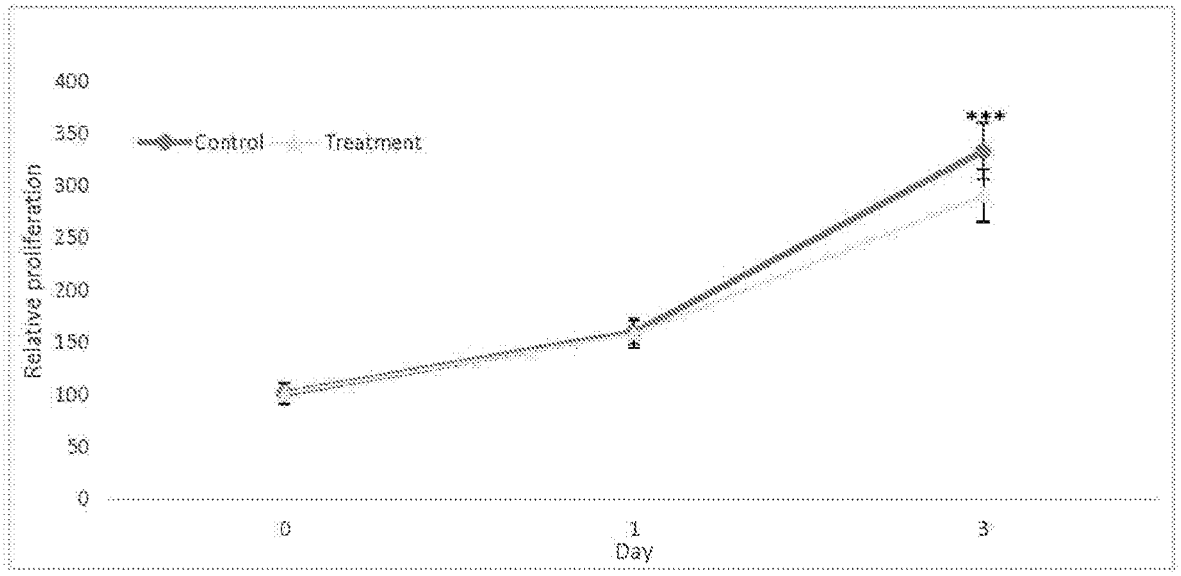
FIG. 16 shows the suppressive effect of Ivabradine (200 μM) on the cell proliferation of SW1116 colon cancer cells. p<0.001. Student t-test was used to determine the statistical significance.

The treatment with 200 μM of Ivabradine for 3 days significantly reduced the proliferation of colon cancer cell line SW1116 (FIG. 16). Double distilled water served as control. MTT assays were repeated in triplicate. The results were shown as mean±s.d. Statistical significance was determined by two-way ANOVA with P<0.05 regarded as statistically significant.

Figure 17A:
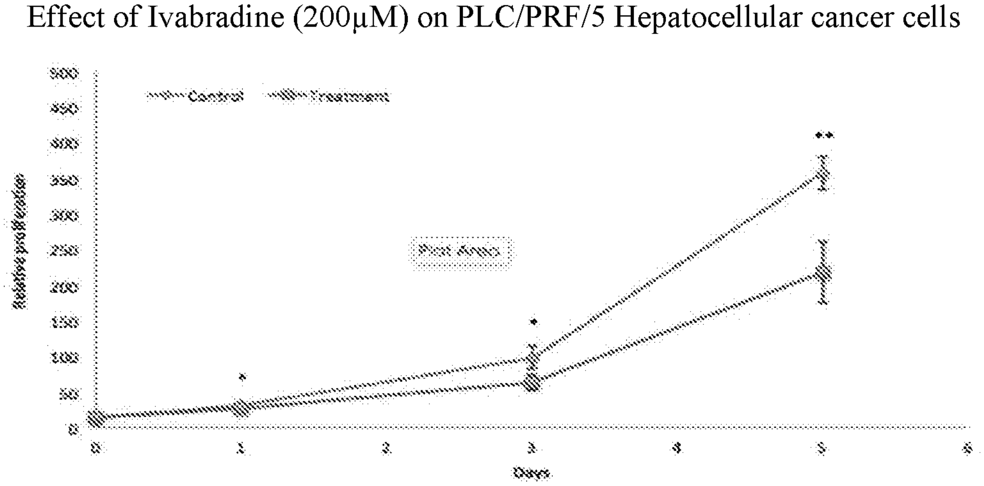
FIG. 17A shows the suppressive effect of Ivabradine (200 μM) on the cell proliferation of PLC/PRF/5 hepatocellular carcinoma cells.
Figure 17B:
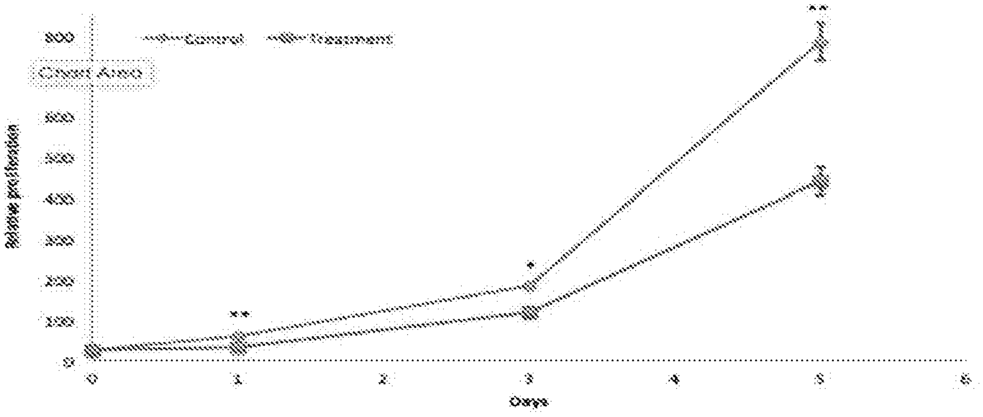
FIG. 17B shows the suppressive effect of Ivabradine (200 μM) on the cell proliferation of MHCC-97L hepatocellular carcinoma cells.
Figure 17C:
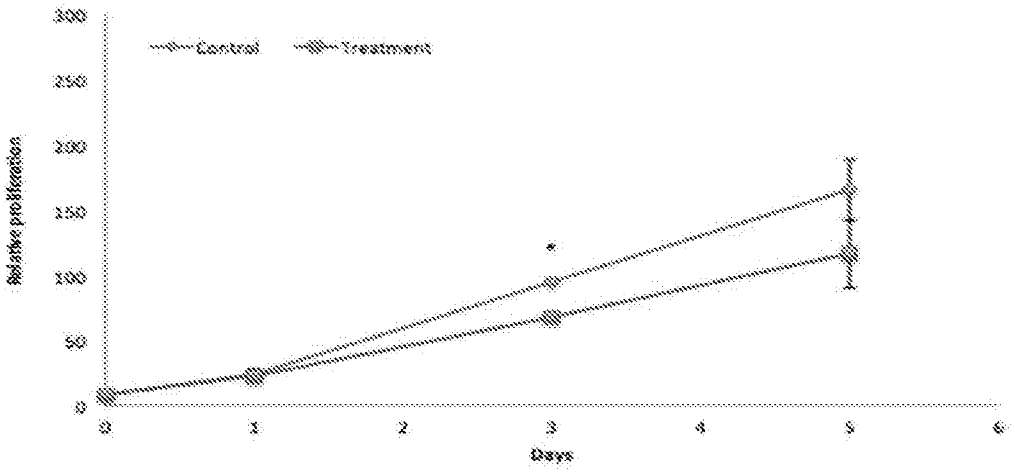
FIG. 17C shows the suppressive effect of Ivabradine (200 μM) on the cell proliferation of Huh7 hepatocellular carcinoma cells. * p<0.05, ** p<0.01. Student t-test was used to determine the statistical significance.

The treatment with 200 μM of Ivabradine for 5 days significantly reduced the proliferation of liver cancer cell lines PLC/PRF/5 (FIG. 17A), MHCC-97L (FIG. 17B) and Huh7 (FIG. 17C). Double distilled water served as control. MTT assays were repeated in triplicate. The results were shown as mean±s.d. Statistical significance was determined by two-way ANOVA with P<0.05 regarded as statistically significant.

Example 4. Ivabradine Inhibits In Vitro Tumor Growth

Materials and Methods

For the clonogenic assay, 2000 cells were seeded in 6-well plate. 200 μM of Ivabradine was used to treat the cells while double distilled water was used as negative control. The cells were treated for 14 days. The cells were washed with 1 mL of 1×PBS and then fixed by incubating with 4% paraformaldehyde in PBS for 15 minutes at room temperature. The cells were washed with 1 mL of 1×PBS. The cell colonies were visualized by staining with 0.5% crystal violet (Sigma) solution for 1 hour at room temperature. The cells were washed with tap water. The number of cells equal or greater than 50 cells would be regarded as one colony. Number of colonies was counted. After the counting, stain was extracted by incubating with 500 μL of 10% acetic acid solution. The optical density at 650 nm was measured.

Results

Figure 4A:
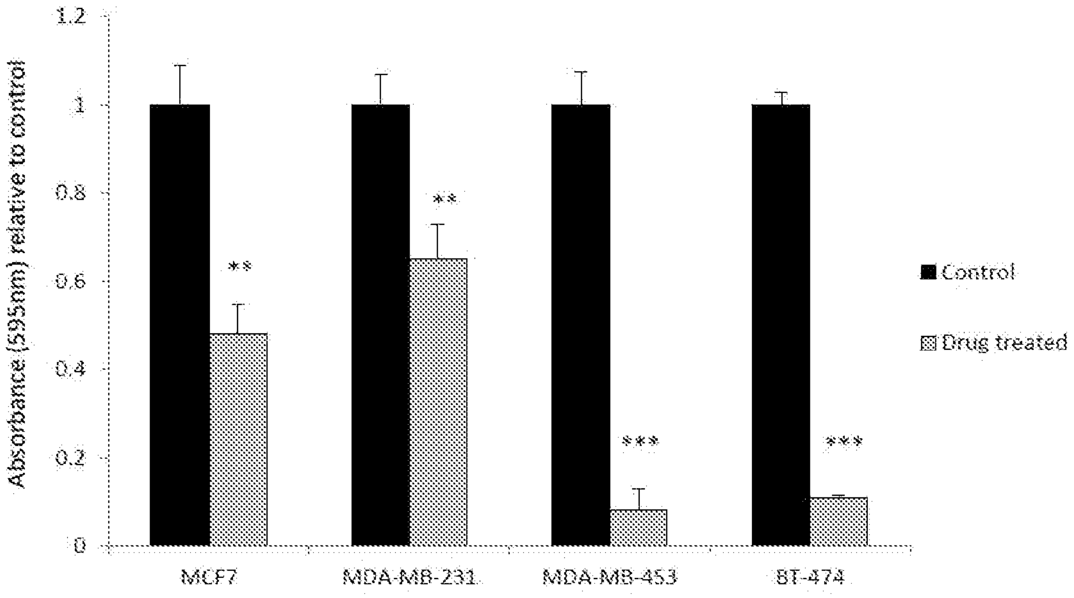
FIGS. 4A and 4B are bar graphs showing results of a clonogenic assay testing the breast cancer cell colony formation and proliferation. The breast cancer cells (MCF7, MDA-MB-231, MDA-MB-453, and BT-474 (FIG. 4A)) and the non-tumorigenic breast cells MCF10A (FIG. 4B) were treated with 200 μM of Ivabradine or control (distilled water) for 2 weeks and the cells were stained with 0.5% of crystal violet after fixation in 4% formaldehyde. After scanning the images, 10% acetic acid was used to extract the pigment for colorimetric assay. Absorbance at 595 nm was measured. Data was expressed as mean±SD from three independent experiments. Statistical significance at each time point was determined by student t-test.
Figure 4B:
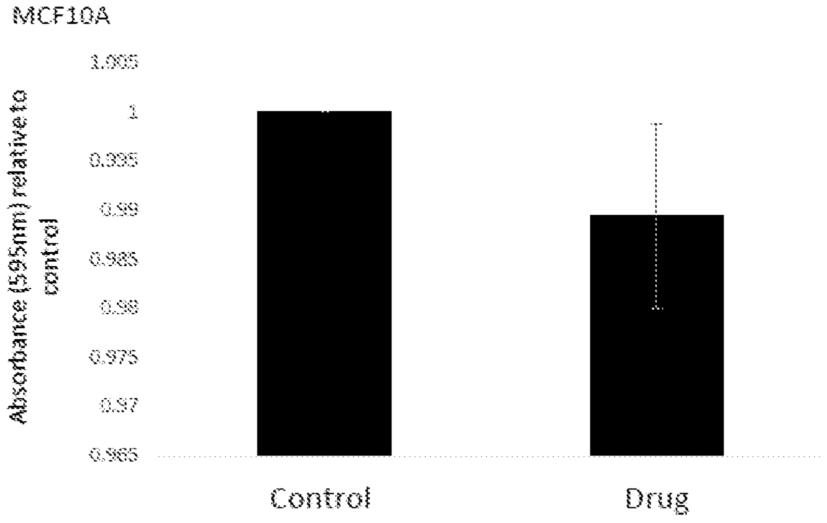
Figure 5A:
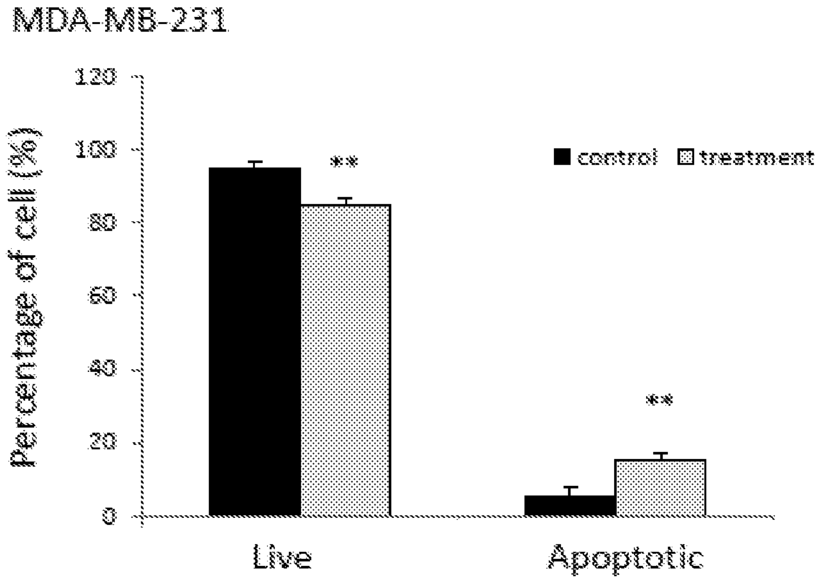
FIGS. 5A, 5B, 5C, and 5D are bar graphs showing percentage of live or apoptotic cells after breast cancer cells MDA-MB-231 (FIG. 5A), MDA-MB-453 (FIG. 5B), and BT-474 (FIG. 5C)) and the non-tumorigenic breast cells MCF10A (FIG. 5D) were treated with 200 μM of Ivabradine (Treatment) or double-distilled water (Control) for 24 hours (BT474) or 72 hours (MBA-MD-231, MDA-MB-453 and MCF10A). Data was expressed as mean±SD from three independent experiments. * represents $p<0.05$;  represents $p<0.01$; * represents $p<0.001$.
Figure 5B:
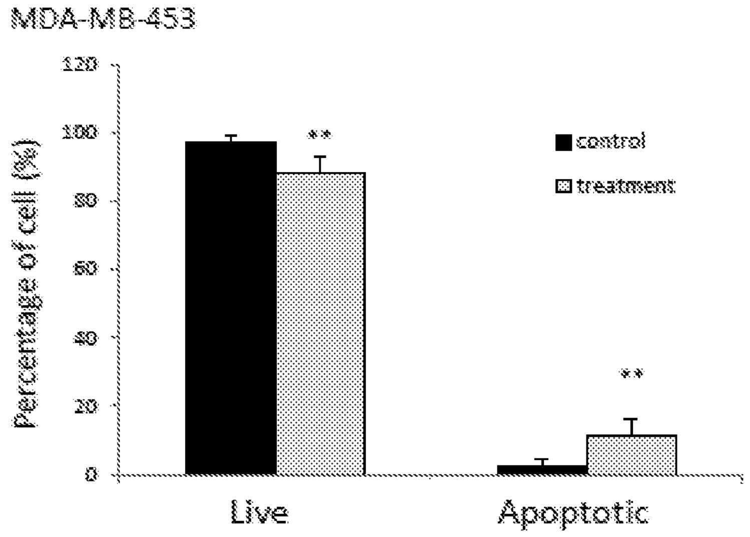
Figure 5C:
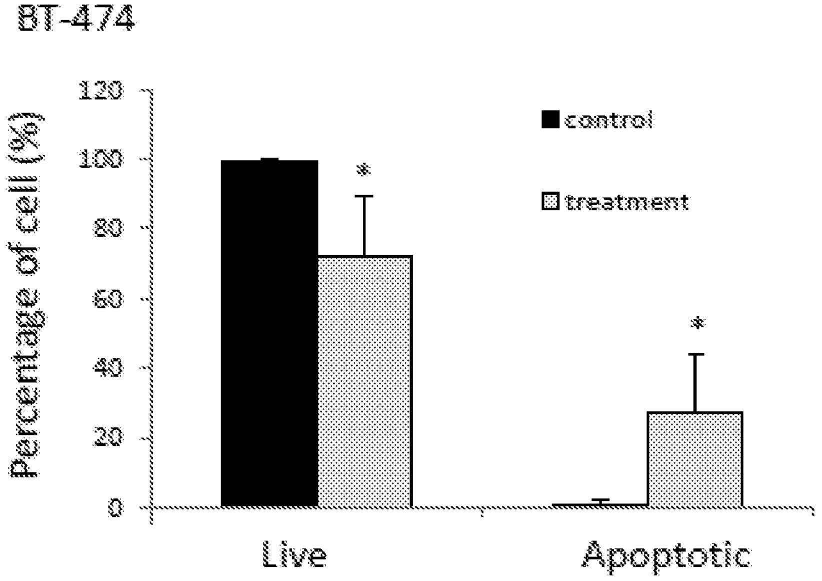
Figure 5D:
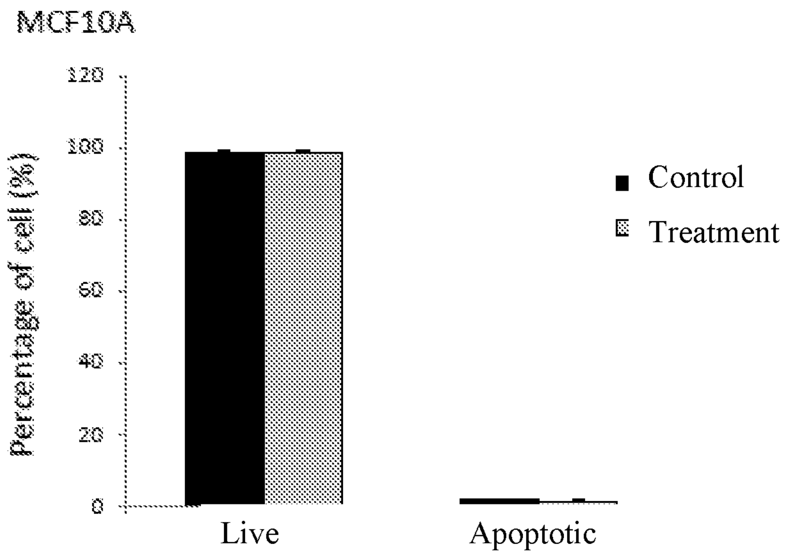

FIGS. 4A and 4B show results of a clonogenic assay, which confirmed the long term effects of Ivabradine on suppression of breast cancer colony formation and proliferation but not in non-tumorigenic breast cells. The breast cancer cells were treated with 200 μM of Ivabradine for 2 weeks and the cells were stained with 0.5% of crystal violet after fixation in 4% formaldehyde. After scanning the images, 10% acetic acid was used to extract the pigment for colorimetric assay. Absorbance at 595 nm was measured. Data was expressed as mean±SD from three independent experiments. Statistical significance at each time point was determined by student t-test.

Figure 18A:
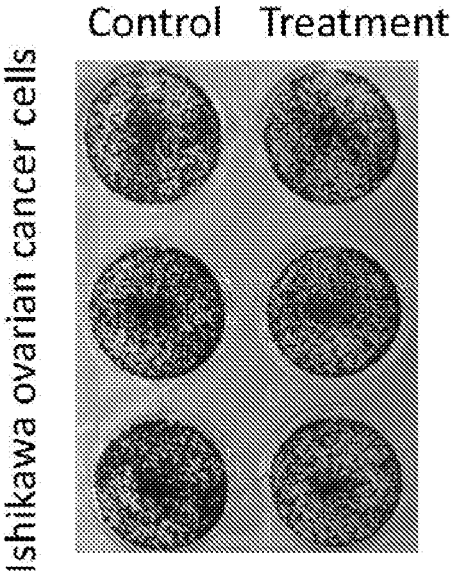
FIGS. 18A and 18B show the colony formation of ISHIKAWA ovarian cancer cells.
Figure 18B:
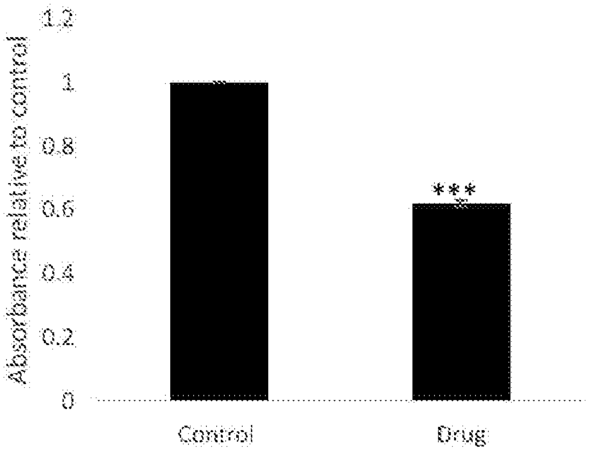

FIGS. 18A and 18B show results of a clonogenic assay, which confirmed the long term effects of Ivabradine on suppression of ovarian cancer colony formation and proliferation. The ovarian cancer cells (Ishikawa) were treated with 200 μM of Ivabradine for 2 weeks and the cells were stained with 0.5% of crystal violet after fixation in 4% formaldehyde. After scanning the images, 10% acetic acid was used to extract the pigment for colorimetric assay. Absorbance at 595 nm was measured. Data was expressed as mean±SD from three independent experiments. Statistical significance at each time point was determined by student t-test.

Figure 18C:
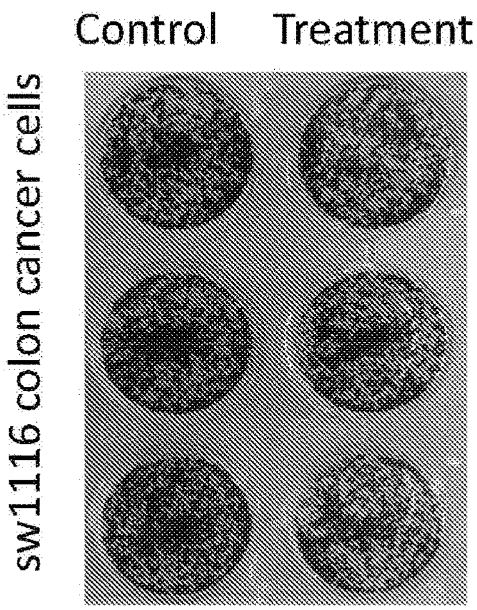
FIGS. 18C and 18D show the colony formation of SW1116 colon cancer cells.
Figure 18D:
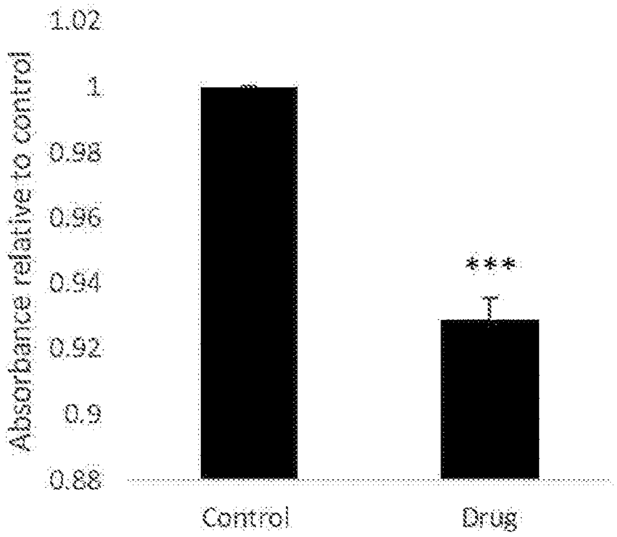

FIGS. 18C and 18D show results of a clonogenic assay, which confirmed the long term effects of Ivabradine on suppression of colon cancer colony formation and proliferation. The colon cancer cells (SW1116) were treated with 200 μM of Ivabradine for 2 weeks and the cells were stained with 0.5% of crystal violet after fixation in 4% formaldehyde. After scanning the images, 10% acetic acid was used to extract the pigment for colorimetric assay. Absorbance at 595 nm was measured. Data was expressed as mean±SD from three independent experiments. Statistical significance at each time point was determined by student t-test.

Figure 18E:
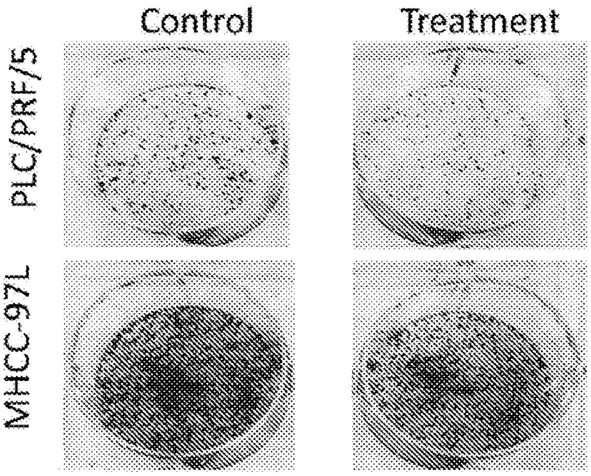
FIGS. 18E and 18F show the colony formation of PLC/PRF/5 and MHCC-97L hepatocellular carcinoma cells. * p<0.05,  p<0.01, *p<0.001. Student t-test was used to determine the statistical significance.
Figure 18F:
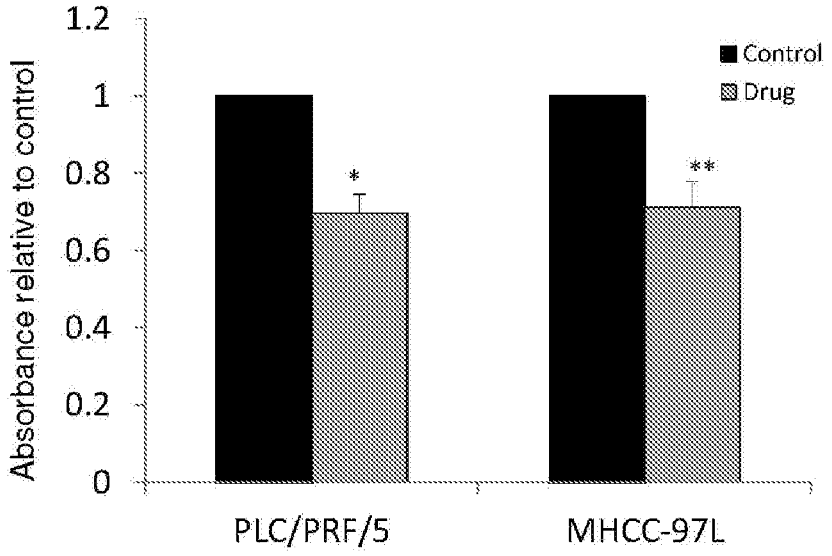

FIGS. 18E and 18F show results of a clonogenic assay, which confirmed the long term effects of Ivabradine on suppression of liver cancer colony formation and proliferation. The liver cancer cells (MHCC-97L and PLC/PRF/5) were treated with 200 μM of Ivabradine for 2 weeks and the cells were stained with 0.5% of crystal violet after fixation in 4% formaldehyde. After scanning the images, 10% acetic acid was used to extract the pigment for colorimetric assay. Absorbance at 595 nm was measured. Data was expressed as mean±SD from three independent experiments. Statistical significance at each time point was determined by student t-test.

Example 5. Ivabradine Induces Apoptosis in Breast Cancer Cell Lines

Materials and Methods

Cells were seeded in 10 cm dish. When the confluence of cells reached 80%, the cells were treated with 200 μM of Ivabradine or double distilled water for 72 hours. The cells were washed with 10 mL of 1×PBS. The cells were detached from the dish by treating the cells with 1 mL of Trypsin (Gibco). The cell suspension was transferred to 15 mL centrifuge tube and subjected to centrifugation at 300×g for 5 minutes at room temperature. The cell pellet was kept. The cell pellet was washed with 5 mL of 1×PBS. The cell suspension was centrifuged at 300×g for 5 minutes at room temperature. The cell pellet was resuspended in 5 mL of 4% paraformaldehyde in PBS and place on ice for 15 minutes. The cell suspension was centrifuged at 300×g for 5 minutes. The cell pellet was washed with 5 mL of 1×PBS. After the washing, the cell suspension was centrifuged at 300×g for 5 minutes at room temperature. The cell pellet was resuspended in 0.5 mL of 1×PBS. The cell suspension was added to 5 mL of ice-cold 70% ethanol for 30 minutes. APO-BrdU TUNEL Assay Kit (ThermoFisher, Cat: A23210) was used. For each cell pellet, DNA labelling solution was prepared by mixing 10 μL of reaction buffer, 0.75 μL of TdT enzyme, 8 μL of BrdUTP and 31.25 μL of double distilled water. The cell pellet was resuspended in 50 μL of the DNA-labeling solution. The cell suspension was incubated at 37° C. for 1 hour. 1 mL of rinse solution was added to the cell suspension and then centrifuged at 300×g for 5 minutes at room temperature. The cell pellet was resuspended by 1 mL of rinse solution and centrifuged at 300×g for 5 minutes at room temperature. 100 μL of antibody staining solution for each pellet was prepared by mixing 5 μL of the Alexa Fluor®488 dye-labeled anti-BrdU antibody with 95 μL of rinse buffer. The cell pellets was resuspended in 100 μL of the antibody solution prepared and incubated for 30 minutes at room temperature in dark. 0.5 mL of the propidium iodide/RNase A staining buffer was added and the cells were incubated for an additional 30 minutes at room temperature in dark. The cells were analysed by BD LSR Fortessa Analyzer.

Results

FIGS. 5A, 5B, 5C, and 5D show data from a flow cytometry analyses which showed inhibition of HCN by Ivabradine treatment significantly induces apoptosis in BT-474, MDA-MB-231 and MDA-MB-453 breast cancer cells but not in non-tumorigenic breast cells MCF10-A. Either 200 μM of Ivabradine (Treatment) or double-distilled water (Control) was used to treat cells for 24 hours (BT474) or 72 hours (MBA-MD-231, MDA-MB-453 and MCF10A). Data was expressed as mean±SD from three independent experiments. * represents $p<0.05$;  represents $p<0.01$; * represents $p<0.001$.

Example 6. Ivabradine Induces Cell Cycle Arrest in Breast Cancer Cell Lines

Materials and Methods

The Materials and Methods were as described in Example 5.

Results

Figure 6A:
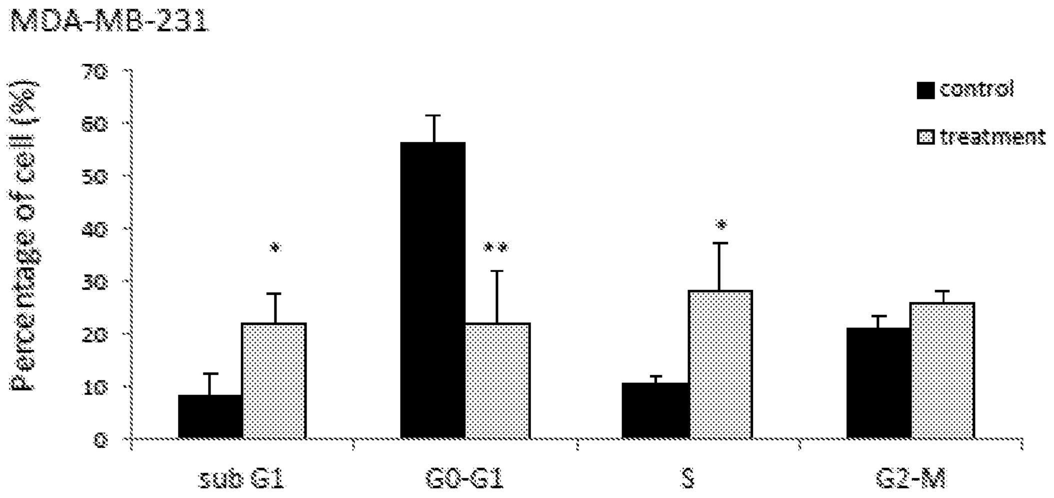
FIGS. 6A, 6B, and 6C are bar graphs showing percentage of cells in sub-G1, G0-G1, S, or G2M cell cycle phases after breast cancer cells MDA-MB-231 (FIG. 6A), MDA-MB-453 (FIG. 6B), and BT-474 (FIG. 6C) were treated with 200 μM of Ivabradine (Treatment) or double-distilled water (Control) for 24 hours (BT474) or 72 hours (MBA-MD-231 and MDA-MB-453). Flow cytometric analysis of cell cycle with propidium iodide DNA staining was performed. Data was expressed as mean±SD from three independent experiments. * represents $p<0.05$;  represents $p<0.01$; * represents $p<0.001$.
Figure 6B:
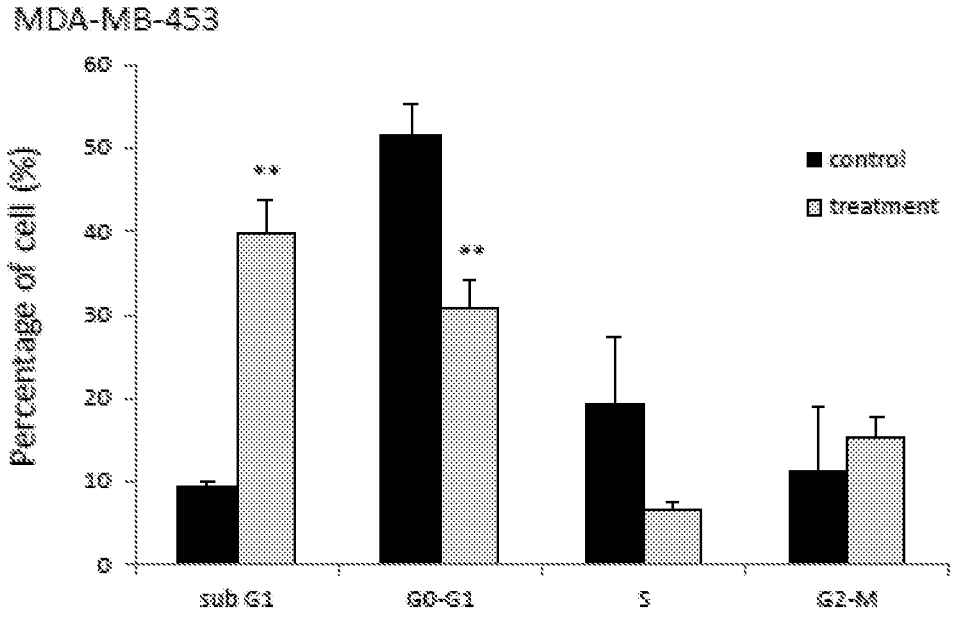
Figure 6C:
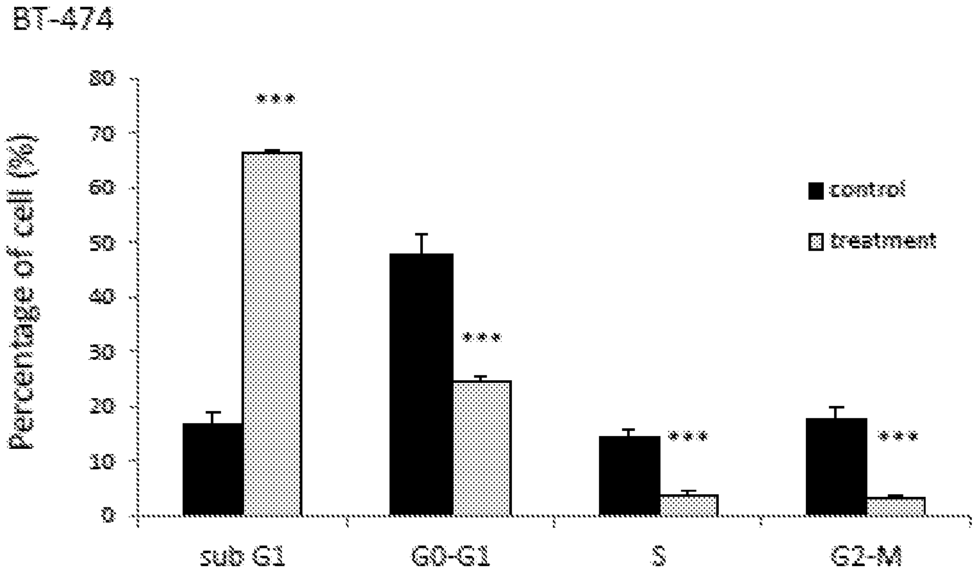

FIGS. 6A, 6B, and 6C are data from a flow cytometry analysis which showed inhibition of HCN by Ivabradine treatment induced sub-G1 cell cycle arrest in BT-474, MDA-MB-231 and MDA-MB-453 breast cancer cells. Either 200 μM of Ivabradine (Treatment) or double-distilled water (Control) was used to treat cells for 24 hours (BT474) or 72 hours (MBA-MD-231, and MDA-MB-453). Flow cytometric analysis of cell cycle with propidium iodide DNA staining was performed. Data was expressed as mean±SD from three independent experiments. * represents $p<0.05$;  represents $p<0.01$; * represents $p<0.001$.

Example 7. Ivabradine Inhibits Tumor Growth In Vivo in Nude Mice

Materials and Methods

The effects of Ivabradine suppression on triple negative breast cancer was investigated in a female nude mouse model with MDA-MB-231 and MDA-MB-453 cells. The cell lines mixed with Matrigel (BD Biosciences) at the ratio of 1:1 were inoculated into the abdominal mammary fat pad of the 5 to 6 week old female nude mice. When the tumors were palpable, the mice were randomized into two groups, each consisting of eight animals. Each group was treated with Ivabradine (15 mg/kg day-1) or water. All reagents were administered via intraperitoneal delivery. Tumor sizes were measured by caliper and tumor volume was calculated as (length*width*width)/2. This protocol has been reviewed and approved by Committee on the Use of Live Animals in Teaching and Research (CULATR), the University of Hong Kong.

Tumor growth was compared between treatment and control groups ($P<0.001$). After 15 days (MDA-MB-231) or 18 days (MDA-MB-453) of the treatment, tumors were isolated and recorded by photo.

Results

Figure 7A:
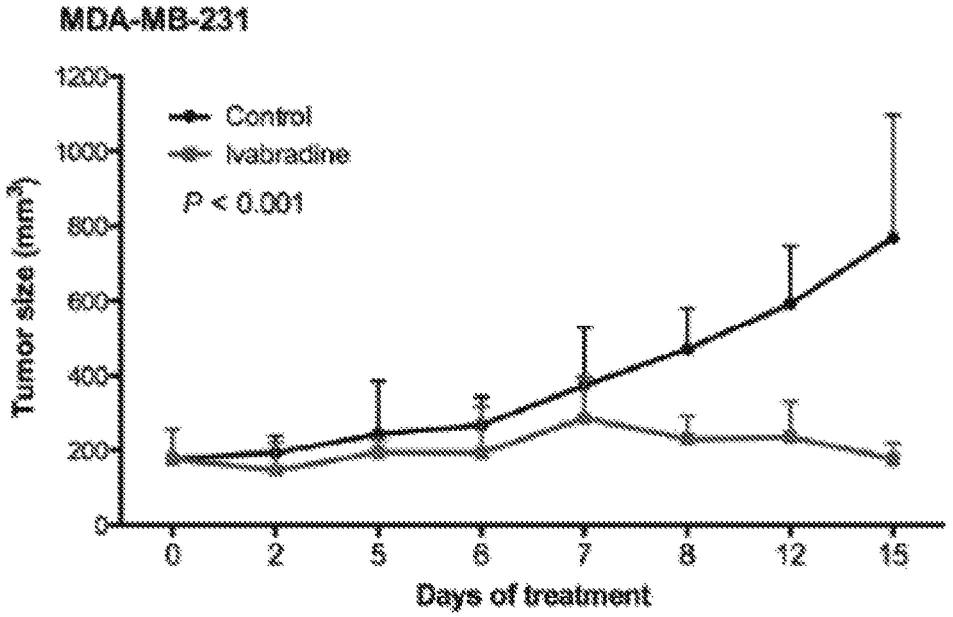
FIGS. 7A and 7B are line graphs showing change in tumor size ($mm^3$) over days of treatment when mice with tumor xenografts from the TNBC cell lines MDA-MB-231 (FIG. 7A) and MDA-MB-453 (FIG. 7B) were treated with Ivabradine or control. Ivabradine was given to the mice via IP injection after the tumor became visible. The dosage of Ivabradine used was 15 mg $kg^{-1}$ $day^{-1}$. Double distilled water was given to the control group. The tumor size was monitored over time, measured by calipers, and the size calculated as $(length \times width^2)/2$. The results were shown as mean±s.d. At least five mice were used in each of the treatment groups. Statistical significance was determined by two-way ANOVA with $P<0.05$ regarded as statistically significant.
Figure 7B:
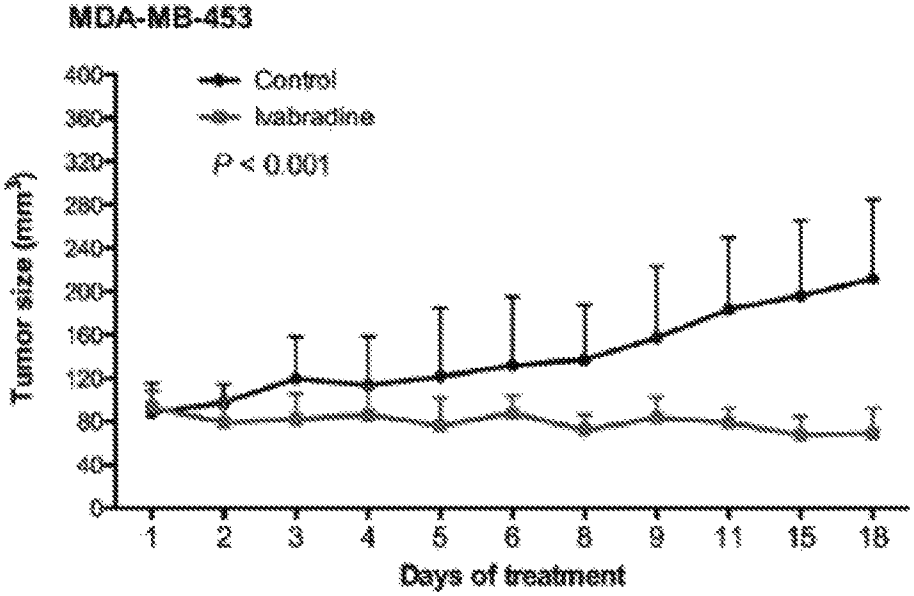

FIGS. 7A and 7B show that Ivabradine treatment could significantly suppress tumor growth in nude mice. TNBC cell lines MDA-MB-231 and MDA-MB-453 were used to establish xenografts in nude mice. About $1\times10^7$ cells were injected into the mammary fat-pad of female nude mice. Ivabradine was given to the mice via IP injection after the tumor became visible. The dosage of Ivabradine used was 15 mg $kg^{-1}$ $day^{-1}$. Double distilled water was given to the control group. The tumor size was monitored over time, measured by calipers, and the size calculated as (length×width$^2$)/2. The results were shown as mean±s.d. At least five mice were used in each of the treatment groups. Statistical significance was determined by two-way ANOVA with $P<0.05$ regarded as statistically significant.

Example 8. Knockdown of HCN2 Expression Using Lentivirus shHCN2

Materials and Methods

HEK239FT cells were co-transfected by pLenti-shHCN2 (RHS11852-EG610) with viral packaging plasmids in 10 cm cell culture dish. For control experiment, HEK239FT cells were co-transfected by pLenti-shScramble with viral packaging plasmids in 10 cm cell culture dish. There were two independent shRNAs (clone 42 and clone 94). For clone 42, the mature antisense sequence was 5'-AGTCGTGGATCTTCTGGCG-3' (SEQ ID NO: 3). For clone 94, the mature antisense sequence was 5'-TCATGCTGAGCATGGTCAG-3' (SEQ ID NO: 1). After 72 hours post-transfection, the culture medium was collected and subjected to centrifuge at 1600×g for 10 minutes at 4° C. The supernatant was collected and subjected to ultracentrifugation at 23,000 rpm with SW28 rotor for 2 hours at 4° C. The supernatant was discarded. The pellet was resuspended in 200 μL of DMEM to prepare viral particle suspension. 20 μL of the suspension was incubated with MDA-MB-231 cells in a 6 well plate for 3 days. After 3 days, the culture medium of MDA-MB-231 was replaced with fresh DMEM (10% FBS and 1% P/S) with 0.5 μg/mL of puromycin. After 2 weeks of the selection, cells were harvested for RNA extraction and reverse transcription for cDNA synthesis. Real time PCR was performed to determine the expression level of HCN2 with GAPDH as internal control.

The MTT assay was performed as in Example 3.

Results

Figure 8:
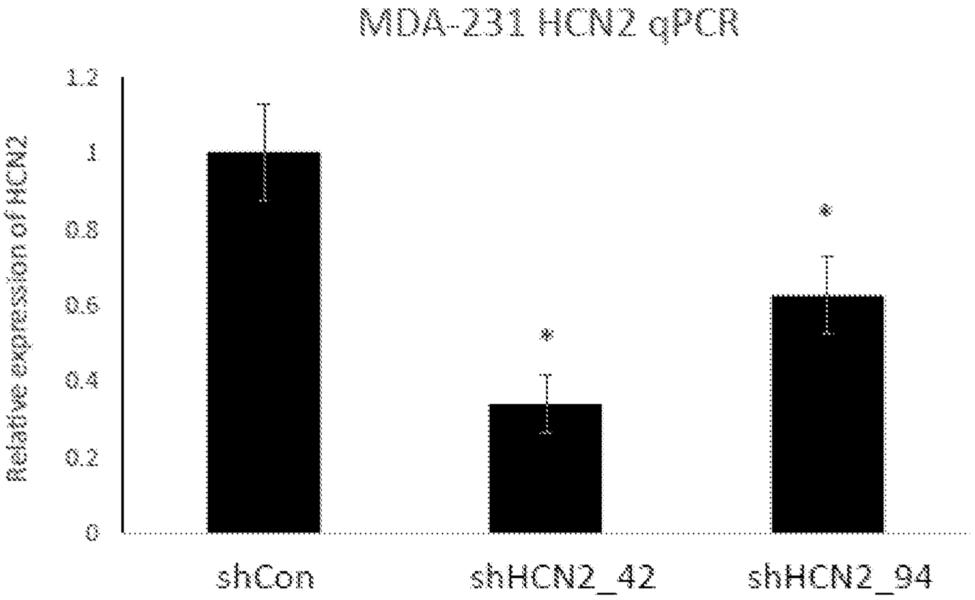
FIG. 8 is a bar graph showing the relative expression of HCN2 after HCN2 mRNA in MDA-MB-231 cell line was knocked down by lentivirus carrying HCN2 channel-specific shRNA shHCN2 42 D7 (clone 42), shHCN2 94 D7 (clone 94), or control shRNA 231 shCon. The knockdown efficiency of clone 42 and clone 94 was shown to be significant both by qPCR and by Western blot. The results were shown as mean±s.d. Statistical significance was determined by two-way ANOVA with $P<0.05$ regarded as statistically significant. * represents $p<0.05$.

FIG. 8 shows stable knockdown of HCN2 channel using lentivirus shHCN2 in MDA-MB-231 cell line. The knockdown efficiency of clone 42 and clone 94 was shown to be significant both by qPCR and by Western blot. The results were shown as mean±s.d. Statistical significance was determined by two-way ANOVA with $P<0.05$ regarded as statistically significant. * represents $P<0.05$; *** represents $P<0.001$.

Figure 9:
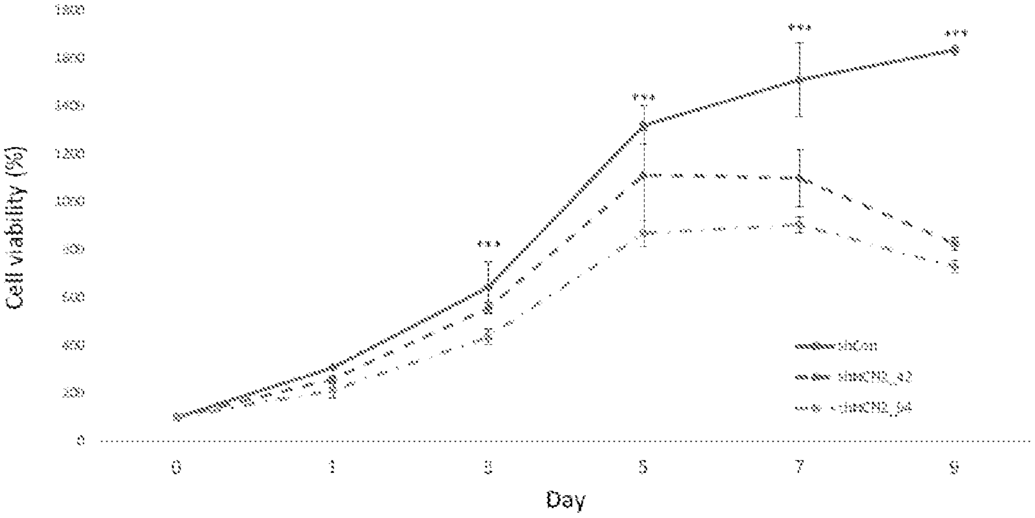
FIG. 9 is a line graph showing cell proliferation over time (days) of MDA-MB-231 cell line, in which the mRNA for HCN2 was knocked down using lentivirus carrying HCN2 channel-specific shRNA shHCN2 (clone 42), shHCN2 (clone 94), or control shRNA 231 shCon. All MTT assays were repeated in triplicate. The results were shown as mean±s.d. Statistical significance was determined by two-way ANOVA with P<0.05 regarded as statistically significant. *** represents p<0.001.

FIG. 9 shows results of an MTT assay, where proliferation of MDA-231 cells with induced shHCN2 was compared to that with scramble control. A significant reduction in MDA-231 cell proliferation was observed when the cells were treated with shHCN2_42RNA or shHCN2_94RNA. The results were shown as mean±s.d. Statistical significance was determined by two-way ANOVA with $P<0.05$ regarded as statistically significant. * represents $P<0.05$; *** represents $P<0.001$.

Statistical analyses: for all the experiments described herein, statistical analyses were conducted using Graphpad Prism 5. Results from MTT assays and mouse model were compared by students' t-test. P values of less than 0.05 were considered statistically significant.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "an inhibitor" includes a plurality of such inhibitors, reference to "the inhibitor" is a reference to one or more inhibitors and equivalents thereof known to those skilled in the art, and so forth.

Throughout the description and claims of this specification, the word "comprise" and variations of the word, such as "comprising" and "comprises" means "including but not limited to", and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about", it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. It should be understood that all of the individual values and sub-ranges of values contained within an explicitly disclosed range are also specifically contemplated and should be considered as being disclosed unless the context specifically indicates otherwise. Finally, it should be understood that all ranges refer both to the recited range as a range and as a collection of individual numbers from and including the first endpoint to and including the second endpoint. In the latter case, it should be understood that any of the individual numbers can be selected as one form of the quantity, value, or feature to which the range refers. In this way, a range describes a set of numbers or values from and including the first endpoint to and including the second endpoint from which a single member of the set (i.e. a single number) can be selected as the quantity, value, or feature to which the range refers. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. may include numerous options and alternatives, this should not be construed as, and is not an admission that, such options and alternatives are equivalent to each other or, in particular, are obvious alternatives. Thus, for example, a list of different HCN inhibitors does not indicate that the listed HCN inhibitors are obvious one to the other, nor is it an admission of equivalence or obviousness.

Those skilled in the art will recognize, or be able to ascertain using no more than routine experimentation, many equivalents to the specific embodiments of the method and compositions described herein. Such equivalents are intended to be encompassed by the following claims.

The invention claimed is:

1. A method for treating cancer in a subject, comprising administering a pharmaceutical composition comprising a hyperpolarization-activated cyclic nucleotide-gated channel (HCN) inhibitor to the subject, wherein the amount of the HCN inhibitor in the pharmaceutical composition is effective, when administered to the subject, to reduce cancer or symptoms associated with cancer in the subject, wherein the HCN inhibitor in the pharmaceutical composition is ivabradine or an inhibitory nucleic acid, wherein the HCN inhibitory nucleic acid comprises a sequence selected from the group consisting of SEQ ID NO:1, SEQ ID NO:2, SEQ ID NO:3, or a combination thereof, and wherein the cancer is breast cancer, ovarian cancer, uterine cancer, prostate cancer, testicular germ cell tumor, brain cancer, gastric cancer, esophagus cancer, lung cancer, liver cancer, or colon cancer.

2. The method of claim 1, wherein the HCN inhibitor is ivabadine.

3. The method of claim 1, wherein the pharmaceutical composition comprising the HCN inhibitor is administered by oral administration, intratracheal administration, intramuscular administration, intravenous administration, intraperitoneal administration, subcutaneous administration, or a combination thereof.

4. The method of claim 1, wherein the subject is a mammal.

5. The method of claim 4, wherein the subject is a human.

6. The method of claim 1, wherein the amount of the HCN inhibitor comprised in the pharmaceutical composition is effective to reduce tumor size in the subject.

7. The method of claim 1, wherein the amount of the HCN inhibitor comprised in the pharmaceutical composition is effective to induce cancer remission in the subject.

8. The method of claim 1, wherein the amount of the HCN inhibitor comprised in the pharmaceutical composition is effective to reduce at least one symptom of cancer in the subject.

9. The method of claim 1, wherein the amount of the HCN inhibitor comprised in the pharmaceutical composition is effective to reduce or stop proliferation of cancer stem cells in the subject.

10. The method of claim 1, wherein the pharmaceutical composition further comprises a pharmaceutically acceptable carrier.

11. The method of claim 1, wherein the HCN inhibitor is an inhibitory nucleic acid, wherein the inhibitory nucleic acid comprises a sequence selected from the group comprising SEQ ID NO:1, SEQ ID NO:2, SEQ ID NO:3, or a combination thereof.

12. A method for inhibiting hyperpolarization-activated cyclic nucleotide-gated channel (HCN) activity in cancer cells, the method comprising contacting the cancer cells with a composition comprising an HCN inhibitor, wherein the amount of the HCN inhibitor in the composition is effective to reduce proliferation of the cancer cells, induce apoptosis of the cancer cells, or both, wherein the HCN inhibitor is selected from the group consisting of ivabradine and an HCN inhibitory nucleic acid, wherein the inhibitory nucleic acid comprises a comprises a sequence selected from the group comprising SEQ ID NO:1, SEQ ID NO:2, SEQ ID NO:3, or a combination thereof.

* * * * *

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: mature antisense sequences for targeting HCN2
```

-continued

```
      mRNA

<400> SEQUENCE: 1

tcatgctgag catggtcag                                                19


<210> SEQ ID NO 2
<211> LENGTH: 19
<212> TYPE: DNA
<213> ORGANISM: Artificial Sequence
<220> FEATURE:
<223> OTHER INFORMATION: mature antisense sequences for targeting HCN2
      mRNA

<400> SEQUENCE: 2

tcttcttgat cttctcggg                                                19


<210> SEQ ID NO 3
<211> LENGTH: 19
<212> TYPE: DNA
<213> ORGANISM: Artificial Sequence
<220> FEATURE:
<223> OTHER INFORMATION: mature antisense sequences for targeting HCN2
      mRNA

<400> SEQUENCE: 3

agtcgtggat cttctggcg                                                19
```